US010639468B2

(12) United States Patent
Cook et al.

(10) Patent No.: US 10,639,468 B2
(45) Date of Patent: *May 5, 2020

(54) DEVICES, SYSTEMS AND METHODS FOR THE TREATMENT OF MEDICAL DISORDERS

(71) Applicant: THE REGENTS OF THE UNIVERSITY OF CALIFORNIA, Oakland, CA (US)

(72) Inventors: Ian A. Cook, Los Angeles, CA (US); Christopher M. DeGiorgio, Valencia, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/650,707

(22) Filed: Jul. 14, 2017

(65) Prior Publication Data

US 2018/0001077 A1 Jan. 4, 2018

Related U.S. Application Data

(63) Continuation of application No. 13/994,541, filed as application No. PCT/US2011/065002 on Dec. 14, (Continued)

(51) Int. Cl.
*A61N 1/04* (2006.01)
*A61N 1/36* (2006.01)
*A61N 1/05* (2006.01)

(52) U.S. Cl.
CPC ......... *A61N 1/0456* (2013.01); *A61N 1/0526* (2013.01); *A61N 1/0551* (2013.01); (Continued)

(58) Field of Classification Search
CPC ............... A61N 1/0456; A61N 1/0526; A61N 1/36014; A61N 1/36025
See application file for complete search history.

(56) References Cited

U.S. PATENT DOCUMENTS 3,279,468 A 10/1966 Le Vine
3,709,228 A 1/1973 Barker
(Continued)

FOREIGN PATENT DOCUMENTS

AU 2010303586 12/2015
JP 7289649 A 11/1995
(Continued)

OTHER PUBLICATIONS

Degiorgio Christopher M. et al., Trigeminal Nerve Stimulation for Epilepsy: Long-Term Feasibility and Efficacy, Neurology, Mar. 10, 2009, vol. 72, No. 10, 936-938.
(Continued)

*Primary Examiner* — William J Levicky
(74) *Attorney, Agent, or Firm* — Vista IP Law Group LLP

(57) ABSTRACT

The present disclosure relates to methods, devices and systems used for the treatment of medical disorders via stimulation of the superficial elements of the trigeminal nerve. More specifically, cutaneous methods of stimulation of the superficial branches of the trigeminal nerve located extracranially in the face, namely the supraorbital, supratrochlear, infraorbital, auriculotemporal, zygomaticotemporal, zygomaticoorbital, zygomaticofacial, infraorbital, nasal and mentalis nerves (also referred to collectively as the superficial trigeminal nerve) are disclosed herein.

9 Claims, 23 Drawing Sheets

Related U.S. Application Data 2011, now abandoned, and a continuation-in-part of application No. 12/898,675, filed on Oct. 5, 2010, now Pat. No. 8,688,220, and a continuation-in-part of application No. 12/898,686, filed on Oct. 5, 2010, now Pat. No. 8,380,315.

(60) Provisional application No. 61/479,787, filed on Apr. 27, 2011, provisional application No. 61/445,505, filed on Feb. 22, 2011, provisional application No. 61/440,784, filed on Feb. 8, 2011, provisional application No. 61/423,011, filed on Dec. 14, 2010, provisional application No. 61/354,641, filed on Jun. 14, 2010, provisional application No. 61/305,514, filed on Feb. 17, 2010, provisional application No. 61/289,829, filed on Dec. 23, 2009, provisional application No. 61/248,827, filed on Oct. 5, 2009.

(52) U.S. Cl.
CPC ..... *A61N 1/36014* (2013.01); *A61N 1/36017* (2013.01); *A61N 1/36025* (2013.01); *A61N 1/361* (2013.01); *A61N 1/36053* (2013.01); *A61N 1/36064* (2013.01); *A61N 1/36085* (2013.01); *A61N 1/36089* (2013.01); *A61N 1/36096* (2013.01); *A61N 1/36114* (2013.01)

(56) References Cited

U.S. PATENT DOCUMENTS

| | | |
|---|---|---|
| 4,233,986 A | 11/1980 | Tannenbaum |
| 4,305,402 A | 12/1981 | Katims |
| 4,635,641 A | 1/1987 | Hoffman |
| 5,514,175 A | 5/1996 | Kim et al. |
| 5,540,734 A | 7/1996 | Zabara |
| 5,549,734 A | 8/1996 | Standard |
| 5,814,095 A | 9/1998 | Muller et al. |
| 6,061,593 A | 5/2000 | Fischell et al. |
| 6,405,079 B1 | 6/2002 | Ansarinia |
| 6,549,808 B1 | 4/2003 | Gisel et al. |
| 6,567,702 B1 | 5/2003 | Nekhendzy et al. |
| 6,735,475 B1 | 5/2004 | Whitehurst et al. |
| 6,950,707 B2 | 9/2005 | Whitehurst |
| 6,954,668 B1 | 10/2005 | Cuozzo |
| 7,003,352 B1 | 2/2006 | Whitehurst |
| 7,171,276 B2 | 1/2007 | Giuntoli et al. |
| 7,502,652 B2 | 3/2009 | Gaunt et al. |
| 7,734,340 B2 | 6/2010 | De Ridder |
| 7,769,461 B2 | 8/2010 | Whitehurst et al. |
| 7,801,601 B2 | 9/2010 | Maschino et al. |
| 8,315,704 B2 | 11/2012 | Jaax et al. |
| 8,380,315 B2 * | 2/2013 | DeGiorgio ........... A61N 1/0456 607/45 |
| 8,428,734 B2 | 4/2013 | Rigaux et al. |
| 8,494,641 B2 | 7/2013 | Boling et al. |
| 8,512,715 B2 | 8/2013 | Papay |
| 8,554,324 B2 | 10/2013 | Brocke |
| 8,565,896 B2 | 10/2013 | Ben-David et al. |
| 8,591,419 B2 | 11/2013 | Tyler |
| 8,666,498 B2 | 3/2014 | Newman |
| 8,688,220 B2 | 4/2014 | DeGiorgio et al. |
| 8,700,164 B2 * | 4/2014 | DeGiorgio ........... A61N 1/0456 607/45 |
| 8,849,407 B1 | 9/2014 | Danilov |
| 8,958,880 B2 * | 2/2015 | DeGiorgio ........... A61N 1/0456 607/45 |
| 9,186,510 B2 | 11/2015 | Gliner et al. |
| 9,238,139 B2 * | 1/2016 | DeGiorgio ........... A61N 1/0456 |
| 9,364,674 B2 | 6/2016 | Cook et al. |
| 9,504,827 B2 | 11/2016 | DeGiorgio et al. |
| 9,511,223 B2 | 12/2016 | DeGiorgio et al. |
| 9,682,236 B2 | 6/2017 | DeGiorgio |
| 10,016,601 B2 | 7/2018 | Cook et al. |
| 10,058,704 B2 | 8/2018 | DeGiorgio et al. |
| 10,195,435 B2 | 2/2019 | DeGiorgio et al. |
| 10,238,862 B2 | 3/2019 | Cook et al. |
| 10,322,283 B2 | 6/2019 | DeGiorgio et al. |
| 2002/0077670 A1 | 6/2002 | Archer et al. |
| 2003/0045922 A1 | 3/2003 | Northrop |
| 2003/0195588 A1 | 10/2003 | Fischell et al. |
| 2004/0127965 A1 | 7/2004 | Borkan |
| 2004/0138097 A1 | 7/2004 | Guyuron |
| 2004/0172089 A1 | 9/2004 | Whitehurst et al. |
| 2004/0176820 A1 | 9/2004 | Paul |
| 2004/0243207 A1 | 12/2004 | Olson et al. |
| 2005/0222657 A1 | 10/2005 | Wahlstrand et al. |
| 2005/0283198 A1 | 12/2005 | Haubrich |
| 2006/0015153 A1 | 1/2006 | Gliner et al. |
| 2006/0050912 A1 | 3/2006 | Kidd et al. |
| 2006/0064140 A1 | 3/2006 | Whitehurst et al. |
| 2006/0167500 A1 | 7/2006 | Towe et al. |
| 2006/0173510 A1 | 8/2006 | Besio et al. |
| 2006/0190053 A1 | 8/2006 | Dobak, III |
| 2006/0200208 A1 | 9/2006 | Terry et al. |
| 2006/0206165 A1 | 9/2006 | Jaax et al. |
| 2006/0235484 A1 | 10/2006 | Jaax et al. |
| 2006/0293723 A1 | 12/2006 | Whitehurst et al. |
| 2007/0049988 A1 | 3/2007 | Carbunaru et al. |
| 2007/0060975 A1 | 3/2007 | Mannheimer et al. |
| 2007/0142874 A1 | 6/2007 | John |
| 2007/0150025 A1 | 6/2007 | DiLorenzo et al. |
| 2007/0150027 A1 | 6/2007 | Rogers |
| 2007/0173908 A1 | 7/2007 | Begnaud |
| 2007/0179557 A1 | 8/2007 | Maschino et al. |
| 2007/0233194 A1 | 10/2007 | Craig |
| 2007/0250145 A1 | 10/2007 | Kraus et al. |
| 2007/0276451 A1 | 11/2007 | Rigaux |
| 2008/0046013 A1 | 2/2008 | Lozano |
| 2008/0103547 A1 | 5/2008 | Okun et al. |
| 2008/0128215 A1 | 6/2008 | Nowitz |
| 2008/0132980 A1 | 6/2008 | Gerber et al. |
| 2008/0140151 A1 | 6/2008 | Brodkey |
| 2008/0147141 A1 | 6/2008 | Testerman et al. |
| 2008/0161713 A1 | 7/2008 | Leyde et al. |
| 2008/0171929 A1 | 7/2008 | Katims |
| 2008/0172101 A1 | 7/2008 | Bolea et al. |
| 2008/0262566 A1 | 10/2008 | Jaax |
| 2008/0269716 A1 | 10/2008 | Bonde et al. |
| 2008/0275327 A1 | 11/2008 | Faarbaek et al. |
| 2009/0048642 A1 | 2/2009 | Goroszeniuk |
| 2009/0210028 A1 | 8/2009 | Rigaux et al. |
| 2009/0287035 A1 | 11/2009 | Dietrich et al. |
| 2010/0030227 A1 | 2/2010 | Kast et al. |
| 2010/0114240 A1 | 5/2010 | Guntinas-Lichius et al. |
| 2010/0198044 A1 | 8/2010 | Gehman et al. |
| 2010/0198282 A1 | 8/2010 | Rogers |
| 2010/0222847 A1 | 9/2010 | Goetz |
| 2010/0228105 A1 | 9/2010 | Policker et al. |
| 2010/0228113 A1 | 9/2010 | Solosko et al. |
| 2010/0262205 A1 | 10/2010 | De Ridder |
| 2011/0093033 A1 * | 4/2011 | Nekhendzy ........ A61N 1/36017 607/46 |
| 2011/0106220 A1 | 5/2011 | DeGiorgio et al. |
| 2011/0112603 A1 | 5/2011 | DeGiorgio et al. |
| 2011/0184489 A1 | 7/2011 | Nicolelis et al. |
| 2011/0218589 A1 | 9/2011 | DeGiorgio et al. |
| 2011/0218590 A1 * | 9/2011 | Degiorgio ............ A61N 1/0456 607/45 |
| 2011/0270361 A1 | 11/2011 | Borsody |
| 2011/0282129 A1 | 11/2011 | Rigaux |
| 2011/0282412 A1 | 11/2011 | Glukhovsky et al. |
| 2011/0288610 A1 | 11/2011 | Brocke |
| 2012/0203301 A1 | 8/2012 | Cameron et al. |
| 2012/0330380 A1 | 12/2012 | Corndorf |
| 2013/0158626 A1 | 6/2013 | DeGiorgio et al. |
| 2014/0039572 A1 | 2/2014 | Bradley |
| 2014/0046407 A1 | 2/2014 | Ben-Ezra et al. |
| 2014/0081353 A1 | 3/2014 | Cook et al. |
| 2014/0081369 A1 | 3/2014 | Sosa et al. |
| 2014/0135886 A1 | 5/2014 | Cook et al. |
| 2014/0142669 A1 | 5/2014 | Cook et al. |
| 2014/0148872 A1 | 5/2014 | Goldwasser et al. |

(56) References Cited

U.S. PATENT DOCUMENTS

| | | |
|---|---|---|
| 2014/0188200 A1 | 7/2014 | DeGiorgio |
| 2014/0206945 A1 | 7/2014 | Liao |
| 2015/0151128 A1 | 6/2015 | DeGiorgio |
| 2016/0106979 A1 | 4/2016 | DeGiorgio |
| 2016/0129254 A1 | 5/2016 | DeGiorgio et al. |
| 2016/0317814 A1 | 11/2016 | DeGiorgio et al. |
| 2016/0339242 A1 | 11/2016 | Cook et al. |
| 2017/0028198 A1 | 2/2017 | DeGiorgio et al. |
| 2017/0056660 A1 | 3/2017 | DeGiorgio et al. |
| 2017/0259063 A1 | 9/2017 | DeGiorgio et al. |
| 2017/0348521 A1 | 12/2017 | Cook et al. |
| 2018/0229029 A1 | 8/2018 | Cook et al. |
| 2019/0269922 A1 | 9/2019 | DeGiorgio |

FOREIGN PATENT DOCUMENTS

| | | |
|---|---|---|
| JP | 8-229141 A | 10/1996 |
| JP | 8-299141 A | 10/1996 |
| JP | 2007-061267 A | 3/2007 |
| JP | 2007-54299 A | 8/2007 |
| JP | 2008-506464 T | 3/2008 |
| JP | 2008-516696 A | 5/2008 |
| JP | 2008-246040 A | 10/2008 |
| JP | 2009-502315 A | 1/2009 |
| JP | 2009-505689 A | 2/2009 |
| JP | 2009-531154 A | 9/2009 |
| JP | 4961558 B2 | 6/2012 |
| JP | 2003-339884 A | 12/2013 |
| RU | 2086227 C1 | 8/1997 |
| RU | 2185092 C1 | 7/2002 |
| SU | 1718976 A1 | 3/1992 |
| WO | 2005/062829 A2 | 7/2005 |
| WO | 2006/044792 A2 | 4/2006 |
| WO | 2006/044792 A3 | 4/2006 |
| WO | 2006/044793 A2 | 4/2006 |
| WO | 2006/051370 | 5/2006 |
| WO | 2007/018793 A1 | 2/2007 |
| WO | 2007/018797 A1 | 2/2007 |
| WO | 2007/136726 | 11/2007 |
| WO | 2008/128215 A1 | 10/2008 |
| WO | 2009/158389 | 12/2009 |
| WO | 2010/057998 A1 | 5/2010 |
| WO | 2011/044173 | 4/2011 |
| WO | 2011/044176 | 4/2011 |
| WO | 2011/044178 | 4/2011 |
| WO | 2011/044179 | 4/2011 |
| WO | 2012/075192 A2 | 6/2012 |
| WO | 2012/082960 | 6/2012 |
| WO | 2012/082961 | 6/2012 |
| WO | 2013/104552 A1 | 7/2013 |
| WO | 2013/152316 A1 | 10/2013 |

OTHER PUBLICATIONS

Narouze et al., Supraorbital Nerve Electric Stimulation for the Treatment of Intractable Chronic Cluster Headache: A Case Report, Jul. 2007.

Reed et al., Combined occipital and supraorbital neurostimulation for the treatment of chronic migraine headaches: Initial experience, published online Feb. 15, 2010.

Cherkasova, Mariya V et al., Neuroimaging in Attention-Deficit Hyperactivity Disorder: Beyond the Frontostriatal Circuity, The Canadian Journal of Psychiatry, vol. 54, No. 10, Oct. 2009, 651-664.

Dickstein, Steven G. et al., The neural correlates of attention deficit hyperactivity disorder: an ALE meta-analysis, Journal of Child Psychology and Psychiatry, 47:10(2006), pp. 1051-1062.

Hall, Goeffrey B.C. et al., Enhanced Salience and Emotion Recognition in Autism: A PET Study, Am J Psychiatry, 160:8, Aug. 2003, http://ajp.psychiatryonline.org., 1439-1441.

Konrad, Kerstin et al., Dysfunctional Attentional Networks in Children with Attention Deficit/Hyperactivity Disorder: Evidence from an Event-Related Functional Magnetic Resonance Imaging Study, Biol Psychiatry, 2006, 59:643-651.

McAlonan, Grainne M. et al., Mapping the brain in autism. A voxel-based MRI study of volumetric differences and intercorrelations in autism, Brain (2005), 128, 268-276.

Makris, Nikos et al., Anterior Cingulate Volumetric Alterations in Treatment-Naive Adults with ADHD, J Atten Disord. Jan. 2010; 13(4): 407-413. doi:10.1177/1087054709351671.

Ahmed, H. E. et al. "Use of Percutaneous Electrical Nerve Stimulation (PENS) in the Short-term Management of Headache". Headache, 40:311-315 (2000).

Allais, G. et al., "Non-pharmacological approaches to chronic headaches: transcutaneous electricalnerve stimulation, lastertherapy and acupuncture in transformed migraine treatment". Neuro Sci, 24:S138-S142 (2003).

Degiorgio, C. et al., "Trigeminalnerve stimulation for epilepsy." Neurology, 61:421-422 (2003).

Degiorgio C.et al., "Pilot Study of TrigeminalNerve Stimulation (TNS) for Epilepsy: A Proof-of-Concept Trial". Epilepsia, 47(7):1213-1215 (2006).

Moseley, B.D. and Degiorgio,C., "Refractory status epilepticus treated with trigeminal nerve stimulation." Epilepsy Research, 108: 600-603 (2014).

Office Action dated Jun. 14, 2018 in U.S. Appl. No. 15/949,987, (51pages).

Notice of Reasons for Rejection dated Nov. 19, 2018 in Japanese Patent Appl No. 2013-544760, (5pages).

Examination Report dated Jun. 19, 2019 in Canadian Patent Appl No. 2821981, (4pages).

Communication pursuant to Article 94(3) EPC dated Feb. 28, 2019 in European Patent Appl No. 11849085.3, (6pages).

Examination Report dated Dec. 29, 2018 in Korean Patent Appl No. 10-2013-7018221, (22pages).

Decision of Refusal dated Sep. 28, 2019 in Korean Patent Appl No. 10-2013-7018221, (8pages).

Response to Examination Report dated Dec. 17, 2019 in Canadian Patent Appl No. 2821981, (12pages).

Decision to Reject Reexamination dated Jan. 2, 2020 in Korean Patent Appl No. 10-2013-7018221, (4pages).

Decision of Refusal dated Jan. 2, 2020 in Korean Patent Appl No. 10-2013-7018221, (5pages).

\* cited by examiner

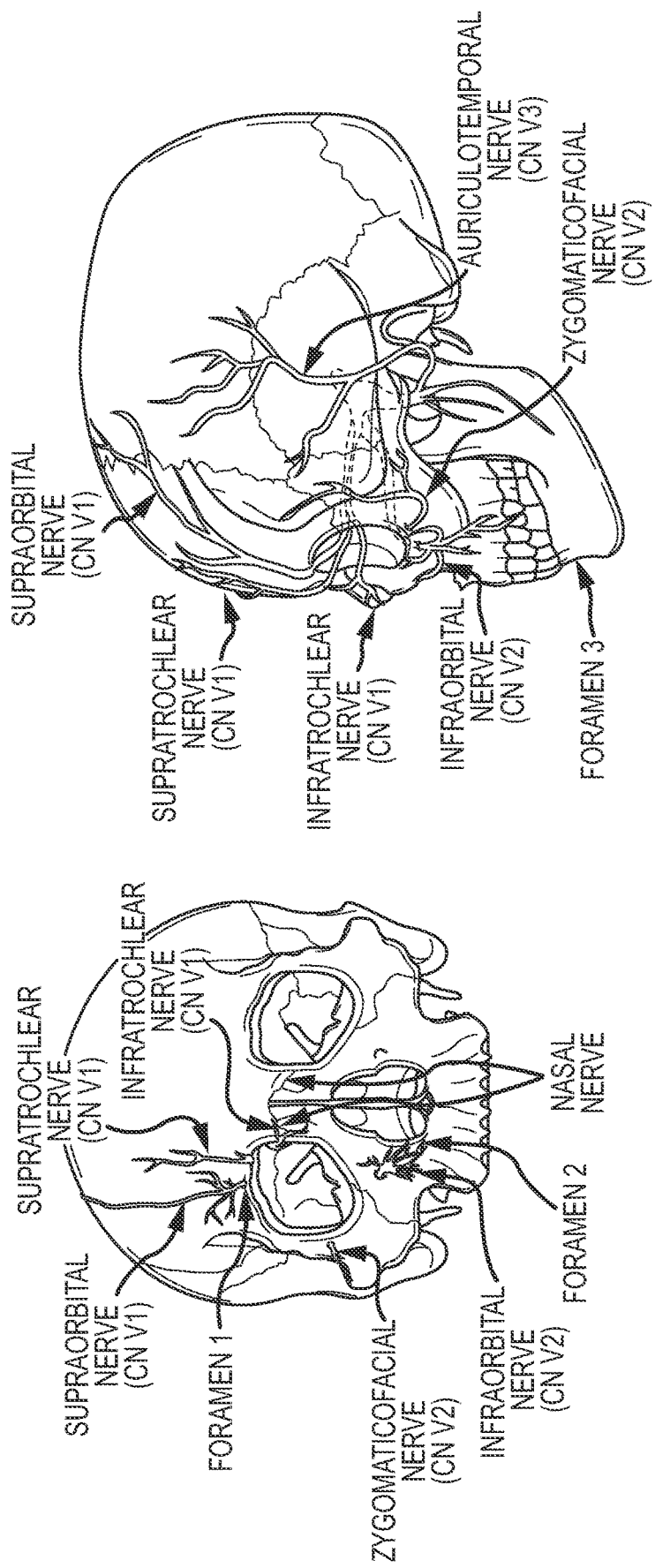

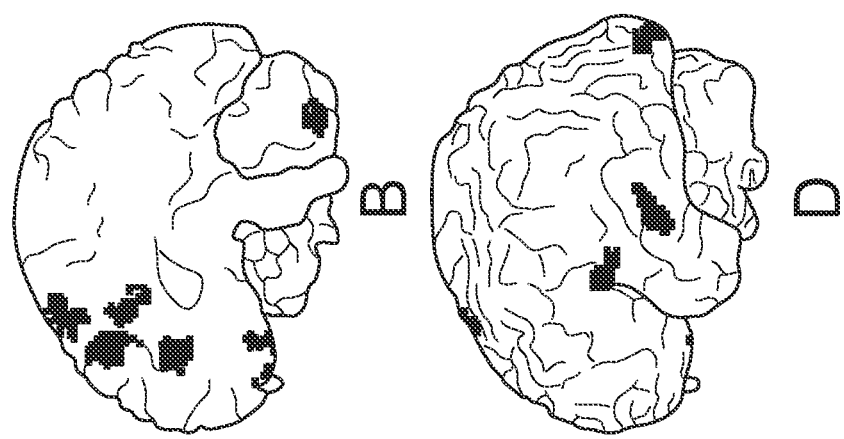
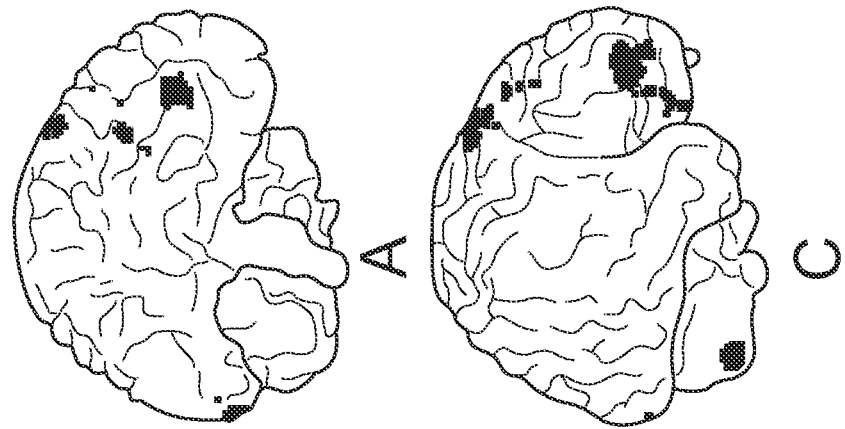
FIG. 2

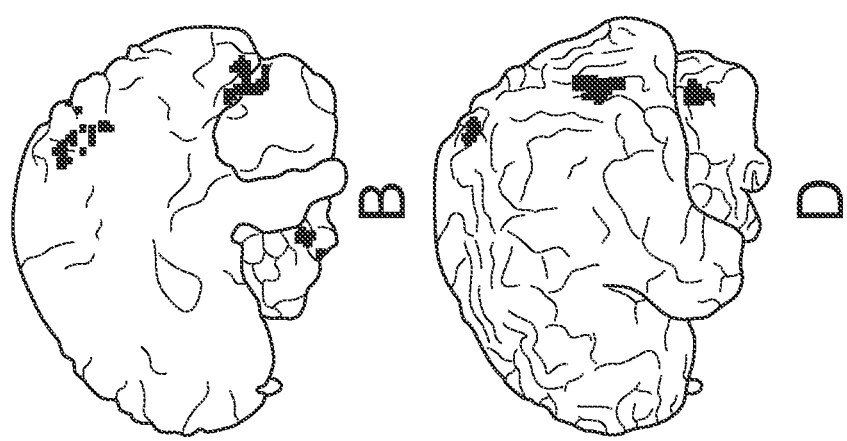
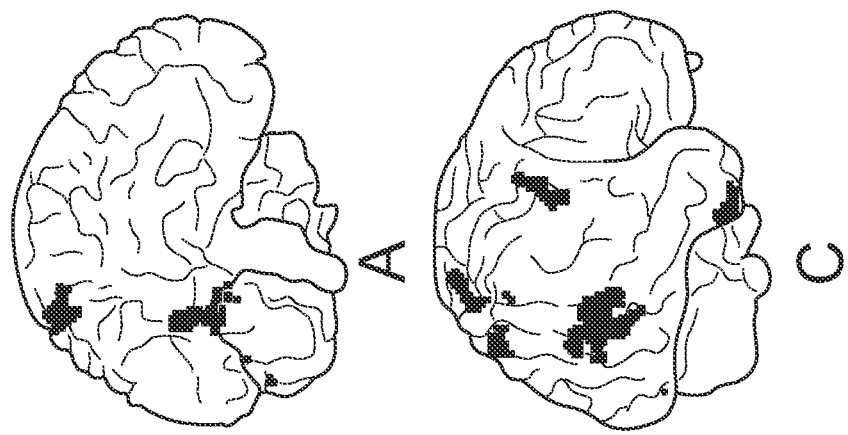
FIG. 3

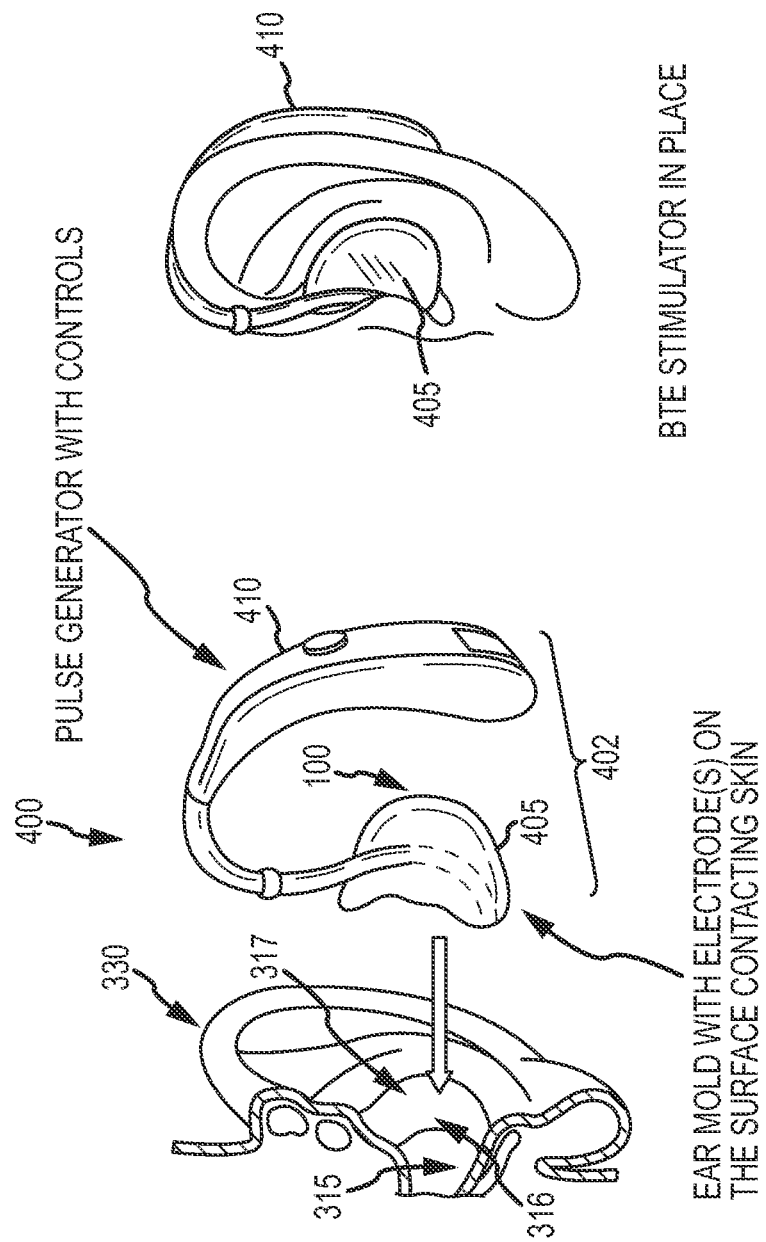

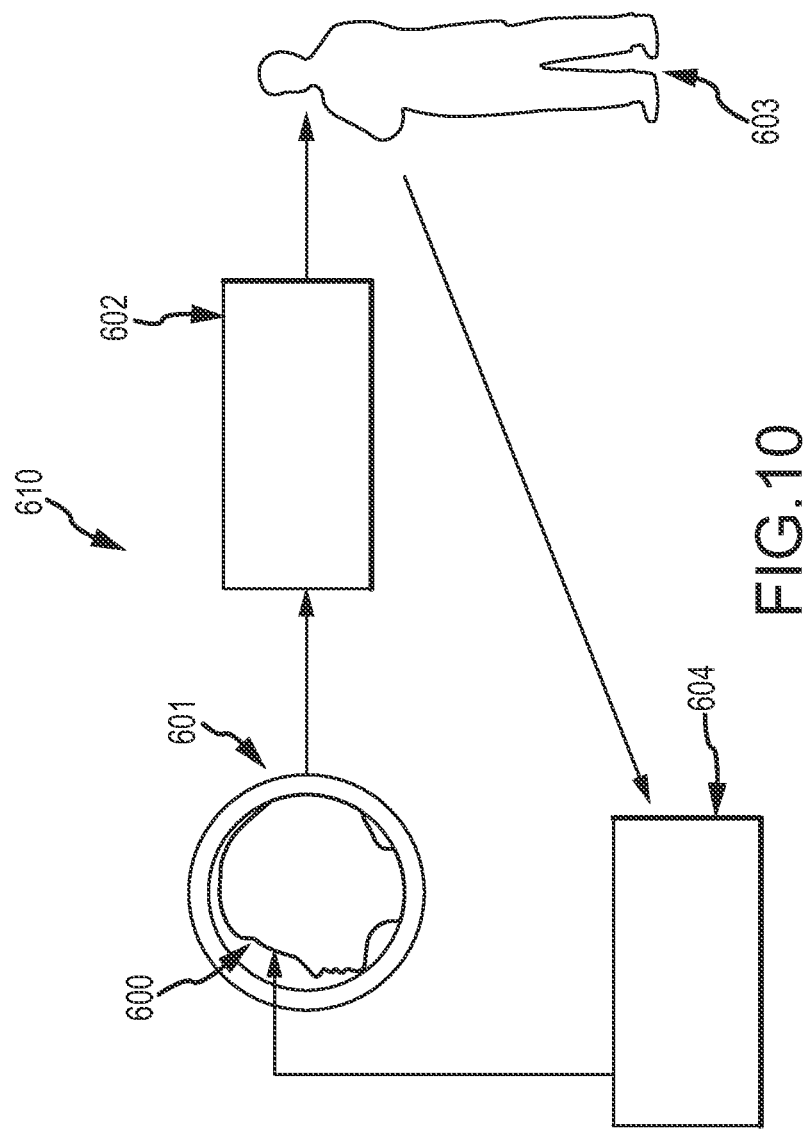

PRE- TO POST-TREATMENT COMPARISON

|  | BDI | $HDRS_{28}$ | $HDRS_{17}$ | $QIDS_{16}$ |
|---|---|---|---|---|
| BASELINE | 26.8 (8.1) | 25.4 (3.9) | 16.2 (3.3) | 10.8 (2.8) |
| FINAL | 8.4 (4.9) | 12.6 (6.4) | 8.8 (4.4) | 5.4 (3.8) |
| 2-TAIL P-VALUE | 0.0004 | 0.006 | 0.005 | 0.01 |
| % CHANGE | 70.2% | 51.1% | 45.6% | 58.1% |
| COHEN'S d E.S | 2.7 | 2.4 | 1.9 | 1.3 |

| PULSE DURATION (Usec) | 150us | 200us | 250us |
|---|---|---|---|
| mA'S RECORDED (MAX TOLERATED SETTINGS) | 7.92 | 5.94 | 5.72 |
| ELECTRODE RADIUS(cm) (1.25" DIAMETER ROUND ELECTRODES) | 1.59cm | 1.59cm | 1.59cm |
| SURFACE AREA cm | 7.92cm$^2$ | 7.92cm$^2$ | 7.92cm$^2$ |
| CURRENT DENSITY mA/cm$^2$ | 1 | .75 | .72 |
| MAXIMUM SAFE CURRENT DENSITY AT STIMULATING ELECTRODE mA/cm$^2$ | 25 | 25 | 25 |
| CHARGE DENSITY (A)(pulse)/cm$^2$ =uC/cm$^2$ AT STIMULATING ELECTRODE | .15 | .15 | 0.18 |
| MAXIMUM SAFE CHARGE DENSITY (uC/cm$^2$) AT BRAIN | 10 | 10 | 10 |

FIG.12

| MINUTES | ON TIME | OFF TIME | DUTY CYCLE |
|---|---|---|---|
| 10 | 10 SECONDS | 60 SECONDS | 12.50% |
| 20 | 20 SECONDS | 60 SECONDS | 25% |
| 30 | 30 SECONDS | 60 SECONDS | 33% |
| 40 | 30 SECONDS | 60 SECONDS | 33% |
| 50 | 20 SECONDS | 60 SECONDS | 25% |
| 60 | 10 SECONDS | 60 SECONDS | 12.50% |
| 70 | 20 SECONDS | 30 SECONDS | 40% |
| 80 | 30 SECONDS | 30 SECONDS | 50% |
| 90 | 30 SECONDS | 30 SECONDS | 50% |
| 100 | 20 SECONDS | 30 SECONDS | 40% |
| 120 | 10 SECONDS | 30 SECONDS | 25% |
| 130 | 10 SECONDS | 60 SECONDS | 12.50% |
| 140 | 20 SECONDS | 60 SECONDS | 25% |
| 150 | 30 SECONDS | 60 SECONDS | 33% |
| 160 | 30 SECONDS | 60 SECONDS | 33% |
| 170 | 20 SECONDS | 60 SECONDS | 25% |
| 180 | 10 SECONDS | 60 SECONDS | 12.50% |

FIG.15A

DEVICES, SYSTEMS AND METHODS FOR THE TREATMENT OF MEDICAL DISORDERS

CROSS REFERENCE TO RELATED APPLICATIONS

This application is a continuation of U.S. application Ser. No. 13/994,541, which is a U.S. National Stage filing under 35 U.S.C. § 371 of PCT Patent Application No. PCT/US2011/065002, filed Dec. 14, 2011, which itself claims the benefit of priority under 35 U.S.C. § 119(e) to the following applications: U.S. Application No. 61/423,011, entitled "Devices, Systems and Methods for Treatment of Neuropsychiatric Disorders," filed on Dec. 14, 2010; U.S. Application No. 61/440,784, entitled "Devices, Systems and Methods for Treatment of Cardiac Related Disorders," filed on Feb. 8, 2011; U.S. Application No. 61/445,505, entitled "Devices, Systems and Methods for Treatment of Fatigue and Other Medical Disorders," filed on Feb. 22, 2011; and U.S. Application No. 61/479,787, entitled "Devices, Systems and Methods for Treatment of Medical Disorders," filed on Apr. 27, 2011 and each of the above applications is hereby incorporated by reference as though fully set forth herein.

U.S. application Ser. No. 13/994,541 is a continuation in part of U.S. application Ser. No. 12/898,686, entitled "Devices, Systems and Methods for Treatment of Neuropsychiatric Disorders," filed on Oct. 5, 2010, which claims the benefit of priority under 35 U.S.C. § 119(e) to the following applications: U.S. Application No. 61/248,827, entitled "Devices and Methods for Treatment of Psychiatric Disorders," filed Oct. 5, 2009; U.S. Application No. 61/289,829, entitled "Extracranial Implantable Devices, Systems and Methods for Treatment of Neuropsychiatric Disorders," filed Dec. 23, 2009; U.S. Application No. 61/305,514, entitled "Systems, Devices and Methods for Treatment of Neurological Disorders and Conditions," filed Feb. 17, 2010; and U.S. Application No. 61/354,641, entitled "Extracranial Implantable Devices, Systems and Methods for Treatment of Neurological Disorders," filed Jun. 14, 2010, and each of the above applications is hereby incorporated by reference as though fully set forth herein.

U.S. application Ser. No. 13/994,541 is a continuation in part of U.S. application Ser. No. 12/898,675, entitled "Devices, Systems and Methods for Treatment of Neurological Disorders," filed on Oct. 5, 2010, which claims the benefit of priority under 35 U.S.C. § 119(e) to the following applications: U.S. Application No. 61/248,827, entitled "Devices and Methods for Treatment of Psychiatric Disorders," filed Oct. 5, 2009; U.S. Application No. 61/289,829, entitled "Extracranial Implantable Devices, Systems and Methods for Treatment of Neuropsychiatric Disorders," filed Dec. 23, 2009; U.S. Application No. 61/305,514, entitled "Systems, Devices and Methods for Treatment of Neurological Disorders and Conditions," filed Feb. 17, 2010; and U.S. Application No. 61/354,641, entitled "Extracranial Implantable Devices, Systems and Methods for Treatment of Neurological Disorders," filed Jun. 14, 2010, and each of the above applications is hereby incorporated by reference as though fully set forth herein.

This application is related to copending U.S. application Ser. No. 15/624,640, entitled Extracranial Implantable Devices, Systems and Methods for Treatment of Medical Disorders," filed on Jun. 15, 2017, which is hereby incorporated by reference as though fully set forth herein.

FIELD

The present disclosure generally relates to cutaneous neuromodulation devices and systems and methods of using the same. More specifically, methods, devices, and systems configured for the treatment of medical disorders, such as neuropsychiatric disorders including mood, cognitive and behavioral disorders, heart disease and other cardiac related disorders, and fatigue, via trigeminal nerve stimulation ("TNS") are provided. Devices and systems configured for stimulation of superficial sensory branches of cranial nerves and their methods of application are described.

BACKGROUND

Many medical disorders, including neuropsychiatric disorders, cardiac related disorders and fatigue are traditionally treated with pharmacotherapy and/or psychotherapy. However, a substantial percentage of patients with these and other conditions do not recover despite multiple trials of treatment and there may be significant and long term side effects to the traditional treatment methods.

For example, interventions for fatigue commonly employ medications, particularly psychostimulant medications. Such medications include methylphenidate, amantadine, pemoline, and modafinil (reviewed by Peuckmann et al., Cochrane Database Syst Rev 2010, 11:CD006788). These medications carry potential for side effects, such as blurred vision, depression or anxiety, liver failure, psychosis, suicidal thinking, swelling of the hands/leg/feet, shortness of breath, palpitations, elevated blood pressure, anorexia and addiction.

For some medical disorders, brain stimulation has been a primary treatment alternative, and electroconvulsive therapy (ECT, or "electroshock" therapy) has been the dominant brain stimulation approach since the first part of the 20th century. ECT carries risks of memory and other cognitive side effects, considerable cost, and risks of anesthesia. Two implantable approaches have also been described: deep brain stimulation (DBS), in which electrodes are implanted directly within the brain, and vagus nerve stimulation (VNS) in which stimulating electrodes are implanted on the vagus nerve in the neck. While the U.S. Food and Drug Administration (FDA) have approved systems for deep brain stimulation for the treatment of essential tremor, Parkinson's disease, dystonia and obsessive compulsive disorder, DBS is presently an experimental intervention for other neuropsychiatric conditions. The risks of DBS include infection, hemorrhage, and injury to deep brain structures. In reports of clinical studies with VNS, many of the patients who undergo VNS treatments do not achieve remission, and there is no reliable predictor of good outcomes from the implanted VNS device.

Against this backdrop, the present disclosure is provided.

The information included in this Background section of the specification, including any references cited herein and any description or discussion thereof, is included for technical reference purposes only and is not to be regarded as subject matter by which the scope of the invention is to be bound.

SUMMARY

One aspect of the subject matter of the present disclosure addresses the aforementioned needs by providing a method of treating medical disorders, and systems and devices configured to stimulate the ophthalmic (supraorbital), infraorbital and mentalis branch(es) of the trigeminal nerve to treat medical disorders.

In another aspect of the present disclosure, there is provided an electrode assembly configured for the cutaneous stimulation of the trigeminal nerve.

In yet another aspect of the present disclosure, a method of treating medical disorders using the disclosed electrode assembly is provided.

In one aspect, a system for trigeminal nerve stimulation for treatment of a medical disorder is provided. The system includes a pulse generator and a cutaneous electrode assembly in electrical communication with the pulse generator. In one aspect, the assembly includes a first electrode comprising at least one contact configured for cutaneous placement at a first region of a patient's face, wherein the first electrode is configured to contact a portion of the patient's face overlying the cutaneous distribution of at least one branch of the trigeminal nerve to stimulate the trigeminal nerve to modulate at least one body system for treatment of a medical disorder, wherein the at least one branch of the trigeminal nerve is selected from the group consisting of: ophthalmic nerve, infraorbital nerve, mentalis nerve, supratrochlear nerve, supraorbital nerve, infratrochlear nerve, zygomaticotemporal nerve, zygomaticofacial nerve, zygomaticoorbital nerve, nasal nerve, and auriculotemporal nerve, and wherein the medical disorder is selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders, or a combination thereof.

In one aspect, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. The at least one branch of the trigeminal nerve is an ophthalmic nerve or an infraorbital nerve, wherein the body system is a trigeminal nerve cardiac reflex and wherein stimulation of the ophthalmic nerve or the infraorbital nerve modulates or activates the trigeminal nerve cardiac reflex to treat or prevent a cardiac related disorder. In one aspect, the system of claim 2, wherein the body system is a vagus nerve circuit, and wherein stimulation of the at least one branch of the trigeminal nerve modulates the vagus nerve circuit to treat a cardiac related disorder. In one aspect, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one aspect, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder. In one aspect, the medical disorder is a dementing disorder wherein the body system is a vagus nerve circuit or a trigeminal nerve cardiac reflex, and wherein stimulation of the at least one branch of the trigeminal nerve modulates the vagus nerve circuit or the trigeminal nerve cardiac reflex to treat said medical disorder.

In one aspect, the assembly further comprises a second electrode comprising at least one contact configured for cutaneous placement at a second region of the patient's face, wherein the second electrode is configured to contact a portion of the patient's face overlying the cutaneous distribution of at least one branch of the trigeminal nerve, wherein the at least one branch of the trigeminal nerve is selected from the group consisting of: ophthalmic nerve, infraorbital nerve, supraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, first electrode and the second electrode are configured to contact a portion of the patient's face overlying the cutaneous distribution of a same branch of the trigeminal nerve. In another embodiment, the first electrode and the second electrode are configured to contact a portion of the patient's face overlying the cutaneous distribution of a different branch of the trigeminal nerve. The stimulation may be provided uni- or bilaterally.

In one aspect, the system is configured for minimal current penetration into a brain of a patient. The system may further include a closed loop device configured to provide self-tuning adaptive feedback control to the system. In one embodiment, stimulation of the at least one branch of the trigeminal nerve is determined based on measurement of activity in a brain region to detect an acute biological change. In one embodiment, the at least one branch of the trigeminal nerve is stimulated at a first set of stimulation parameters for a first time period, at a second set of stimulation parameters for a second time period, and at a third set of stimulation parameters for a third time period. In one embodiment, the at least one branch of the trigeminal nerve is stimulated at the first, second and third set of parameters in a cycle at least twice. In one embodiment, the pulse generator is configured to apply electrical signals at a frequency between approximately 1 and 300 Hertz, at a pulse duration between approximately 50 and 500 microseconds, at an output current density of not greater than approximately 10 mA/cm$^2$ and an output charge density of not greater than approximately 10 microCoulomb/cm$^2$ at the cerebral cortex.

In one aspect, a cutaneous electrode assembly for trigeminal nerve stimulation for treatment of a medical disorder is provided. The assembly includes a first electrode comprising at least one contact configured for cutaneous placement at a first region of the patient's face, wherein the first electrode is configured to contact a portion of the patient's face overlying the cutaneous distribution of at least one branch of the trigeminal nerve to stimulate the trigeminal nerve to modulate at least one body system for treatment of a medical disorder, wherein the at least one branch of the trigeminal nerve is selected from the group consisting of: ophthalmic nerve, infraorbital nerve, mentalis nerve, supratrochlear nerve, supraorbital nerve, infratrochlear nerve, zygomaticotemporal nerve, zygomaticofacial nerve, zygomaticoorbital nerve, nasal nerve, and auriculotemporal nerve, and wherein the medical disorder is selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders, or a combination thereof. In one embodiment, the assembly may further include a second electrode comprising at least one contact configured for cutaneous placement at a second region of the patient's face, wherein the second electrode is configured to contact a portion of the patient's face overlying the cutaneous distribution of at least one branch of the trigeminal nerve, wherein the at least one branch of the trigeminal nerve is selected from the group consisting of: ophthalmic nerve, supraorbital nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In some embodiments, the first electrode and the second electrode are configured to contact a portion of the patient's face overlying the cutaneous distribution of a same branch of the trigeminal nerve. In some embodiments, the first electrode and the second electrode are configured to contact a portion of the patient's face overlying the cutaneous distribution of a different branch of the trigeminal nerve. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the body system is a vagus nerve circuit, and wherein stimulation of the at least one branch of the trigeminal nerve modulates the vagus nerve circuit to treat a cardiac related disorder. In one embodiment, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder. In one embodiment, the medical disorder is a dementing disorder wherein the body system is a vagus nerve circuit or a trigeminal nerve cardiac reflex, and wherein stimulation of the at least one branch of the trigeminal nerve modulates the vagus nerve circuit or the trigeminal nerve cardiac reflex to treat said medical disorder. In one embodiment, the assembly produces minimal current penetration into a brain of a patient.

In one aspect, a method for treating a medical disorder by trigeminal nerve stimulation is provided. The method includes contacting a first region of a patient's face with a cutaneous electrode assembly with at least one branch of the trigeminal nerve to stimulate the trigeminal nerve for treatment of a medical disorder and applying electrical signals to the electrode assembly to stimulate the at least one branch of the trigeminal nerve to modulate a system of the patient's body for treatment of a medical disorder. In one embodiment, the cutaneous electrode assembly includes a first electrode comprising at least one contact configured for cutaneous placement at a first region of the patient's face, wherein the first electrode contacts a portion of the patient's face overlying the cutaneous distribution of at least one branch of the trigeminal nerve. The at least one branch of the trigeminal nerve is selected from the group consisting of: ophthalmic nerve, supraorbital nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. The medical disorder is selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders, or a combination thereof. In one embodiment, the method may further include a second electrode comprising at least one contact configured for cutaneous placement at a second region of the patient's face, wherein the second electrode is configured to contact a portion of the patient's face overlying the cutaneous distribution of at least one branch of the trigeminal nerve, wherein the at least one branch of the trigeminal nerve is selected from the group consisting of: ophthalmic nerve, supraorbital nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, step of applying electrical signals comprises applying electrical signals at a frequency between approximately 20 and 300 Hertz, at a current of 0.05 to 5 milliamperes (mA) and at a pulse duration of less than or equal to 500 microseconds. In one embodiment, the step of applying electrical signals comprises applying electrical signals at a frequency between approximately 20 and 300 Hertz, at a pulse duration between approximately 50 and 500 microseconds, at an output current density of not greater than approximately 10 mA/cm$^2$ and a charge density of not greater than approximately 10 microCoulomb/cm$^2$ at the cerebral cortex. In one embodiment, the step of applying electrical signals comprises applying electrical signals at an output current density of not greater than approximately 10 mA/cm$^2$. In one embodiment, the step of applying electrical signals comprises applying electrical signals at an output current density of between approximately 2.5 and 5 mA/cm$^2$. In one embodiment, the step of applying electrical signals comprises applying electrical signals at an output current density of not greater than approximately 7 mA/cm$^2$. In one embodiment, the step of applying electrical signals comprises applying electrical signals at an output current density of not greater than approximately 5 mA/cm$^2$. In one embodiment, the step of applying electrical signals comprises applying electrical signals to minimize current penetration into a brain of a patient. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the body system is a vagus nerve circuit, and wherein stimulation of the at least one branch of the trigeminal nerve modulates the vagus nerve circuit to treat a cardiac related disorder. In one embodiment, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder. In one embodiment, the medical disorder is a dementing disorder wherein the body system is a vagus nerve circuit or a trigeminal nerve cardiac reflex, and wherein stimulation of the at least one branch of the trigeminal nerve modulates the vagus nerve circuit or the trigeminal nerve cardiac reflex to treat said medical disorder.

In one aspect, a kit for trigeminal nerve stimulation for treatment of a medical disorder. In one embodiment, the kit includes an electrode assembly as disclosed elsewhere herein and instructions for applying the electrode assembly to a patient for treatment of a medical disorder, wherein the medical disorder is selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders or a combination thereof. The kit may also include a pulse generator and instructions for applying electrical signals to the electrode assembly for treatment of a medical disorder.

In one aspect, a method for initiation, activation or stimulation of a vagus nerve circuit by trigeminal nerve stimulation for treatment of a medical disorder is provided. The method may include contacting a first region of a patient's face with a cutaneous electrode assembly with at least one branch of the trigeminal nerve to stimulate the trigeminal nerve for treatment of a medical disorder and applying electrical signals to the electrode assembly to stimulate the at least one branch of the trigeminal nerve to modulate the vagus nerve circuit for treatment of a medical disorder which may benefit from vagus nerve stimulation via the trigeminal nerve. The cutaneous electrode assembly includes a first electrode comprising at least one contact configured for cutaneous placement at a first region of the patient's face. The at least one branch of the trigeminal nerve is an ophthalmic nerve or an infraorbital nerve. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, and wherein stimulation of the at least one branch of the trigeminal nerve modulates the vagus nerve circuit to treat said medical disorder. In one embodiment, the medical disorder is a dementing disorder and wherein stimulation of the at least one branch of the trigeminal nerve modulates the vagus nerve circuit to treat said medical disorder.

In one aspect, a behind the ear device for polycranial nerve stimulation for treatment of a medical disorder is provided. The device includes an external ear body including a pulse generator and a battery and an ear canal body including an electrode assembly in electrical communication with the pulse generator. The electrode assembly includes at least one electrode comprising at least one contact configured to contact the cutaneous distribution of at least one branch of the trigeminal nerve at, in or about a patient's ear, and stimulation of the at least one branch of the trigeminal nerve modulates a system in the body to treat a medical disorder. In one embodiment, the at least one branch of the trigeminal nerve is selected from the group consisting of: ophthalmic nerve, infraorbital nerve, supraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, the device further includes a second electrode comprising at least one contact configured for subcutaneous or percutaneous placement at a second region of the patient's face, wherein the second electrode is configured to be implanted in proximity to, adjacent to or in contact with at least one branch of the trigeminal nerve, wherein the at least one branch of the trigeminal nerve is selected from the group consisting of: ophthalmic nerve, infraorbital nerve, supraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, the first electrode and the second electrode are configured for implantation in proximity to, adjacent to or in contact with a same branch of the trigeminal nerve. In one embodiment, the first electrode and the second electrode are configured for implantation in proximity to, adjacent to or in contact with a different branch of the trigeminal nerve. The device produces minimal current penetration into a brain of a patient. The device may further include a closed loop device configured to provide self-tuning adaptive feedback control to the system. Stimulation of the at least one branch of the trigeminal nerve is determined based on measurement of activity in a brain region to detect an acute biological change. In one embodiment, the at least one branch of the trigeminal nerve is stimulated at a first set of stimulation parameters for a first time period, at a second set of stimulation parameters for a second time period, and at a third set of stimulation parameters for a third time period. In one embodiment, the at least one branch of the trigeminal nerve is stimulated at the first, second and third set of parameters in a cycle at least twice. In one embodiment, the pulse generator is configured to apply electrical signals at a frequency between approximately 1 and 300 Hertz, at a pulse duration between approximately 50 and 500 microseconds, at an output current density of not greater than approximately 10 mA/cm$^2$ and an output charge density of not greater than approximately 10 microCoulomb/cm$^2$ at the cerebral cortex. In one embodiment, the pulse generator is configured to apply electrical signals at an output current density of not greater than approximately 10 mA/cm$^2$. In one embodiment, the pulse generator is configured to apply electrical signals at an output current density of between approximately 2.5 and 5 mA/cm$^2$. In one embodiment, the pulse generator is configured to apply electrical signals at an output current density of not greater than approximately 7 mA/cm$^2$. In one embodiment, the pulse generator is configured to apply electrical signals at an output current density of not greater than approximately 5 mA/cm$^2$. In one embodiment, the medical disorder is selected from the group consisting of: neurological disorders, cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of depression, attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders, or a combination thereof. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the at least one branch of the trigeminal nerve is an ophthalmic nerve or an infraorbital nerve, wherein the body system is a trigeminal nerve cardiac reflex and wherein stimulation of the ophthalmic nerve or the infraorbital nerve modulates or activates the trigeminal nerve cardiac reflex to treat or prevent a cardiac related disorder. In one embodiment, the body system is a vagus nerve circuit, and wherein stimulation of the at least one branch of the trigeminal nerve modulates the vagus nerve circuit to treat a cardiac related disorder. In one embodiment, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder. In one embodiment, the medical disorder is a dementing disorder wherein the body system is a vagus nerve circuit or a trigeminal nerve cardiac reflex, and wherein stimulation of the at least one branch of the trigeminal nerve modulates the vagus nerve circuit or the trigeminal nerve cardiac reflex to treat said medical disorder.

In one aspect, a completely in canal device for polycranial nerve stimulation for treatment of a medical disorder. The device includes an elongated body defining a lumen therethrough and further including a pulse generator and a battery housed within the body and an electrode assembly in electrical communication with the pulse generator and located about an outer circumferential surface of the elongated body. The assembly includes at least one electrode comprising at least one contact configured to contact the cutaneous distribution of at least one branch of the trigeminal nerve at, in or about a patient's ear. Stimulation of the at least one branch of the trigeminal nerve modulates a system in the body to treat a medical disorder. In one embodiment, the at least one branch of the trigeminal nerve is selected from the group consisting of: ophthalmic nerve, supraorbital nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, the device further includes a second electrode comprising at least one contact configured for subcutaneous or percutaneous placement at a second region of the patient's face, wherein the second electrode is configured to be implanted in proximity to, adjacent to or in contact with at least one branch of the trigeminal nerve, wherein the at least one branch of the trigeminal nerve is selected from the group consisting of: ophthalmic nerve, supraorbital nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, the first electrode and the second electrode are configured for implantation in proximity to, adjacent to or in contact with a same branch of the trigeminal nerve. In one embodiment, the first electrode and the second electrode are configured for implantation in proximity to, adjacent to or in contact with a different branch of the trigeminal nerve. The device produces minimal current penetration into a brain of a patient. In one embodiment, the device may further include a closed loop device configured to provide self-tuning adaptive feedback control to the system. In one embodiment, stimulation of the at least one branch of the trigeminal nerve is determined based on measurement of activity in a brain region to detect an acute biological change. In one embodiment, the at least one branch of the trigeminal nerve is stimulated at a first set of stimulation parameters for a first time period, at a second set of stimulation parameters for a second time period, and at a third set of stimulation parameters for a third time period. In one embodiment, the at least one branch of the trigeminal nerve is stimulated at the first, second and third set of parameters in a cycle at least twice. In one embodiment, the pulse generator is configured to apply electrical signals at a frequency between approximately 1 and 300 Hertz, at a pulse duration between approximately 50 and 500 microseconds, at an output current density of not greater than approximately 10 mA/cm$^2$ and an output charge density of not greater than approximately 10 microCoulomb/cm$^2$ at the cerebral cortex. In one embodiment, the pulse generator is configured to apply electrical signals at an output current density of not greater than approximately 10 mA/cm$^2$. In one embodiment, the pulse generator is configured to apply electrical signals at an output current density of between approximately 2.5 and 5 mA/cm$^2$. In one embodiment, the pulse generator is configured to apply electrical signals at an output current density of not greater than approximately 7 mA/cm$^2$. In one embodiment, the pulse generator is configured to apply electrical signals at an output current density of not greater than approximately 5 mA/cm$^2$. In one embodiment, the medical disorder is selected from the group consisting of: neurological disorders, cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of depression, attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders, or a combination thereof. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the at least one branch of the trigeminal nerve is an ophthalmic nerve or an infraorbital nerve, wherein the body system is a trigeminal nerve cardiac reflex and wherein stimulation of the ophthalmic nerve or the infraorbital nerve modulates or activates the trigeminal nerve cardiac reflex to treat or prevent a cardiac related disorder. In one embodiment, the body system is a vagus nerve circuit, and wherein stimulation of the at least one branch of the trigeminal nerve modulates the vagus nerve circuit to treat a cardiac related disorder. In one embodiment, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder. In one embodiment, the medical disorder is a dementing disorder wherein the body system is a vagus nerve circuit or a trigeminal nerve cardiac reflex, and wherein stimulation of the at least one branch of the trigeminal nerve modulates the vagus nerve circuit or the trigeminal nerve cardiac reflex to treat said medical disorder.

In one aspect, use of the device for polycranial stimulation as disclosed herein for treatment of a medical disorder is provided. The medical disorder is selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders, or a combination thereof. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the at least one branch of the trigeminal nerve is an ophthalmic nerve or an infraorbital nerve, wherein the body system is a trigeminal nerve cardiac reflex and wherein stimulation of the ophthalmic nerve or the infraorbital nerve modulates or activates the trigeminal nerve cardiac reflex to treat or prevent a cardiac related disorder. In one embodiment, the body system is a vagus nerve circuit, and wherein stimulation of the at least one branch of the trigeminal nerve modulates the vagus nerve circuit to treat a cardiac related disorder. In one embodiment, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder. In one embodiment, the medical disorder is a dementing disorder wherein the body system is a vagus nerve circuit or a trigeminal nerve cardiac reflex, and wherein stimulation of the at least one branch of the trigeminal nerve modulates the vagus nerve circuit or the trigeminal nerve cardiac reflex to treat said medical disorder.

In one aspect use of the system as disclosed elsewhere herein for treatment of a medical disorder is provided. The medical disorder is selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders, or a combination thereof. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the at least one branch of the trigeminal nerve is an ophthalmic nerve or an infraorbital nerve, wherein the body system is a trigeminal nerve cardiac reflex and wherein stimulation of the ophthalmic nerve or the infraorbital nerve modulates or activates the trigeminal nerve cardiac reflex to treat or prevent a cardiac related disorder. In one embodiment, the body system is a vagus nerve circuit, and wherein stimulation of the at least one branch of the trigeminal nerve modulates the vagus nerve circuit to treat a cardiac related disorder. In one embodiment, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder.

In one aspect, use of the assembly as disclosed elsewhere herein for treatment of a medical disorder is provided. The medical disorder is selected from the group consisting of: cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis, sleep/insomnia and a neuropsychiatric disorder selected from the group consisting of attention deficit disorder (ADD), attention deficit hyperactivity disorder (ADHD), autism and autism spectrum disorders (ASD), substance use disorders and related behavioral addictions, eating disorders and obsessive compulsive disorder (OCD), psychotic disorders, dementing disorders, or a combination thereof. In one embodiment, the medical disorder is a cardiac related disorder selected from the group consisting of heart disease, cardiac arrhythmias, myocardial infarction, sudden cardiac death after myocardial infarction, heart failure, cerebral ischemia, sudden infant death syndrome (SIDS), impaired blood flow conditions, atrial fibrillation or sudden death in epilepsy. In one embodiment, the at least one branch of the trigeminal nerve is an ophthalmic nerve or an infraorbital nerve, wherein the body system is a trigeminal nerve cardiac reflex and wherein stimulation of the ophthalmic nerve or the infraorbital nerve modulates or activates the trigeminal nerve cardiac reflex to treat or prevent a cardiac related disorder. In one embodiment, the body system is a vagus nerve circuit, and wherein stimulation of the at least one branch of the trigeminal nerve modulates the vagus nerve circuit to treat a cardiac related disorder. In one embodiment, the medical disorder is fatigue, wherein the body system is a locus coeruleus or a reticular activating system, and wherein stimulation of the at least one branch of the trigeminal nerve modulates the locus coeruleus or modulates the reticular activating system to treat fatigue. In one embodiment, the medical disorder is selected from the group consisting of obesity and other disorders related to weight and feeding, inflammation, disorders of regulation of breathing, disorders of gastrointestinal function, autonomic regulation in menopausal hot flashes, regulation of hemostasis and sleep/insomnia, wherein the body system is a vagus nerve circuit, and wherein stimulation of the at least one branch of the trigeminal nerve modulates the vagus nerve circuit to treat said medical disorder. In one embodiment, the medical disorder is a dementing disorder wherein the body system is a vagus nerve circuit or a trigeminal nerve cardiac reflex, and wherein stimulation of the at least one branch of the trigeminal nerve modulates the vagus nerve circuit or the trigeminal nerve cardiac reflex to treat said medical disorder.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

BRIEF DESCRIPTION OF THE DRAWINGS

The present disclosure, both as to its organization and manner of operation, together with further objects and advantages, may be understood by reference to the following description, taken in connection with the accompanying drawings, in which:

FIGS. 1A and 1B illustrate the location of several branches (nerves) of the trigeminal nerve and the location of the major foramina for the superficial branches of the trigeminal nerve;

FIG. 2 shows average Positron Emission Tomography (PET) scanning data from a pair of adults being treated using aspects of the present disclosure and demonstrating brain regions with increased regional blood flow;

FIG. 3 shows average PET scanning data from a pair of adults being treated using aspects of the present disclosure and demonstrating brain regions with decreased regional blood flow;

FIGS. 8A to 8C-2 illustrate an ear and another embodiment of a system according to aspects of the present disclosure;

FIG. 10 depicts one embodiment of a system for determining patient specific stimulation parameters according to aspects of the present disclosure.

FIG. 12 summarizes one embodiment of current, charge, current density and charge density parameters for a subject exposed to cutaneous stimulation of the supraorbital nerve;

FIGS. 15A-15B illustrates one embodiment of a protocol for mitigating potential accommodation.

DETAILED DESCRIPTION

Figure 1C:
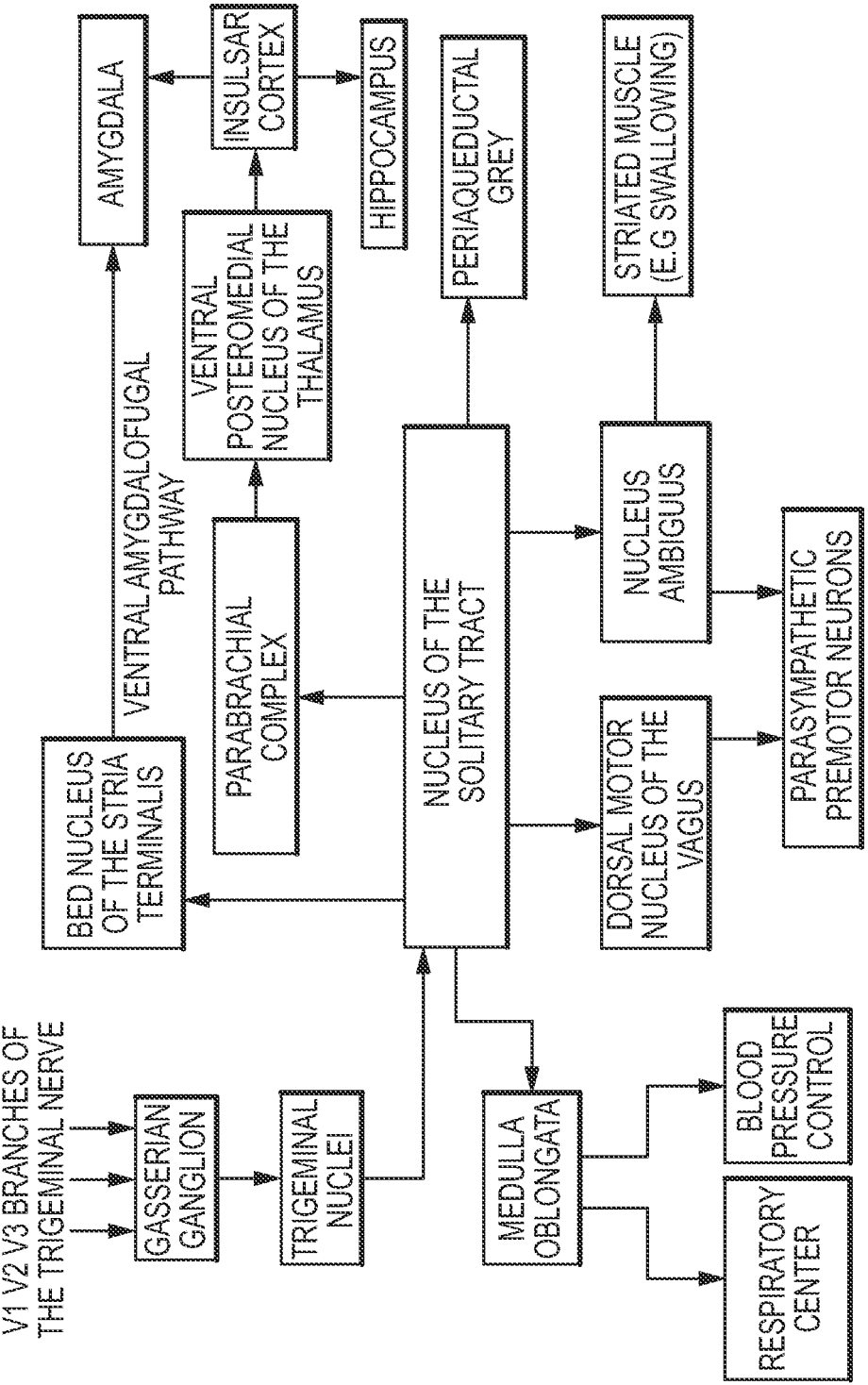
FIG. 1C is a diagram of the principal afferent and efferent projections of the nucleus of the solitary tract.

The present disclosure relates to methods, devices and systems used for the treatment or prevention of various medical disorders via stimulation of the superficial elements of the trigeminal nerve. The medical disorders may include, but are not limited to, neuropsychiatric disorders, neurological disorders, cardiac related disorders, fatigue, tinnitus, obesity, diabetes, dyslipidemia, metabolic syndrome, obstructive sleep apnea, arthritis, cachexia/anorexia, inflammation, asthma, inflammatory bowel disease, atopic dermatitis, sepsis, hepatitis, disorders of regulation of breathing, disorders of gastrointestinal function, gastroesophageal reflux, diarrhea and constipation, dysphagia and other disturbances of swallowing, gastroparesis, functional bowel syndromes, post-operative ileus, dyspepsia, motion sickness, chemotherapy-related nausea and emesis, autonomic regulation in menopausal hot flashes, regulation of hemostasis and sleep/insomnia. The present disclosure also relates to methods, devices and systems used for the treatment of various medical disorders via stimulation of the superficial elements of the trigeminal nerve to modulate the activity of the vagus nerve. More specifically, cutaneous methods of stimulation of the superficial branches of the trigeminal nerve located extracranially in the face, namely the supraorbital, supratrochlear, infraorbital, auriculotemporal, zygomaticotemporal, zygomaticoorbital, zygomaticofacial, infratrochlear, nasal and mentalis nerves (also referred to collectively as the superficial trigeminal nerve) are disclosed herein. Methods for the treatment of various medical disorders, including neuropsychiatric disorders, heart disease and other cardiac related disorders and fatigue, by eTNS (external trigeminal nerve stimulation) are also provided. Systems and devices configured for therapeutic stimulation of the trigeminal nerve or branches thereof, such as the superficial trigeminal nerve, and their methods of application are also described.

As described in more detail herein, when the peripheral branches of the trigeminal nerve are carefully stimulated at frequencies of 1-300 Hz, at pulse durations of 50-500 usec, at output currents generally between 1 and 40 mA, or other parameters as disclosed elsewhere herein, our studies have shown selective activation or inhibition of brain structures involved in the control of various medical disorders as disclosed herein. Thus, measured stimulation of branches of the trigeminal nerve at safe frequencies, pulse durations, and currents can be used to treat these medical disorders.

In addition, the unique anatomy of the trigeminal nerve, and its direct and indirect connections with key areas of the brainstem (including pons and medulla) and other structures of the nervous system involved with the vagus nerve may allow the use of cutaneous stimulation of the TNS as a method to modulate the vagus nerve to treat various medical disorders, including, but not limited to, obesity and other disorders related to weight and feeding, inflammation, disorders of regulation of breathing, disorders of gastrointestinal function, autonomic regulation in menopausal hot flashes, regulation of hemostasis and sleep/insomnia. Because the trigeminal nerve projects to the dorsal motor nucleus of the vagus nerve, trigeminal nerve stimulation can be used as a safe and non-invasive method to deliver stimulation of vagus nerve circuits in the brain, without implanting a vagus nerve stimulator, and without direct stimulation of the cervical vagus nerve or its branches. The methods, systems and devices described herein are noninvasive.

Some brain stimulation methods aim to generate currents in large volumes of the cortex and treat the brain as a bulk conductor, for example, ECT (electroconvulsive therapy) at the whole-lobe level and rTMS (repetitive transcranial magnetic stimulation) at the large regional level (i.e. dorsolateral prefrontal cortex). Additionally, deep brain stimulation is generally predicated on stimulation of small but regional volumes that lead to discharges in a very large number of cells. The systems, devices and methods of the present disclosure send minimal, if any, current into the brain; instead, signals are sent into the brain in order to modify the activity of relevant neuroanatomical structures. Without wishing to be bound by any particular theory, the electrical pulses generate signals in the cutaneous branches of the trigeminal nerve and the electric fields are generally confined to the skin tissue and there is minimal, if any, leakage into the brain. These electrical pulses traveling through the trigeminal pathways in the brain trigger a cascade of change in neuronal signaling events that involve very limited and precise recruitment of specific networks of neurons identified on figures attached that effect long lasting effects capable to modulate the diseases herein claimed. The neuroanatomic pathways allow targeted modulation of activity of the trigeminal nerve and the vagus nerve and further networks. Thus, the systems, devices and methods as disclosed herein utilize the brain's existing infrastructure to transmit signals to the targets of interest. In the context of this disclosure, minimal current penetration means (1) a charge density of approximately 0 uC/cm$^2$ at the cerebral cortex, or (2) calculated, measured, or modeled charge densities below the following thresholds at the cerebral cortex: (a) at currents, charge densities, or charge per phase not likely to cause direct activation of pyramidal neurons and axons; and (b) to prevent brain injury, a charge density of less than 10 uC/cm$^2$ in one embodiment, and, in other embodiments, a charge density of less than 1.0 uC/cm$^2$ and in some embodiments, a charge density of less than 0.001 to 0.1 uC/cm$^2$, and at combinations of charge density and charge per phase not known to cause brain injury. In some embodiments, a lower charge density may be used when the central nervous system of an individual patient is sufficiently sensitive to lower levels of stimulation that the lower level will still permit clinical benefit to accrue.

The following description is provided to enable any person skilled in the art to make and use the subject matter of this disclosure. Various modifications, however, will remain readily apparent to those skilled in the art, since the general principles of the disclosed subject matter have been defined herein specifically to describe: (1) methods of treating medical disorders by trigeminal nerve stimulation, (2) a system and an electrode assembly configured for cutaneous trigeminal nerve stimulation; and (3) methods of treating medical disorders using such system and electrode assembly.

To provide context for the disclosure, a brief description of the trigeminal nerve and its connection to the vagus nerve is now provided. With reference to FIGS. 1A and 1B, the trigeminal nerve is the largest cranial nerve, and has extensive connections with brainstem and other brain structures. It is the fifth (of twelve) cranial nerves, and is often designated as Cranial Nerve V (CN V). The trigeminal nerve has three major sensory branches over the face, all of which are bilateral, and highly accessible. The supraorbital nerve, or ophthalmic nerve, is frequently referred to as the $V_1$ division. The infraorbital branch, or maxillary nerve, is commonly referred to as the $V_2$ division. The mandibular nerve (also known as the mentalis branch) is referred to as the $V_3$ division. The supraorbital nerve supplies sensory information about pain, temperature, and light touch to the skin of the forehead, the upper eyelid, the anterior part of the nose, and the eye. The infraorbital branch supplies sensory information about pain, temperature, and light touch sensation to the lower eyelid, cheek, and upper lip. The mentalis branch supplies similar sensory modalities to the skin of the lower face (e.g. jaw and tongue) and lips.

These branches exit the skull through three foramina, as shown in FIGS. 1A and 1B. The supraorbital nerve or ophthalmic nerve exits at foramen 1 (the supraorbital foramen or notch), approximately 2.1-2.6 cm from the nasal midline (in adults), and is located immediately above the orbital ridge that is located below the eyebrow. The infraorbital branch or maxillary nerve exits at foramen 2 (the infraorbital foramen), approximately 2.4-3.0 cm from the nasal midline (in adults), and the mentalis nerve exits at foramen 3 (the mentalis foramen), approximately 2.0-2.3 cm from the nasal midline (in adults). The nasal nerve is a division of the ophthalmic nerve. Other sensory branches, including the zygomaticofacial, zygomaticoorbital, zygomaticotemporal, and auriculotemporal, arise from other foramina.

Fibers from the three major branches join together to form the trigeminal ganglion (also called the Gasserian ganglion). From there, fibers ascend into the brainstem at the level of the pons to synapse with the main sensory nucleus of the pons, the mesencephalic nucleus of V, and the spinal nucleus and tract of V. Pain fibers descend in the spinal nucleus and tract of V, and then ascend to the ventral posterior medial nucleus (VPM) of the thalamus. Light touch sensory fibers are large myelinated fibers, which ascend to the ventral posterior lateral (VPL) nucleus of the thalamus. Afferent sensory fibers project from the trigeminal nuclei to the thalamus and the cerebral cortex.

The trigeminal nucleus has reciprocal projections to the nucleus tractus solitarius or nucleus of the solitary tract (NTS), the locus coeruleus, the cerebral cortex and the vagus nerve. The NTS receives afferents from the vagus nerve and trigeminal nerve. As can be understood from FIG. 1C, the NTS integrates input from multiple sources, and projects to structures in the brainstem and forebrain, including the locus coeruleus. FIG. 1C, which is a modified reproduction from Ruffoli, R. et al, is a diagram of the principal afferent and efferent projections of the nucleus of the solitary tract (see Ruffoli, R. et al., The chemical neuroanatomy of vagus nerve stimulation, J. Chem. Neuroanat. (2011), doi:10.1016/j.jchemneu.2010.12.002). The NTS connects to the medulla oblongata to control blood pressure and the respiratory center. The NTS projects to the dorsal motor nucleus of the vagus and the nucleus ambiguus parasympathetic pregangliar neurons and influences cardiac activity. The NTS connection to the nucleus ambiguus results in innervation the striate muscles involved in swallowing and heart rate. The NTS also projects to the periaqueductal grey and visceral nuclei of the spinal cord, mediating visceral sensation. Efferent pathways reach the BNTS, from which they are relayed to the amygdala. Inputs from NTS reach the cerebral cortex via the parabrachial complex and the VPM. (see generally, Ruffoli et al. 2011). Additionally it also has connections to other nuclei in the brain, for example the dorsal cochlear nucleus which affects tinnitus. (Soleymani et al Surgical approaches to tinnitus treatment: A review and novel approaches, Surg Neurol Int 2011, 2:154.)

The locus coeruleus is a paired nuclear structure in the dorsal pons, and is located just beneath the floor of the fourth ventricle. The locus coeruleus has extensive axonal projections to a broad number of brainstem, sub-cortical and cortical structures, and is an important part of the reticular activating system. The locus coeruleus is a core part of the brainstem noradrenergic pathway, and produces the neurotransmitter norepinephrine. Norepinephrine plays a key role in attention, alertness, blood pressure and heart rate regulation, and mood.

Figure 1D:
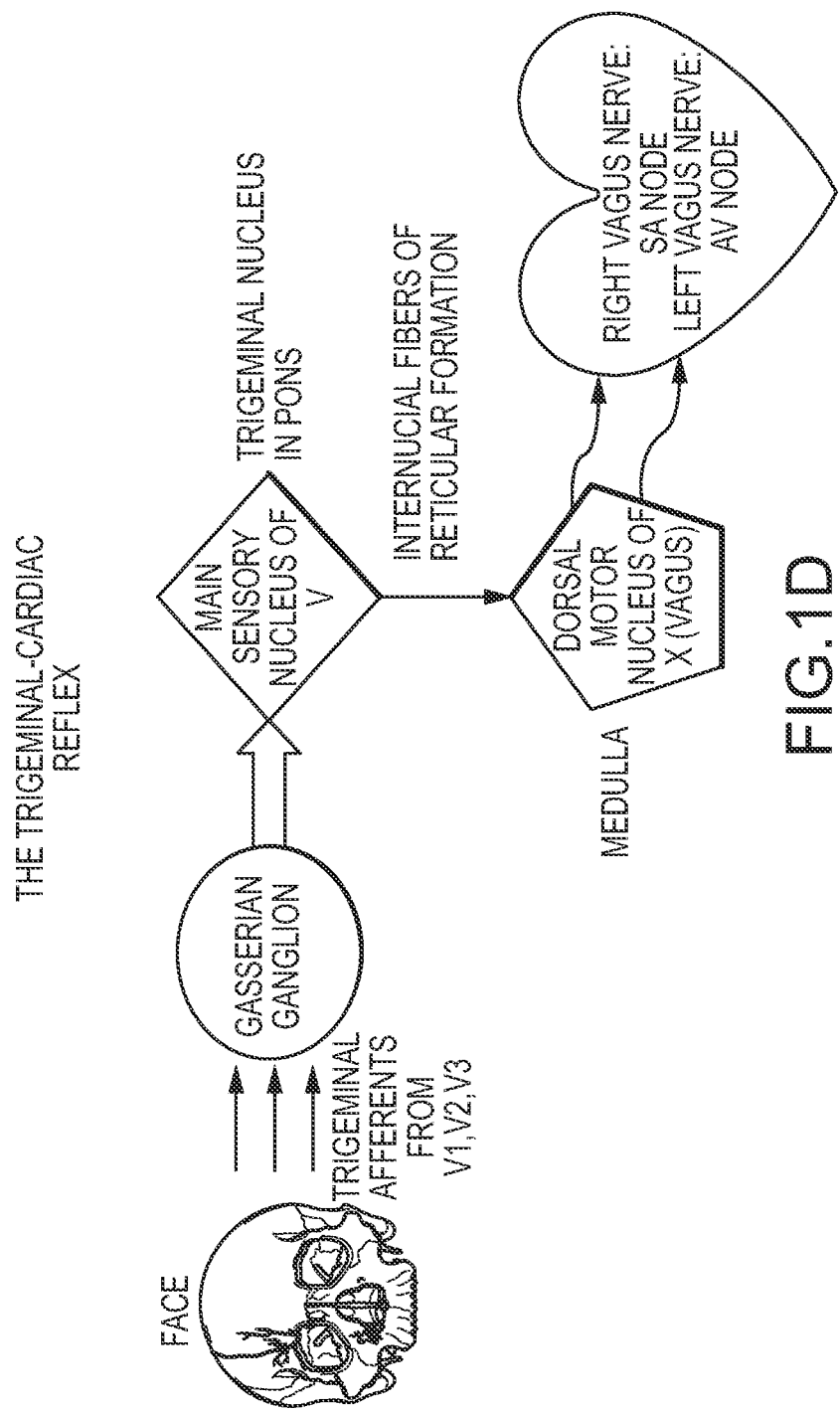
FIG. 1D illustrates the connection between the trigeminal nerve and the vagus nerve.

Turning now to FIG. 1D, and with continued reference to FIG. 1C, the trigeminal nerve is also connected to the vagus nerve. Afferent sensory fibers from the three trigeminal divisions ($V_1$, $V_2$, $V_3$) project to the Gasserian ganglion, synapse there, and then project to the main sensory nucleus of the trigeminal nerve. Axons from the sensory nucleus then project via the Internucial fibers of the Reticular Formation to the Dorsal Motor Nucleus of the vagus nerve (the tenth cranial nerve, also designated as Cranial Nerve X or CN X) in the dorsal medulla. Efferent fibers from each right and left vagus nerve nuclei then form the main trunk of the vagus nerve. Thus, because of the underlying anatomy, and projections from the trigeminal nerve nuclei to the vagus nerve nuclei, stimulation of the peripheral branches of the trigeminal nerve can be utilized to activate the vagus nerve. This results in vagus nerve stimulation from peripheral trigeminal nerve stimulation. Since trigeminal nerve activation of the vagus nerve can be performed in a non-invasive fashion, activating the vagus nerve via activation of the peripheral branches of the trigeminal nerve has advantages over direct vagus nerve stimulation, which is currently performed using a surgically implantable electrode and pulse generator attached to the vagus nerve. This engagement of the vagus nerve via trigeminal nerve stimulation has direct clinical application to treating medical disorders as disclosed herein, which may benefit from increased vagus nerve or parasympathetic activity. Without wishing to be bound by any particular theory, the systems and methods disclosed herein for stimulation of the trigeminal nerve to activate the vagus nerve may also be relevant for neurological, psychiatric, cardiac or other medical disorders where vagus nerve stimulation is activated or provided via stimulation of the trigeminal nerve and its branches. Thus, trigeminal nerve stimulation is a potential method to initiate, activate and provide stimulation of vagus nerve circuits.

In one aspect, the disclosure describes the application of trigeminal nerve stimulation to treat medical disorders including: neuropsychiatric and neurological disorders, cardiac related disorders, fatigue, tinnitus and other medical disorders. Stimulation of peripheral and cutaneous branches of the trigeminal nerve in the face, ear or scalp can be applied and stimulated at safe frequencies, pulse durations and amplitudes. Such treatment is advantageous over the currently used pharmacological approaches which often have undesirable side effects or lack specificity in their actions.

In another aspect, the disclosure describes the application of trigeminal nerve stimulation as a method to stimulate the vagus nerve to treat medical disorders including: neuropsychiatric and neurological disorders, cardiac related disorders, fatigue, tinnitus, obesity and other disorders related to weight and feeding, inflammation, disorders of regulation of breathing, disorders of gastrointestinal function, autonomic regulation in menopausal hot flashes, regulation of hemostasis and insomnia and disturbances of sleep. Since the trigeminal nerve projects to the dorsal motor nucleus of the vagus nerve, trigeminal nerve stimulation can be used as a safe and non-invasive method to deliver stimulation of vagus nerve circuits, without implanting a vagus nerve stimulator, and without direct stimulation of the cervical vagus nerve or its branches.

Psychiatric and Neuropsychiatric Disorders

The unique anatomy of the trigeminal nerve, and its direct and indirect connections with key areas of the brainstem, thalamus, amygdala, insula, anterior cingulate and other cortical and subcortical areas involved with sensory processing, attention, emotion, cognition, and autonomic function, may allow the use of external stimulation for a variety of neuropsychiatric conditions in which stimulation may be desirable.

The present disclosure relates to methods, devices and systems used for the treatment of mood, anxiety, post traumatic stress disorder, neuropsychiatric disorders, including mood (such as depression), anxiety (such as post-traumatic stress disorder) and psychotic disorders (e.g. schizophrenia), and cognitive and behavioral disorders as well as attention deficit disorder (ADD), attention deficit hyperactivity disorder (ADHD), autism and autism spectrum disorders (ASD), substance use disorders and related behavioral addictions, eating disorders and obsessive compulsive disorder (OCD) (collectively, neuropsychiatric disorders) via stimulation of the superficial elements of the trigeminal nerve ("TNS"). More specifically, cutaneous methods of stimulation of the superficial branches of the trigeminal nerve located extracranially in the face, namely the supraorbital, supratrochlear, infraorbital, auriculotemporal, zygomaticotemporal, zygomaticoorbital, zygomaticofacial, infratrochlear, nasal and mentalis nerves (also referred to collectively as the superficial trigeminal nerve) are disclosed herein. Methods for the treatment of mood and other neuropsychiatric disorders including but not limited to attention deficit disorder (ADD), attention deficit hyperactivity disorder (ADHD), autism and autism spectrum disorders (ASD), substance use disorders and related behavioral addictions, eating disorders, psychotic disorders, and obsessive compulsive disorder (OCD) by eTNS (external trigeminal nerve stimulation) are also provided. Systems and devices configured for therapeutic stimulation of the trigeminal nerve or branches thereof, such as the superficial trigeminal nerve, and their methods of application are also described.

While not wishing to be bound by any particular theory, in certain embodiments, the connections between the trigeminal nerve and the locus coeruleus, thalamus, amygdala, anterior cingulate, and other central nervous system structures as described above may be relevant to a potential role of the trigeminal nerve in neuropsychiatric disorders, including mood (such as depression), anxiety (such as post-traumatic stress disorder), psychosis (such as schizophrenia), and other cognitive and behavioral disorders. Thus, cutaneous stimulation of the trigeminal nerve can be effective in the treatment of these neuropsychiatric disorders.

The PET scan data of FIGS. 2 and 3 support the use of TNS in humans for treatment of neuropsychiatric disorders, namely depression and anxiety disorders, such as PTSD. As discussed in more detail below, the PET scans show sections of the brain with increased activity (FIG. 3) and decreased activity (FIG. 3). For example, increased activity is seen in the medial prefrontal cortex, including the ACC, (see FIG. 2, which is indicated by the color (darker) pixels in panels (a) and (b)). Increased activity of the dorsolateral prefrontal cortex is also shown in FIG. 2, panel c as the large colored (darker) area in the lower right of the image. Increased activity is also seen in the orbitofrontal cortex, as shown in FIG. 2 in panel b as the small region at the lower left of the image. Modulation of the activity in these and other brain structures, which are shown to be affected by trigeminal nerve stimulation, assist in improving the symptoms of depression and anxiety disorders, such as PTSD, and other medical disorders disclosed elsewhere herein.

Other medical disorders may also be treated according to aspects of the present disclosure, as indicated by PET scan data (see FIGS. 2 and 3) obtained from two adults that were treated according to aspects of the present disclosure. FIG. 2 shows an increased activity in the medial prefrontal cortex, including the ACC, which is indicated by the color (darker) pixels in panels (a) and (b). Increased activity in the superior frontal gyrus is seen in panels (c) and (d), on the upper (superior) surface of the brain, while the increased activity in the lateral frontal cortex is seen most clearly in panel (c), in the lower-right part of that image. FIG. 3 shows a decreased activity in the superior parietal cortex which is seen in panel (a) as the colored (darker) region in the upper left of that image, panel (b) as the colored (darker) pixels in the upper right, panel (c) as the upper two regions of color (darker) pixels, and in panel (d) as the colored (darker)

region near the top of the brain. The decreased activity in the cortex is consistent with the antiepileptic effects of eTNS. The temporal-occipital cortex is seen in panel (c) as the largest colored (darker) region, and in panel (d) as the middle of the three colored areas. Modulation of the activity in these and other brain structures, which are shown to be affected by trigeminal nerve stimulation, assist in improving the symptoms of attention deficit disorder (ADD), attention deficit hyperactivity disorder (ADHD), autism and autism spectrum disorders (ASD), substance use disorders and related behavioral addictions, eating disorders, psychosis, and obsessive compulsive disorder (OCD).

Attention Deficit Disorder (ADD), Attention Deficit Hyperactivity Disorder (ADHD), Autism, and Autism Spectrum Disorders (ASD)

Without wishing to be bound by any particular theory, neuroimaging studies have implicated dysfunction in several brain regions in the pathophysiology and treatment response of these disorders, which commonly arise early in life. As defined by the American Psychiatric Association's Diagnostic and Statistical Manual of Mental Disorders (American Psychiatric Association, 4th edition, 2000), attention deficit/hyperactivity disorder (ADHD) is marked by symptoms of inattention, hyperactivity, and impulsivity, while the diagnosis of ADD (now formally ADHD/inattentive type) lacks the hyperactivity and impulsivity features. In ADD and ADHD, prior research has found abnormalities in multiple regions, including the anterior cingulate cortex (ACC) and parietal cortex (e.g., Makris et al., 2010, *J Atten Disord* 13(4):407-13; Dickstein S G, et al. 2006 *J Child Psychol Psychiatry.* 47(10):1051-62). As defined by the American Psychiatric Association's Diagnostic and Statistical Manual of Mental Disorders (American Psychiatric Association, 4th edition, 2000), autism (also termed autistic disorder) is characterized by pervasive deficits in development in areas such as reciprocal social interaction skills, communication skills, or the presence of stereotyped behavior, interests, and activities. ASD includes related diagnoses such as Asperger's Syndrome, in which most features are present but not a delay in language development. Regions implicated in Autism and ASD include ACC, frontal cortex, temporal cortex, and parietal cortex (e.g., Hall G B, Szechtman H, Nahmias C. 2003. *Am J Psychiatry.* 160(8):1439-41; McAlonan G M, et al. 2005. *Brain.* 128(Pt 2):268-76; Cherkasova M V, Hechtman L. 2009. *Can J Psychiatry.* 54(10):651-64; Konrad K, et al. 2006. *Biol Psychiatry.* 59(7):643-51.)

Regional activation with trigeminal nerve stimulation was examined using Positron Emission Tomographic (PET) scanning in two adults. FIG. 2 shows areas of increased blood flow emerging after acute exposure to TNS; regions of statistically significant differences between epochs of exposure and non-exposure are indicated. Areas that exhibited significant increases in regional activation with TNS included the medial prefrontal cortex (including ACC), the superior frontal gyrus, the lateral frontal cortex, and the middle temporal gyms. FIG. 3 shows areas of decreased blood flow under the same conditions; significant regional inhibition was found in the superior parietal cortex temporal-occipital cortex. Modulation of the activity in these and other brain structures, which are shown to be affected by trigeminal nerve stimulation, could assist in improving the cognitive and behavioral symptoms of ADD, ADHD, Autism, and ASD.

Substance Use Disorders and Related Behavioral Addictions.

Disorders of substance abuse and dependence (e.g., of alcohol, cocaine, marijuana, tobacco, etc.) are defined as disorders of maladaptive patterns of behavior, as defined by the American Psychiatric Association's Diagnostic and Statistical Manual of Mental Disorders (American Psychiatric Association, 4th edition, 2000), and include criteria such as tolerance to a substance, withdrawal upon discontinuing use, an inability to cut down or control use of the substance, and giving up important social, occupational, or recreational activities because of using the substance. Behavioral addictions (e.g., internet addiction, sexual addiction, pathological gambling) share clinical features similar to those maladaptive patterns of behavior which are centered on chemical substances, but with engagement in the problem behavior rather than consuming a substance. Without wishing to be bound by any particular theory, neuroimaging studies have implicated dysfunction in several brain regions in the pathophysiology and treatment response in these disorders, particularly the anterior cingulate cortex (ACC), frontal cortex, and parietal cortex (Goldstein R Z and Volkow N D. 2011. *Neuropsychopharmacology.* 36(1):366-7; Vollstadt-Klein S, et al., 2010. *Alcohol Clin Exp Res.* 34(5):771-6; Fineberg N A, et al., 2010. *Neuropsychopharmacology.* 35(3):591-604; Dannon P N, et al. 2011. *Brain Imaging Behav.* 5(1):45-51, published online Nov. 16, 2010). As noted above, PET scan data showed acute alterations in regional brain activity with exposure to TNS; these areas include those regions implicated in substance use disorders and in behavioral addictions. Modulation of activity in these and other brain structures, which are shown to be affected by trigeminal nerve stimulation, could assist in improving the cognitive and behavioral symptoms of substance use and behavioral addiction disorders.

Eating Disorders.

Eating disorders include illnesses such as anorexia nervosa, bulimia nervosa, and other disorders related to eating (e.g., binge eating), as defined by the American Psychiatric Association's Diagnostic and Statistical Manual of Mental Disorders (American Psychiatric Association, 4th edition, 2000); in all, problems center disorders of eating behaviors, predominantly related to perceived body image, consumption of food, and/or expenditure of energy (e.g. excessive exercise); these behaviors can lead to abnormal weight and potentially life-threatening states of malnutrition or metabolic abnormalities. Without wishing to be bound by any particular theory, neuroimaging studies have implicated several brain regions in these disorders, including ACC and prefrontal cortex, and abnormal afferent inputs to the brain via the vagus nerve (Joos A, et al., 2010 *Psychiatry Res.* 182(2):146-51; Miyake et al., 2010. *Psychiatry Res.* 181(3): 183-92; Faris P L, et al., 2006 *J Affect Disord.* 92(1):79-90.) As noted above, PET scan data showed acute alterations in regional brain activity with exposure to TNS; these areas include those regions implicated in eating disorders. Modulation of activity in these and other brain structures, which are shown to be affected by trigeminal nerve stimulation, could assist in improving the symptoms of eating disorders.

Obsessive Compulsive Disorder.

Obsessive Compulsive Disorder (OCD), as defined by the American Psychiatric Association's Diagnostic and Statistical Manual of Mental Disorders (American Psychiatric Association, 4th edition, 2000), is marked by the presence of obsessive, ruminative thoughts (e.g. fears of contamination with dirt or germs), and compulsive behaviors (e.g., ritualized handwashing). Without wishing to be bound by any particular theory, neuroimaging studies have implicated several brain regions in these disorders, including ACC, caudate nucleus, striatum, prefrontal cortex, and parietal cortex (e.g., Huyser C, et al., 2010. *J Am Acad Child Adolesc Psychiatry.* 49(12):1238-48; Matsumoto R, et al., 2010. *Psychiatry Clin Neurosci.* 64(5):541-7). As noted above, PET scan data showed acute alterations in regional brain activity with exposure to TNS; these areas include some of those regions implicated in OCD. Modulation of activity in these and other brain structures, which are shown to be affected by trigeminal nerve stimulation, could assist in improving the symptoms of OCD Surprisingly, our data show that TNS affects heart rate and cardiac function, physiologic measures under vagal control. (Pop et al, Epilepsy & Behavior 2011 and FIG. 13). Trigeminal nerve stimulation thus provides non-invasive modulation of, and access to, the autonomic nervous system, including the parasympathetic pathways of the vagus system. While not wishing to be bound by any particular theory, some clinical effects of TNS may be mediated by trigeminal modulation of the vagus nerve system, while other clinical effects of TNS are independent of vagal circuit modulation, and yet others may reflect a combination of direct trigeminal effects and indirect effects mediated by the vagus nerve system. For example, with regard to the antiepileptic effects of TNS, our human PET data show decreased activity in cortical areas related to seizure initiation, propagation and inhibition, which are independent of known vagal inputs. (FIGS. 2 and 3) There is also data from pre-clinical animal models showing that TNS inhibits neocortical neuronal firing via a direct mechanism independent of vagal synapses as evidenced by the rapid onset of the effect. (Fanselow et al, Abstract 2.220, Annual Meeting of the American Epilepsy Society, San Antonio, Tex. 2010) Surprisingly, the clinical response to TNS can arise directly from trigeminal effects independent of the vagus nerve or mediated through, and in combination with, the vagus nerve and its circuits. In addition, since the trigeminal nerve projects to the dorsal motor nucleus of the vagus nerve, trigeminal nerve stimulation can be used as a safe and non-invasive method to deliver stimulation to vagus nerve circuits, without implanting a vagus nerve stimulator, and without direct stimulation of the cervical vagus nerve or its branches. Stimulation of the vagus nerve circuits via trigeminal nerve stimulation reduces seizure activity. As described elsewhere herein, our data demonstrates a 4% reduction in heart rate via acute stimulation of the trigeminal nerve (e.g. modulation of the vagus nerve via trigeminal nerve stimulation activates the trigeminal-cardiac reflex.)

Psychotic Disorders Including Schizophrenia

Without wishing to be bound by any particular theory, the cause(s) of psychotic illnesses, such as schizophrenia, remain to be fully understood, but findings from neuroimaging studies implicate specific brain regions in the development of symptoms, such as hallucinations, delusions, impaired reality testing, and disorganized thought processes. Areas such as the temporo-parietal cortex, bilateral prefrontal cortical regions, and the anterior cingulate cortex have been linked to psychosis (e.g., Fusar-Poli P, et al. Neuroanatomy of vulnerability to psychosis: a voxel-based meta-analysis. Neurosci Biobehav Rev. 2011. 35(5):1175-85). Data from our PET scan study (above) showed acute alterations in regional brain activity with exposure to TNS; these areas include those regions implicated in schizophrenia and other psychotic disorders. Modulation of activity in these and other brain structures, which are shown to be affected by trigeminal nerve stimulation, could assist in improving the symptoms of schizophrenia and other psychotic disorders and can be treated according to the systems, devices and methods disclosed herein.

Dementing Disorders Including Alzheimer's Disease

Dementing disorders are marked by cognitive impairments, particularly problems with memory and behavior, and include specific illnesses such as Alzheimer's Disease, Vacular Dementia, and Fronto-temporal Dementia. Multiple cortical and subcortical structures may be disrupted in these disorders. Activity in many of these structures may be modulated by inputs from the locus coeruleus (e.g., Samuels E R, Szabadi E. Functional neuroanatomy of the noradrenergic locus coeruleus: its roles in the regulation of arousal and autonomic function part II: physiological and pharmacological manipulations and pathological alterations of locus coeruleus activity in humans. *Curr Neuropharmacol.* 2008 Sep.; 6(3):254-85). Without wishing to be bound by any particular theory, the circuitry of the trigeminal nerve system is able to send signals to the locus coeruleus, so that TNS-driven modulation of the locus coeruleus impacts these disorders. In addition, stimulation of the vagus nerve has been used to treat symptoms of Alzheimer's disease (e.g., Merrill C A, et al. Vagus nerve stimulation in patients with Alzheimer's disease: Additional follow-up results of a pilot study through 1 year. *J Clin Psychiatry.* 2006. 67(8):1171-8). Modulation of activity in these and other brain structures can be used to treat the medical disorders as disclosed herein according to the systems, devices and methods disclosed herein.

Heart Disease and Other Cardiac Related Disorders

The trigeminal-cardiac reflex or trigemino-cardiac reflex (TCR) is a central nervous system reflex which functions to increase cerebral blood flow and provide neuroprotection when the brain is exposed to hypoxia or diminished blood flow. An exaggerated form of this reflex can occur during neurosurgical, eye, or sinus procedures as the result of traction or manipulation of branches of the trigeminal nerve. Under these conditions, significant reductions in heart rate, heart block, or complete asystole have been reported. (See generally, Schaller et al., J Neurosurgical Anesthesiology, 2009; 21:187-95)

In the past, the TCR had been used to clinical benefit to reduce the heart rate in the setting of life threatening or severe arrhythmias. For example, physicians have utilized the TCR to slow the heart rate through application of ocular pressure during supraventricular tachycardia. This primitive, poorly-controlled technique could be associated with adverse events such as excessive reductions in heart rate, and with the advent of improved drug therapy for arrhythmias, this technique is no longer in common use.

Reflex bradycardia, hypotension and occasionally asystole as a result of the TCR have been reported for many years as a complication encountered during ophthalmologic and neurosurgical procedures. These adverse events arise from stimulation of the TCR in an uncontrolled and nonspecific fashion. Through stimulation of the peripheral branches of the trigeminal nerve, employing particular frequencies, pulse durations and current outputs, the TCR can be activated (or utilized) in a controlled fashion to provide therapeutic ends including protection of the brain and the heart, as well as modulation of the activity of these organs.

The unique anatomy of the trigeminal nerve, and its direct and indirect connections with key areas of the brainstem (including pons and medulla) and other structures of the nervous system involved with the vagus nerve and/or the TCR may allow the use of cutaneous stimulation of the TNS as a method to activate the TCR to prevent and/or treat cardiac related disorders, including, but not limited to, preventing and/or treating cardiac arrhythmias, arrhythmias and sudden cardiac death after myocardial infarction, heart failure, SIDS, cerebral ischemia, impaired blood flow conditions, atrial fibrillation and reducing the risk of sudden death in epilepsy. In addition, since the trigeminal nerve projects to the dorsal motor nucleus of the vagus nerve, trigeminal nerve stimulation can be used as a safe and non-invasive method to deliver stimulation of vagus nerve circuits, without implanting a vagus nerve stimulator, and without direct stimulation of the cervical vagus nerve or its branches.

Turning back to FIG. 1D, and with reference to FIG. 1C, the TCR is the result of connections between divisions of the trigeminal nerve, the internuncial fibers of the reticular formation and the vagus nerve nuclei, including the motor nucleus of the vagus nerve. Projections from the vagus nerve innervate the heart. Stimulation of this pathway and reflex arc can cause selective reduction in heart rate. Afferent sensory fibers from the three trigeminal divisions ($V_1$, $V_2$, $V_3$) project to the Gasserian ganglion, synapse there, and then project to the main sensory nucleus of the trigeminal nerve. Axons from the sensory nucleus then project via the Internucial fibers of the Reticular Formation to the Dorsal Motor Nucleus of the vagus nerve (Cranial Nerve X) in the dorsal medulla. Efferent fibers from each right and left vagus nerve nuclei then form the main trunk of the vagus nerve. Branches from the cervical portion of the vagus nerve then form the left and right cardiac nerves (both superior and inferior branches). These branches innervate the heart: the left vagus nerve projects primarily to the Atrioventricular Node (AV node), and the right vagus nerve projects to the Sinoatrial Node (SA node). Via these branches, the vagus nerve acts to reduce the heart rate, modify conduction, and stabilize the myocardium in response to stress and ischemia. The TCR reflex is protective. It lowers heart rate in the presence of ischemia by protecting the heart from fast cardiac arrhythmias (tachyarrhythmias), and by increasing cerebral blood flow in the setting of hypoxia. Without wishing to be bound by any particular theory, stimulation of the trigeminal nerve, particularly via the ophthalmic, supraorbital, supratrochlear or infraorbital branches, can be performed safely to modulate the TCR and prevent and/or treat heart disease and related cardiac disorders. Proper, controlled activation of this reflex arc, using a range of parameters, through cutaneous trigeminal nerve stimulation, can be used to protect the heart by reducing heart rate, reducing heart rate variability, and preventing or treating tachyarrhythmias and preventing sudden cardiac death. When properly applied, utilization of this reflex arc through trigeminal nerve stimulation can also protect the brain by conserving oxygen and reducing the adverse effects of ischemia and seizures. Conditions benefiting by measured activation of the TCR include heart failure, SIDS, supraventricular and ventricular tachycardia, acute myocardial infarction, impaired blood flow conditions, atrial fibrillation prevention of sudden cardiac death and sudden death in epilepsy, and neuroprotection.

As a result, because of the anatomy underlying the TCR, and projections from the trigeminal nerve nuclei to the vagus nerve nuclei, stimulation of the peripheral branches of the trigeminal nerve can be utilized to activate the vagus nerve. This results in vagus nerve stimulation from peripheral trigeminal nerve stimulation. Since trigeminal nerve activation of the vagus nerve can be performed in non-invasive fashion, activating the vagus nerve via activation of the peripheral branches of the trigeminal nerve has surprising advantages over direct vagus nerve stimulation, which is currently performed using a surgically implantable electrode and pulse generator attached to the vagus nerve. This engagement of the vagus nerve via trigeminal nerve stimulation has direct clinical application to preventing and/or treating and/or preventing cardiac related disorders, (and other disorders as described elsewhere herein) which may benefit from increased vagus nerve or parasympathetic activity. Without wishing to be bound by any particular theory, the system disclosed herein for stimulation of the trigeminal nerve to activate the TCR may also be relevant for other neurological, psychiatric, cardiac or other disorders where vagus nerve stimulation is activated or provided via stimulation of the trigeminal nerve and its branches. Since the TCR reflects vagus nerve activation via stimulation of the trigeminal nerve, trigeminal nerve stimulation is a potential method to initiate, activate and provide vagus nerve stimulation.

Stimulation of peripheral and cutaneous branches of the trigeminal nerve in the face, ear or scalp and the vagus nerves can be applied and stimulated at safe frequencies, pulse durations and amplitudes. An external device can be applied in, for example, the ambulance, emergency room, intensive care unit or other setting, to activate the TCR (or the allied oculo-cardiac reflex in the setting of ophthalmic nerve stimulation). Controlled stimulation may activate the TCR to safely reduce heart rate, and heart rate variability in acute myocardial infarction and heart failure, prevent and/or treat cardiac arrhythmias, protect the heart and brain from injury and ischemia, and reduce the risk of sudden death from heart disease, SIDS and epilepsy, help stabilize cardiac rhythm and prevent sudden cardiac death and treatment of impaired blood flow conditions and atrial fibrillation. Such treatment may be used to reduce mortality in heart disease. Such treatment and prevention is advantageous over the currently used pharmacological approaches which often have undesirable side effects or lack specificity in their actions. The ability to peripherally and bilaterally stimulate the vagal nerve circuits through the trigeminal pathways connection in the brainstem provides possibility of strong effects, not obtained with unilateral stimulation of the vagal nerve.

In one aspect, the disclosure describes the application of trigeminal nerve stimulation as a method to activate the trigeminal cardiac reflex (TCR) to prevent and treat cardiac arrhythmias; prevent arrhythmias and sudden cardiac death after myocardial infarction; treat heart failure; treat cerebral ischemia; treat impaired blood flow conditions and atrial fibrillation; and reduce the risk of sudden death in epilepsy and SIDS. In addition, since the trigeminal nerve projects to the dorsal motor nucleus of the vagus nerve, trigeminal nerve stimulation can be used as a safe and non-invasive method to deliver stimulation of vagus nerve circuits, without implanting a vagus nerve stimulator, and without direct stimulation of the cervical vagus nerve or its branches.

Heart Failure

Heart Failure is characterized by an increase in heart rate in response to diminished ventricular function. The increased heart rate results in increased energy demands upon an injured and dysfunctional myocardium. Further, there is abnormal parasympathetic control of the heart, as measured by a depressed baro-receptor reflex, which can lead to arrhythmias, and is associated with increased mortality. (Schwartz et al., Heart Rhythm 2009; 6:S76-S81). Vagus nerve stimulation, using implantable electrodes attached to the cervical portion of the vagus nerve, reduces heart rate and improves left ventricular function in animals and humans. (De Ferrari et al. 2010; Schwartz et al. 2009; Annegers et al., Epilepsia 2000; 41:549-53). In a rat model of chronic heart failure, vagus nerve stimulation was evaluated to determine its effects on heart rate and outcome. (Annegers et al., 2000) Using this model, a 10-15% reduction in heart rate was associated with significant improvement in survival from heart failure. (Annegers et al., 2000) Rats that underwent vagus nerve stimulation had a mortality of only 14%, versus 50% mortality among untreated rats: a 73% relative reduction in death rate. (Annegers et al., 2000) Pilot human studies of vagus nerve stimulation for heart failure are promising; preliminary data from a multicenter study of vagus nerve stimulation shows improved cardiac function (as measured by left ventricular systolic volumes and ejection fractions) when the heart rate was reduced by 5-10 beats per minute by vagus nerve stimulation. (De Ferrari et al. 2010; Schwartz et al., 2009).

Myocardial Infarction and Sudden Cardiac Death

Vagus nerve activity, as measured by baroreflex sensitivity, is significantly reduced and impaired after myocardial infarction. (Schwartz et al., 2009) As a result, there is reduced protection against severe life threatening arrhythmias and an increased risk of sudden death. Immediately after myocardial infarction, there is a surge in sympathetic activity, resulting in an increased heart rate, and increased stress on the myocardium. (Schwartz et al., 2009) Unopposed sympathetic activity can result in worsening of the infarction, and the propensity for lethal arrhythmias. In a dog model of cardiac ischemia and sudden death, implanted vagus nerve stimulation significantly reduced the risk of lethal arrhythmias (e.g. ventricular fibrillation). (Schwartz et al., 2009) Dogs treated with vagus nerve stimulation after the induction of myocardial ischemia experienced ventricular fibrillation in only 12%, versus 92% in dogs who did not undergo vagus nerve stimulation.

In the setting of acute myocardial infarction, trigeminal nerve stimulation represents a novel method of increasing vagus nerve activity, reducing heart rate, and counteracting the undesired effects of sympathetic activity on the heart. Paramedics, emergency room, and intensive care staff can apply trigeminal nerve stimulation using external electrodes, reducing the heart rate via controlled engagement of the trigeminal-cardiac reflex, and protect the heart from excessive sympathetic activity. This may improve outcome after myocardial infarction and reduce the risk of sudden cardiac death and lethal arrhythmias. (Schwartz et al., 2009)

Sudden Death in Epilepsy

Sudden unexpected death in epilepsy (SUDEP) is a major cause of death in people with epilepsy, accounting for 20-30% of the mortality associated with epilepsy. Sudden Unexpected Death in Epilepsy is generally defined as: "sudden, unexpected, witnessed, or unwitnessed, non-traumatic, and non-drowning death in an individual with epilepsy, with or without evidence of a seizure . . . in which the postmortem examination does not reveal a cause for death." (Li M et al., Circulation 2004; 109:120-124) The mechanisms of SUDEP are not completely understood, but two causes have been proposed: asphyxia/hypoxia and lethal arrhythmias related to deranged vagus-mediated autonomic control of the heart. There is evidence that vagus nerve stimulation may lower the risk of SUDEP after two years of stimulation, a finding requiring further investigation. (Li M et al., 2004) However, since current commercial forms of vagus nerve stimulation require surgical implantation to stimulate the cervical trunk of the vagus nerve in the neck, trigeminal nerve stimulation represents a novel and less invasive method to improve parasympathetic autonomic function, reduce heart rate variability, and protect the brain and heart. Therefore, trigeminal nerve stimulation can be utilized to improve the degree of vagus nerve-mediated autonomic control of the heart, and help to prevent sudden death in epilepsy. Further, since the TCR is a cerebral protective reflex, which protects the brain during hypoxia, utilizing it in patients at risk for sudden death in epilepsy may protect brain and heart function during and after seizures, when hypoxia may commonly occur.

Atrial Fibrillation

Some related cardiac related conditions are characterized by an onset event which, if left unrecognized and untreated, could lead to serious injury, such as the onset of atrial fibrillation, a cardiac rhythm disturbance that is a recognized risk factor for ischemic stroke. In one embodiment of the system, individuals who are at risk for developing atrial fibrillation could be instructed to self-apply and activate the TNS system to engage the TCR. In another embodiment, and as described in more detail below with respect to a closed loop device, a sensing element may detect a change in the condition of a patient (e.g., an electrocardiographic monitor would detect the onset of a potentially-dangerous heart rhythm) and automatically initiate trigeminal nerve stimulation.

Impaired Blood Flow Conditions

Because of the neuroprotective effects of the TCR, the use of trigeminal nerve stimulation may also include conditions in which impairment of blood flow to the brain may cause and/or worsen the progression of these conditions (collectively, "impaired blood flow conditions"). For example, many forms of dementia (e.g., Alzheimer's Disease, Vascular Dementia, Frontotemporal Dementia) are associated with impairments in blood flow to the brain, and interventions which may enhance delivery of blood to the brain may be clinically useful. Similarly, other conditions of the brain, such as multiple sclerosis, Pick's disease, the transient hypoxia produced by sleep apnea, or infectious disease of the brain (e.g. Lyme Disease, HIV/AIDS) may also have a course which may be worsened by impairments in blood flow and may be improved through the neuroprotective actions of the TCR, and therefore could benefit from TNS.

Other Medical Conditions and Disorders

Stimulation of a specific cranial nerve, the trigeminal nerve, has been found to reduce symptoms of fatigue in patients with major depressive disorder or with epilepsy. Stimulation of the trigeminal nerve to modulate activity of the vagus nerve has, surprisingly, also been found to treat other medical disorders. This non-pharmacological treatment for fatigue and other medical disorders may reduce the disability experienced by individuals with fatigue or other medical disorders, by addressing impairments from the medical condition while reducing or minimizing the side effects (including interaction with other medications and risk of addiction) posed by psychostimulants or other medications conventionally used to treat these conditions.

The unique anatomy of the trigeminal nerve, and its direct and indirect connections with key areas of the brainstem (including pons and medulla) and other structures of the nervous system involved with the vagus nerve may allow the use of cutaneous stimulation of the TNS as a method to modulate the vagus nerve or vagus nerve circuits to, surprisingly, treat various medical disorders, including, but not limited to, neurological disorders such as epilepsy, seizure related disorders, acute brain injury, chronic brain injury, chronic daily headache, migraine, disorders related to migraine and headache and movement disorders, and neuropsychiatric disorders, such as depression, mood disorders, cognitive disorders, behavioral disorders and anxiety disorders and others as disclosed elsewhere herein, obesity and other disorders related to weight and feeding, inflammation, disorders of regulation of breathing, disorders of gastrointestinal function, autonomic regulation in menopausal hot flashes, regulation of hemostasis and sleep/insomnia. Because the trigeminal nerve projects to the dorsal motor nucleus of the vagus nerve, trigeminal nerve stimulation can be used as a safe and non-invasive method to deliver stimulation of vagus nerve circuits, without implanting a vagus nerve stimulator, and without direct stimulation of the cervical vagus nerve or its branches.

Fatigue

In another aspect, the present disclosure relates to methods, devices and systems used for the treatment of fatigue via stimulation of the superficial elements of the trigeminal nerve ("TNS") to modulate the locus coeruleus or modulate the reticular activating system.

Without wishing to be bound by any particular theory, mechanisms of action by which TNS may counter fatigue include, but are not limited to: (a) influence on the activity of the locus coeruleus, a brain center involved in the production and regulation of the neurotransmitter norepinephrine, and (b) influence on the activity of the reticular activating system (RAS), a brain system involved in regulating levels of consciousness, arousal, wakefulness and attention, and (c) influence on activity of the vagus nerve, which allows for signaling between the brain and multiple internal organs and body systems (e.g. immune), as detailed below.

Tinnitus

Tinnitus, sometimes called "ringing in the ears," is a condition in which a person has the experience of hearing a sound in the absence of corresponding external sound. Tinnitus is common, affecting 20% of the population above the age of 55. It is commonly associated with injury to the auditory system and it can arise in many contexts, including exposure to abnormally loud sounds, ear infections, foreign objects in the ear, nose allergies that prevent (or induce) fluid drain, as a side effect of some medications, as a part of aging, or as a part of a congenital hearing loss. Without wishing to be bound by any particular theory, stimulation of the trigeminal nerve may be able to treat the symptoms of tinnitus.

The cochlear nuclei are the principal brainstem structures responsible for hearing. The paired cochlear nuclei are located in the dorsal and lateral portions of the right and left medulla. The cochlear nuclei are divided into two predominant regions, the dorsal cochlear nucleus (DCN) and the ventral cochlear nucleus (VCN). The cochlear nuclei receive auditory (hearing) input from the cochlear nerves, which receives its input from the ear, specifically the cochlea. Fibers from the cochlear nuclei project to the central auditory pathways, including the lateral lemniscus, inferior colliculus, medical geniculate body, and finally to the primary auditory cortex.

The cochlear nuclei receive input from both the cochlear (auditory) nerve, and other pathways, including the trigeminal nerve, which provides somatosensory information from the face. There are fibers of the trigeminal nerve located over the anterior portion of the external ear canal, and the input from these and other trigeminal branches may help serve to help localizing the source of sound to the listener. Trigeminal nerve input serves to modulate the response of the two cochlear nuclei, and can inhibit or increase the response of the cochlear nuclei to auditory input (sound). (Shore et al., "Dorsal cochlear nucleus responses to somatosensory stimulation are enhanced after noise-induced hearing loss." Eur J Neurosci 2008; 27:155-168)

When the cochlear nerve is injured, the cochlear nuclei (especially the DCN) exhibit enhanced sensitivity to trigeminal input, and increased inhibition of the cochlear nuclei. (Shore et al. 2008) This enhanced sensitivity may play a role in the pathogenesis of tinnitus. (Shore et al. 2008)

Without wishing to be bound by any particular theory, stimulation of the trigeminal nerve may result in reducing tinnitus by modulating trigeminal input to the cochlear nuclei. Since the cochlea exhibit heightened sensitivity to trigeminal input, stimulation of the trigeminal nerve can be performed to reduce or modulate trigeminal enhanced inhibition of the cochlear nuclei after injury, or increase or modulate trigeminal activation of the cochlear nuclei after cochlear nerve injury.

In some embodiments, trigeminal nerve stimulation can be delivered via stimulation of auricular branches located over the anterior auditory canal, or by stimulating cutaneous branches including the auriculotemporal, zygomaticotemporal, mentalis, infraorbital, or supraorbital branches via cutaneous (or transcutaneous) stimulation of these branches. In some embodiments, frequencies may range from 1-5000 Hz, at amplitudes of 0.1-40 mA. In some embodiments, frequencies may range from 1-10000 Hz, at amplitudes of 0.1-40 mA. TNS may be used to calm the dorsal cochlear nucleus (or other relevant structure) with a feedback control loop that may allow the patient in real-time to provide an audiologist with information on which stimulation parameters (such as frequency, pulse width, duty cycle) best mitigate the ringing in the patient's ears. In addition, self-tuning control algorithms can adjust the stimulation parameters to mitigate accommodation effects and changes in the ringing frequency spectrum.

Obesity and Other Disorders Related to Weight and Feeding and Related Conditions Without wishing to be bound by any particular theory, TNS can be used to modulate vagus nerve activity to treat obesity. Conditions related to obesity that may also be treated by modulating vagus nerve activity include: diabetes (worsened in obesity), metabolic syndrome (worsened in obesity), dyslipidemia (worsened in obesity), obstructive sleep apnea (precipitated by excessive soft tissue which may obstruct the airway, in obesity), arthritis (both osteoarthritis, tied to weight load on the joint, and rheumatoid arthritis, where excess weight accelerates joint destruction), and cachexia/anorexia (arising either from cancer or from a psychiatric disorder). See e.g. Val-Laillet D, et al., Slower eating rate is independent to gastric emptying in obese minipigs, Physiol Behav., 2010 Nov. 2; 101(4): 462-8, Epub 2010 Aug. 5; Tome D, et al., Protein, amino acids, vagus nerve signaling, and the brain, Am J Clin Nutr., 2009 September; 90(3):838S-843S, Epub 2009 Jul. 29; Kral J G, et al., Vagal nerve function in obesity: therapeutic implications, World J Surg, 2009 October; 33(10):1995-2006; Green M A, et al., An association between eating disorder behaviors and autonomic dysfunction in a nonclinical population. A pilot study, Appetite, 2009 August; 53(1):139-42, Epub 2009 May 13; Song C K, et al., Anterograde transneuronal viral tract tracing reveals central sensory circuits from white adipose tissue, Am J Physiol Regul Integr Comp Physiol, 2009 March; 296(3):R501-11, Epub 2008 Dec. 24; Acampa M, et al., Sympathetic overactivity and plasma leptin levels in Rett syndrome, Neurosci Lett, 2008 Feb. 13; 432(1):69-72, Epub 2007 Dec. 23; Kapica M, et al., Obestatin stimulates the secretion of pancreatic juice enzymes through a vagal pathway in anaesthetized rats—preliminary results, J Physiol Pharmacol, 2007 August; 58 Suppl 3:123-30; The following journal articles which may include studies that show an effect on cachexia/anorexia by modulating vagus nerve activity: Suneja M, et al., Hormonal regulation of energy-protein homeostasis in hemodialysis patients: an anorexigenic profile that may predispose to adverse cardiovascular outcomes, Am J Physiol Endocrinol Metab, 2011 January; 300(1):E55-64, Epub 2010 Oct. 19; Laviano A, et al., Neural control of the anorexia-cachexia syndrome, Am J Physiol Endocrinol Metab, 2008 November; 295(5): E1000-8, Epub 2008 Aug. 19; Plata-Salamân CR, Central nervous system mechanisms contributing to the cachexia-anorexia syndrome, Nutrition, 2000 Oct.; 16(10):1009-12.

Inflammatory Processes

Without wishing to be bound by any particular theory, TNS can be used to modulate vagus nerve activity to treat inflammatory processes in the body. Conditions related to these inflammatory processes that may also be treated by modulating vagus nerve activity include: asthma, inflammatory bowel disease, atopic dermatitis, sepsis and hepatitis. The following journal articles may include studies that show an effect on inflammatory processes and other conditions in which inflammation plays a role, by modulating vagus nerve activity: inflammatory processes: Minutoli L, et al., Melanocortin 4 receptor stimulation decreases pancreatitis severity in rats by activation of the cholinergic anti-inflammatory pathway, Crit Care Med, 2011 May; 39(5):1089-96; Lehrer P, et al., Voluntarily produced increases in heart rate variability modulate autonomic effects of endotoxin induced systemic inflammation: an exploratory study, Appl Psychophysiol Biofeedback, 2010 December; 35(4):303-15; Ottani A, et al., Melanocortins counteract inflammatory and apoptotic responses to prolonged myocardial ischemia/reperfusion through a vagus nerve-mediated mechanism, Eur J Pharmacol, 2010 Jul. 10; 637(1-3):124-30, Epub 2010 Apr. 10; Thayer J F, Vagal tone and the inflammatory reflex, Cleve Clin J Med, 2009 April; 76 Suppl 2:S23-6; Haensel A, et al., The relationship between heart rate variability and inflammatory markers in cardiovascular diseases, Psychoneuroendocrinology, 2008 November; 33(10):1305-12, Epub 2008 Sep. 25; Thayer J F and Sternberg E M, Neural aspects of immunomodulation: focus on the vagus nerve, Behav Immun, 2010 Nov.; 24(8):1223-8, Epub 2010 Jul. 30; Balbo S L, et al., Fat storage is partially dependent on vagal activity and insulin secretion of hypothalamic obese rat, Endocrine, 2007 Apr.; 31(2):142-8; Pavlov V A, et al., Brain acetylcholinesterase activity controls systemic cytokine levels through the cholinergic anti-inflammatory pathway, Brain Behav Immun, 2009 Jan.; 23(1):41-5, Epub 2008 Jun. 27; Kox M, et al., Increased vagal tone accounts for the observed immune paralysis in patients with traumatic brain injury, Neurology, 2008 Feb. 5; 70(6):480-5; Marsland A L, et al., Stimulated production of proinflammatory cytokines covaries inversely with heart rate variability, Psychosom Med, 2007 November; 69(8):709-16, Epub 2007 Oct. 17; asthma: Li H F and Yu J., Airway chemosensitive receptors in vagus nerve perform neuro-immune interaction for lung-brain communication, Adv Exp Med Biol, 2009; 648:421-6; inflammatory bowel disease: Meregnani J, et al., Anti-inflammatory effect of vagus nerve stimulation in a rat model of inflammatory bowel disease, Auton Neurosci, 2011 Feb. 24; 160(1-2):82-9, Epub 2010 Nov. 11; Van Der Zanden E P, et al., The vagus nerve as a modulator of intestinal inflammation, Neurogastroenterol Motil, 2009 Jan.; 21(1): 6-17; atopic dermatitis Boettger M K, et al., Increased vagal modulation in atopic dermatitis., J Dermatol Sci, 2009 January; 53(1):55-9, Epub 2008 Sep. 13; sepsis: Huston J M, et al., Transcutaneous vagus nerve stimulation reduces serum high mobility group box 1 levels and improves survival in murine sepsis, Crit Care Med, 2007 December; 35(12):2762-8; hepatitis: Hiramoto T, et al., The hepatic vagus nerve attenuates Fas-induced apoptosis in the mouse liver via alpha7 nicotinic acetylcholine receptor, Gastroenterology, 2008 June; 134(7):2122-31, Epub 2008 Mar. 8.)

Disorders of the Regulation of Breathing

Without wishing to be bound by any particular theory, TNS can be used to modulate vagus nerve activity to treat disorders of the regulation of breathing. The following link provides a journal article which may include studies that show an effect on disorders of the regulation of breathing by modulating vagus nerve activity: Tadjalli A, et al., Identification of a novel form of noradrenergic-dependent respiratory motor plasticity triggered by vagal feedback, J Neurosci, 2010 Dec. 15; 30(50):16886-95).

Disorders of Gastrointestinal Function

Without wishing to be bound by any particular theory, TNS can be used to modulate vagus nerve activity to treat disorders of gastrointestinal function. These disorders may include: gastroesophageal reflux, diarrhea and constipation, gastrointestinal pain syndromes ("functional bowel syndromes"), post-operative ileus, dyspepsia, motion sickness, and chemotherapy-related nausea and emesis. The following journal articles may include studies that show an effect on disorders of gastrointestinal function by modulating vagus nerve activity: gastroesophageal reflux: Niedringhaus M, et al., "Dorsal motor nucleus of the vagus: a site for evoking simultaneous changes in crural diaphragm activity, lower esophageal sphincter pressure, and fundus tone," Am J Physiol Regul Integr Comp Physiol. (2008) 294(1):R121-31; diarrhea and constipation; dysphagia and other disturbances of swallowing (e.g. following a stroke or traumatic brain injury (TBI)): Bansal V, et al., "Stimulating the central nervous system to prevent intestinal dysfunction after traumatic brain injury," J. Trauma (2010) 68(5):1059-64; gastroparesis: Hasler W L. "Methods of gastric electrical stimulation and pacing: a review of their benefits and mechanisms of action in gastroparesis and obesity," Neurogastroenterol Motil. (2009) 21(3):229-43; gastrointestinal pain syndromes ("functional bowel syndromes"); post-operative ileus: Lubbers T, et al., "Controlling postoperative ileus by vagal activation," World J Gastroenterol (2010) 16(14):1683-87; The F O, et al., "Activation of the cholinergic anti-inflammatory pathway ameliorates postoperative ileus in mice," Gastroenterology (2007) 133(4):1219-28; dyspepsia: Hjelland I E, et al., "Breathing exercises with vagal biofeedback may benefit patients with functional dyspepsia," Scand J Gastroenterol. (2007) 42(9):1054-62; motion sickness: Percie du Sert N, et al., "Telemetry in a motion-sickness model implicates the abdominal vagus in motion-induced gastric dysrhythmia," Exp Physiol. (2010) 95(7):768-73; chemotherapy-related nausea and emesis: Urayama Y, et al., "Electrical and chemical stimulation of the nucleus raphe magnus inhibits induction of retching by afferent vagal fibers," Auton Neurosci. (2010) 152(1-2):35-40; Ray A P, et al., "Receptor-selective agonists induce emesis and Fos expression in the brain and enteric nervous system of the least shrew (*Cryptotis parva*)," Pharmacol Biochem Behav. (2009) 94(1):211-18; Wang J J, et al., "Electro-acupuncture of Tsusanli and Shangchuhsu regulates gastric activity possibly through mediation of the vagus-solotary complex," Hepatogastroenterology (2007)$_{54}$(78):1862-67.

Autonomic Instability of Menopausal Hot Flashes

Without wishing to be bound by any particular theory, TNS can be used to modulate vagus nerve activity to treat autonomic instability of menopausal hot flashes. The following journal article may include studies that show an effect on autonomic instability of menopausal hot flashes by modulating vagus nerve activity: Thurston R C, et al., "Hot flashes and cardiac vagal control: a link to cardiovascular risk?," Menopause (2010) 17(3):456-61.

Regulation of Hemostasis (Blood Clotting)

Without wishing to be bound by any particular theory, TNS can be used to modulate vagus nerve activity to regulation hemostasis (blood clotting). The following links provide journal articles which may include studies that show an effect on hemostasis by modulating vagus nerve activity: Czura C J, et al., "Vagus nerve stimulation regulates hemostasis in swine," Shock (2010) 33(6):608-13; Kraemer M, et al., "The influence of vasovagal response on the coagulation system," Clin Auton Res. (2010) 20(2):105-11.

Insomnia and Disturbances of Sleep

Sleep disturbances can arise in a range of conditions, including sleep apnea, hyperthyroidism, depression, and primary insomnia. Stimulation of the trigeminal nerve may be able to treat sleep disturbances by means of its influences on brain systems related to wake/sleep cycles and arousal. Without wishing to be bound by any particular theory, projections from the trigeminal nerve to the nucleus of the tractus solitarius (NTS) convey signals to the NTS and then to other brain regions involved in the regulation of sleep and wakefulness, for example, via the parabrachial nucleus, to the hypothalamus, amygdala, insula, lateral prefrontal cortex, and other regions of relevance (A. Jean. *Arch Int Physiol Biochim Biophys.* 1991 99:A3-52; T. R. Henry *Neurology* 2002 59(6 Suppl 4):53-14; R. Ruffoli et al., *J Chem Neuroanat*, in press). Other projections to the locus coeruleus (LC), the brain's major source of the neurotransmitter norepinephrine, and to the reticular activating system (RAS) may also play a role in sleep/wake regulation.

As supporting experimental data of the beneficial effects of TNS on insomnia, the scores on the insomnia items of the Quick Inventory of Depressive Symptomatology for ten adults with major depression who participated in a clinical trial of TNS were examined. On this well-established rating scale, the first three questions assess (a) sleep onset insomnia (i.e., delay in falling asleep), (b) nocturnal insomnia (awakening during the night), and (c) early morning insomnia (awakening earlier than intended and being unable to return to sleep). Summarizing the responses to these three items gives an index of severity of insomnia in these subjects, ranging from zero (no symptoms) to six (maximal disturbance across all three types of insomnia symptom). Over the course of this 8 week trial, this measure of insomnia severity fell from an average of 2.5 (1.8 s.d.) to 1.2 (1.0 s.d.), a decrease of over 50% which achieved statistical significance (2-tail paired t-test $p<0.05$).

Neurological Disorders

The neuroanatomic pathways allow targeted modulation of activity in areas involved in epilepsy and other neurological conditions and disorders (e.g. locus coeruleus, anterior cingulate, insular cortex). Thus, the systems, devices and methods as disclosed herein utilize the brain's existing infrastructure to transmit signals to the targets of interest. Example conditions and disorders include: coma and vegetative State, headache and migraine, movement disorders, include, but are not limited to, tremors, twitches, and spasms, involuntary increases in tone of muscles, such as dystonias, and complex movements, such as dyskinesias and choreas, tardive and other dyskinesias.

For a discussion of certain embodiments of methods, systems and devices using cutaneous electrodes according to aspects of the present disclosure, reference is now made to FIGS. 4-7, which show various embodiments of the systems and devices that may be used for the cutaneous stimulation of the superficial branches of the trigeminal nerve and methods of using the same.

According to one aspect of the present disclosure, a method of treating medical disorders using trigeminal nerve stimulation ("TNS") is provided. Broadly speaking, the method of treating medical disorders by TNS comprises positioning external electrodes over or near at least one of the foramina or branches of the trigeminal nerve (FIGS. 1A and 1B), and stimulating the electrodes using a stimulator for a fixed time at specified operational parameters. The electrodes need not be applied at the main branch of the nerve; they can be applied in the area of the skin supplied by that nerve, which may be inches away from the main branch of the nerve. In one embodiment, the external electrodes are positioned over the foramina of the supraorbital or ophthalmic nerves (FIG. 1A, Foramen 1) since unilateral stimulation or bilateral stimulation of the trigeminal nerve is achievable by placing single or separate electrodes on the right and/or left sides (e.g. by placing an electrode assembly, such as two separate electrodes, a single paired electrode or two pairs of electrodes, each electrode having at least one contact, over the forehead or other region of the patient's face). In one embodiment, the electrode assembly is configured for unilateral stimulation. In one embodiment, the electrode assembly is configured for bilateral stimulation. In some embodiments, bilateral stimulation may offer similar or better efficacy than unilateral stimulation because the function of different brain structures may not be the same on right and left. There may also be synergistic effects that arise with bilateral stimulation. In some embodiments, two separate electrodes or a single paired electrode may be placed over the forehead. In alternative embodiments, the electrode can be positioned over the foramina of the infraorbital foramen (infraorbital or maxillary nerves) (FIG. 1A, Foramen 2) or the mentalis foramen (mentalis or mandibular nerves) (FIG. 1B, Foramen 3). In yet other embodiments, the stimulation can be unilaterally applied to one foramen of the trigeminal nerves. In other embodiments, the method of treating fatigue and other medical disorders includes positioning external electrodes over a plurality of foramina and simultaneously stimulating different trigeminal nerves. In other embodiments, electrodes may be positioned at a region of the patient's face (on the right and/or left side) corresponding with the supratrochlear nerve, infratrochlear nerve, zygomaticotemporal, zygomaticofacial, zygomaticoorbital, nasal, and/or auriculotemporal nerves and/or their respective foramina. It should be appreciated that the operations/steps of the methods described herein may be performed in the order illustrated, in another suitable order and/or one or more operations may be performed simultaneously. Moreover, in some embodiments, the methods may include more or fewer operations/steps than those illustrated/described elsewhere herein.

According to one aspect of the present disclosure, the method of treating fatigue and other medical disorders by TNS comprises selecting patient specific values for the operational parameters for the stimulation of each individual patient within a defined range. In one embodiment, the values of the operational parameters are selected such that a patient will experience a stimulation sensation, such as a mild tingling over the forehead and scalp without being in discomfort or in pain. In one embodiment, the values of the operational parameters are selected such that skin irritation, burns or other skin injury, pain, headache, and undesired effects on the brain (e.g. inducing seizures), and/or the cranial nerves are minimized or reduced. In one embodiment, the method of selecting operational parameters comprises evaluating variables such as the configuration and size of the electrode, the pulse duration, the electrode current, the duty cycle and the stimulation frequency; which are important factors in ensuring that the total charge, the charge density, and charge per phase are well within accepted limits for the skin, nerve and brain. For example, to minimize skin irritation, it is not sufficient to merely state the total current, but the current density needs to be defined. In one embodiment, selection of the electrical stimulation parameters, electrode design, and inter-electrode distance are chosen such that the electrical stimulation zone includes the ophthalmic or other cutaneous nerve branches (approximately 3-4 mm below the skin surface), while preventing or minimizing current penetration beneath the skull bone as described above.

As described in more detail below with respect to FIGS. 4-7, the electrodes connect to leads for conveying the electrical stimuli from a neurostimulator. In some embodiments, the neurostimulation may be provided using an electrical neurostimulator at the following exemplary settings: frequency 1-300 Hz, current 1-40 mA, pulse duration (pulse width) of 50-500 microseconds, a duty cycle of up to 50%, for at least one hour per day. In some embodiments for treatment of fatigue, the neurostimulation may be provided using an electrical neurostimulator at the following exemplary settings: frequency 120 Hz, current up to 25 mA, pulse duration (pulse width) of 250 microseconds, a duty cycle of 30 seconds on/30 seconds off, for at least eight hours per day. In some embodiments, the current amplitudes are less than 7 mA, or less than 6 mA, depending on the size, impedance, resistance, or configuration of the electrode(s). In some embodiments, the current amplitude is between about 2.5 mA and about 5 mA. In still another embodiment, the output current may be limited to an exact current, e.g. 5 mA, up to a maximum of a fixed current of 7 mA, depending on the size, resistance, or impedance of the electrode. In another embodiment, the output current is limited to a range not to exceed 10 mA, or 7 mA, or 5 mA. For patient comfort and low power consumption, stimulation parameters at the lower end of these ranges may be used, but this may be balanced with differences in clinical effect which may vary over the range of stimulation parameters. In other embodiments, different values of the operational parameters may be used. In alternative embodiments, a single external electrode can be used. In some embodiments, as described in more detail below, a portable external stimulator, which can be attached to a patient's clothing, is used.

Figure 4:
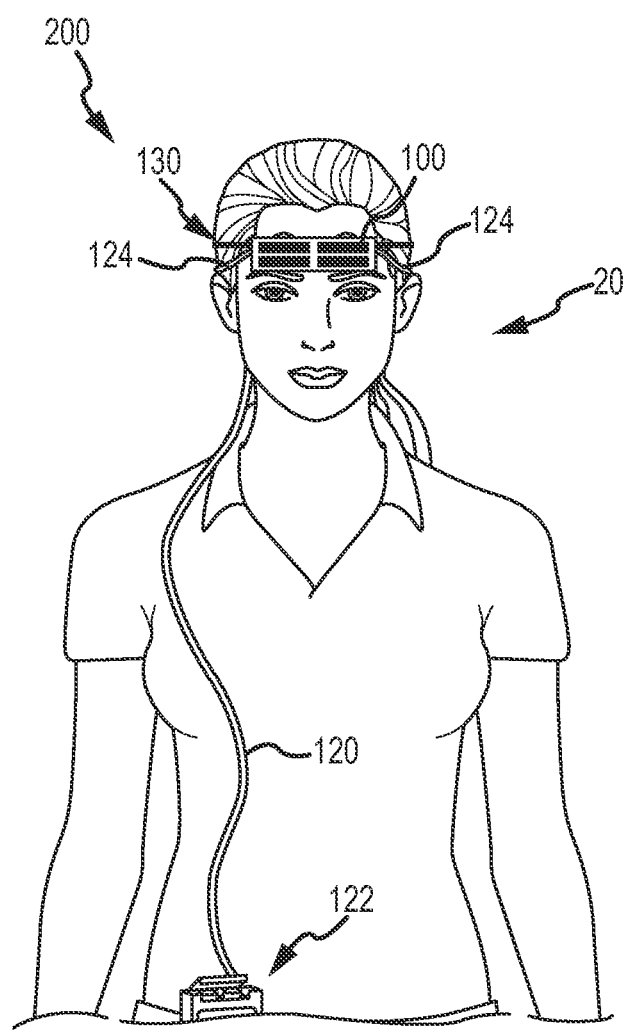
FIG. 4 shows an embodiment of a system including an electrode assembly provided according to aspects of the present disclosure.

In one embodiment, as can be understood from FIGS. 4-7, a system 200 for treatment of various medical disorders via TNS includes an electrode assembly 100, electrical cable or wire 120 and an external neurostimulator or pulse generator 122. The electrode assembly may be configured for the bilateral simultaneous and asynchronous stimulation of the ophthalmic nerves. The neurostimulator or pulse generator may be any type of appropriate stimulating, signal-generating device. In the illustrated embodiment, the generator 122 is portable and attached to the belt of a patient 20. However, either a portable or non-portable pulse generator may be used. As shown in FIG. 4, the electrode assembly 100 is connectable to an external stimulator 122 either by lead wires 124 connected to an electrical cable 120 or wirelessly. That is, in one embodiment, the electrical cable or wire 120 is configured to provide a physical and electrical link between the generator 122 and the electrode assembly 100 via lead wires 124. In other embodiments, the generator 122 and the electrode assembly 100 communicate wirelessly (i.e. the wire 120 and leads 124 are not used). The system 200 or elements thereof, such as the electrode assembly 100, may be part of a kit. In some embodiments, the kit may also include instructions for placement of the electrode assembly and/or system to stimulate the trigeminal nerve to activate the vagus nerve to treat or prevent various medical disorders as disclosed herein. In some embodiments, the kit may also include instructions for placement of the electrode assembly and/or system to stimulate the trigeminal nerve to activate the TCR to treat or prevent a cardiac related disorder. In some embodiments, the kit may also include instructions for monitoring the clinical effects of the stimulation to ensure proper adjustment of stimulation parameters and system configuration. In some embodiments, the kit may also include instructions for treatment of various medical disorders as disclosed herein according to a method as disclosed herein. The instructions may be provided in any readable format or as a link to a website.

In some embodiments, the system 200 may also include a regulation device to ensure safe use of the system. The regulation device is configured to be attached to the pulse generator 122 and, in some embodiments, is configured to govern the maximum charge balanced output current below approximately 1-25 mA to minimize current penetration to the brain and increase patient tolerance. In some embodiments, the regulation device is configured to govern the maximum charge balanced output current below approximately 40 mA. The regulation device may be internally programmed to range from 0.25-5.0 mA, 0-10 mA, 0-15 mA, depending on the surface area, placement, and orientation of the electrode, and whether the electrode is stimulating near or adjacent to the skull, or away from the skull, (mentalis), where current ranges may be higher or lower. Current TENS units stimulate with maximum output currents of up to 100 mA's, which result in currents which may penetrate the skull and which may not be well tolerated.

In some embodiments, the electrode assembly 100 further includes a retainer element 130 configured to secure the electrode assembly to a patient's forehead. In one embodiment, the retainer element 130 can be an elastic band or strap. In alternative embodiments, the electrode assembly 100 can be secured in place by a hat or a cap which also serves to conceal the electrode assembly from view. In still other embodiments, the electrode assembly may be secured by adhesive, such as an adhesive strip, an adhesive backing surrounding the conducting area, or an adhesive conductive gel.

In some embodiments, the system may utilize a closed loop design and may include a closed loop or sensing device. In such a system, the closed loop device may include the stimulating electrode or additional set of electrodes, indwelling catheters, or cutaneous or implantable physiologic monitors. The device may be configured to detect heart rate, pulse oximetry, cerebral blood flow, systolic, diastolic blood pressure, or mean arterial pressure, transcranial Doppler, cardiac parameters (ejection fraction, pulmonary, atrial, or ventricular pressures), heart rate variability (using time, frequency, or non-linear or other measures of heart rate variability), the presence of molecules that could signify a potentially-dangerous condition (e.g., tropinin in the bloodstream, a biomaker that may indicate injury to the heart muscle tissue, as might be treated in an ambulance, an emergency room, and/or an intensive care unit) or the achievement of a desired clinical effect (e.g., levels of proinflammatory cytokines), or other physiologic parameters to provide self-tuning adaptive feedback control for the neurostimulator including, but not limited to, fuzzy controllers, LQG controllers and artificial neural networks (ANN). Adaptive learning controllers can learn from the previous response of a particular patient or similar patients to stimulation settings which helped alleviate conditions being treated, such as tachycardia or atrial fibrillation. For example, in one embodiment, a closed loop device may detect heart rate and adjust the output current or voltage or other parameter to limit heart rate reductions to a prescribed level. In some embodiments, this qualitative and/or quantitative feedback may be used by the system to automatically or otherwise adjust the stimulation parameters in a closed-loop fashion to optimize the clinical effects of the stimulation.

In some embodiments, the electrode assembly comprises an electrode with at least one contact. In some embodiments, a single electrode may have a plurality of contacts. In some embodiments, the electrode assembly comprises pair of electrodes with a pair of contacts. In some embodiments, the electrode assembly may be a strip electrode with at least one contact. In some embodiments, the strip electrode may include a plurality of contacts.

Figure 5A:
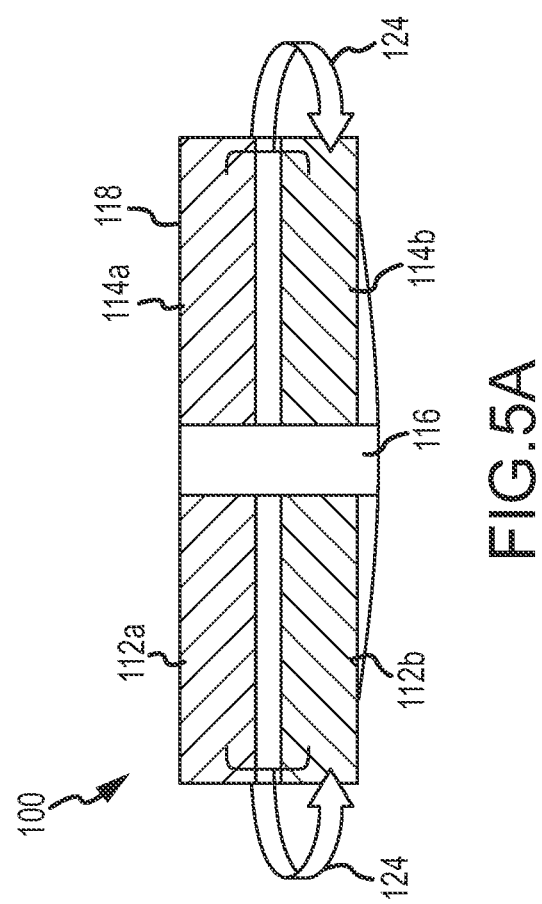
FIG. 5A depicts an enlarged view of the electrode assembly of FIG. 4.
Figure 5B:
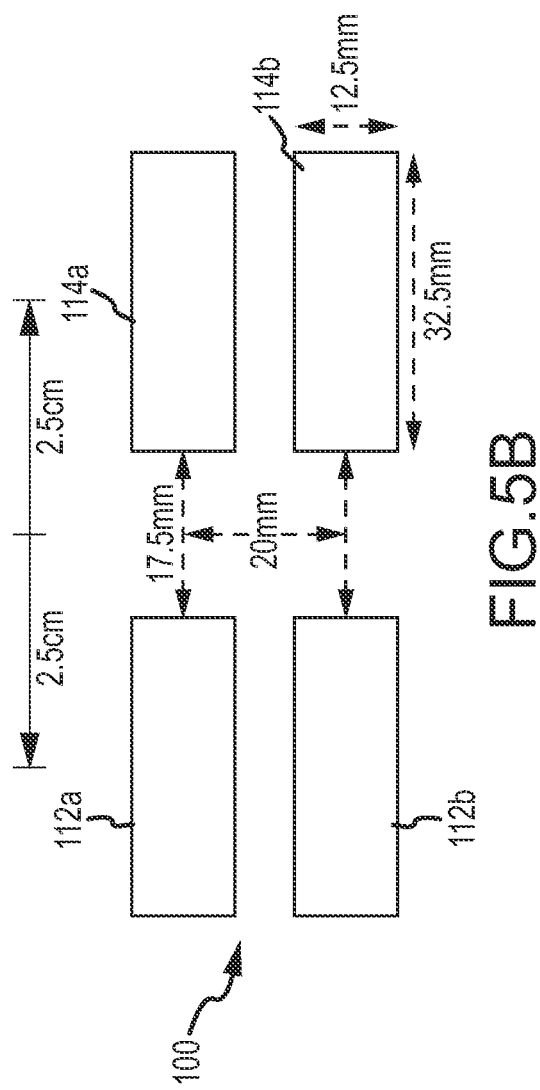
FIG. 5B depicts representative dimensions of the electrode assembly of FIG. 5A.

The electrode assembly 100 shown in FIGS. 4-5B is also referred to as a bilateral supraorbital electrode. As illustrated in FIGS. 4-5B, the electrode assembly 100 includes a first pair of contacts 112a, 112b for placement on a first region of the patient's face, and a second pair of contacts 114a, 114b for placement on a second region of the patient's face. In some embodiments, the first region is the right side of the patient's face and the second region is the left side of the patient's face. The first pair of contacts comprises a first upper contact 112a and a first lower contact 112b, while the second pair of contacts comprises a second upper contact 114a and a second lower contact 114b. The first and second contact pairs are connected to each other by an insulative connection region 116. The electrode assembly 100 comprises an inner contact surface 118 that comes into contact with a patient's skin at four contact areas, each corresponding to one of the four contacts 112a, 112b, 114a, 114b. The inner contact surface 118 comprising the four contact areas includes a buffered gel-like adhesive that provides good electrical conductivity with minimum skin irritation, an example of such gel includes the commercially available hydrogels from AmGel Technologies (AmGel Technologies, Fallbrook, Calif., USA).

In one embodiment, the electrode assembly 100 is configured to stimulate both the right and left ophthalmic nerves either simultaneously or asynchronously. The insulative connection region 116 serves to assist a patient in lining up the electrode assembly 100 with the midline of the nose to ensure proper placement of the electrode assembly 100 over both ophthalmic nerves, which lie on the average about 2.1 to 2.6 cm from the nasal midline of an adult patient. Thus, the electrode assembly can be placed accurately (e.g. by the patient) without knowledge of the location of the ophthalmic nerve or key landmarks relative to the nerve, thereby reducing the possibility of inadequate stimulation due to errors in positioning of the electrodes.

Figure 6A:
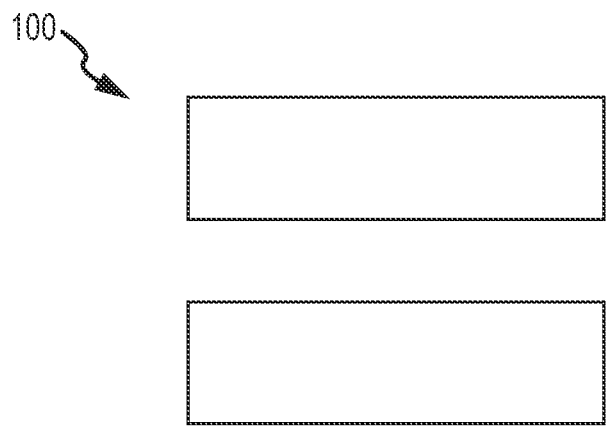
FIGS. 6A-6C depict various embodiments of the cutaneous electrode assembly of FIG. 4.
Figure 6B:
Figure 6C:
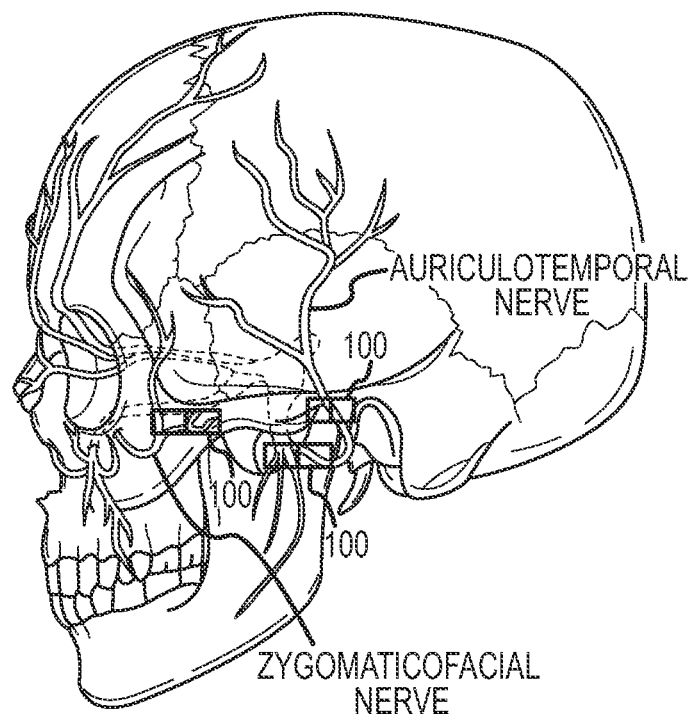

The placement of the first contact pair 112a, 112b and the second contact pair 114a, 114b on opposite sides of the nasal midline assures that stimulation current moves orthodromically or in the direction of the afferent ophthalmic or supraorbital nerve. Furthermore, this configuration of the electrode assembly 100 allows the contact pairs 112a/112b and 114a/114b to be stimulated independently and/or unilaterally, as the response to stimulus may be localized and thus varied from one side of the midline to the other side. That is, the presently disclosed electrode assembly permits individual adjustment of current for the first and second regions or right and left sides, as applicable, thereby reducing asymmetric stimulation and/or perceived asymmetric stimulation. FIGS. 6A-6C illustrate other embodiments of the electrode assembly 100, which configurations may be used to stimulate the right and/or left ophthalmic nerve and/or other branches of the trigeminal nerve as disclosed herein, such as the infraorbital nerve branch. It can be appreciated that a single electrode with one or more contacts or multiple electrodes with one or more contacts may be used. The bilateral supraorbital electrode is specially configured for bilateral supraorbital stimulation. In some embodiments, it is scalable based on the location of use, stimulation parameters and input from computer modeling so as to negate or minimize or render safe, current penetration into the brain. As skin irritation may occur, a similar configuration could be applied unilaterally, so as to provide relief to one side of the forehead, to promote skin tolerability and to reduce the risk of irritation. Other configurations of size and inter-electrode distance can be conceived for different branches of the trigeminal nerve, as shown in FIGS. 6A-6C. In one embodiment, a strip electrode with at least two contacts may be used to stimulate the infraorbital nerve. In other embodiments, two separate electrodes may be used to stimulate the infraorbital nerve. In another embodiment, a strip electrode with at least two contacts may be used to stimulate the auriculotemporal and/or zygomaticofacial nerve. In still other embodiments, two separate electrodes may be used to stimulate the auriculotemporal and/or zygomaticofacial nerve.

For stimulations wherein electrical pulses of a single polarity (monophase—either all positive pulses or all negative pulses) are generated, the upper contacts 112a, 114a and lower contacts 112b, 114 have fixed polarities. For stimulations wherein electrical pulses of alternating polarities (biphasic—alternating positive and negative pulses or pulse trains) are generated, the upper contacts 112a, 114a and lower contacts 112b, 114b have alternating polarities. Also, the inferior electrode typically serves as the cathode for the leading phase of the stimulating pulse. In the case of a monophasic stimulation, the inferior electrode generally becomes the cathode.

As can be understood from FIG. 5B, each of the contacts 112a, 112b, 114a, 114b is sized to deliver an electrical pulse over a large enough surface area to minimize any skin injury due to excess current density and/or charge density, and to minimize or eliminate current penetration beyond the inner surface of the skull bone. The distance between the first contact pair 112a, 112b and the second contact pair 114a, 114b is configured to stimulate the ophthalmic nerves while minimizing or eliminating current delivery to the surface of the brain. In one embodiment, the mid-point of each of the contacts is approximately 2.5 cm (range 1.5 cm to 3.5 cm) from the nasal midline. The electrode size and the inter-electrode distance may vary for children and adults, males and females based on anatomical differences. In one embodiment, the electrode is approximately 32.5 mm in length by 12.5 mm in height and the inter-electrode distance between, for example, the upper pair of electrodes 112a, 114a is 17.5 mm and the inter-electrode distance between, for example, the upper electrode 112a and the lower electrode 112b is 20 mm. In other embodiments, the length of the electrode may be greater than or less than 32.5 mm and greater than or less than 12.5 mm in height. In still other embodiments, the inter electrode distance can be in a range greater than 20 mm and/or less than 17.5 mm. In various embodiments, the surface area of each of the contacts 112a, 112b, 114a, and 114b can be within a range of about 0.5 cm$^2$ to about 20 cm$^2$. In various embodiments, the distance between the contacts 112a and 112b and the distance between contacts 114a, and 114b can be in a range of about 0.5 cm to about 10 cm. Those of skill in the art will recognize that one or more of the above distances can be used as a border of a range of distances.

Figure 7:
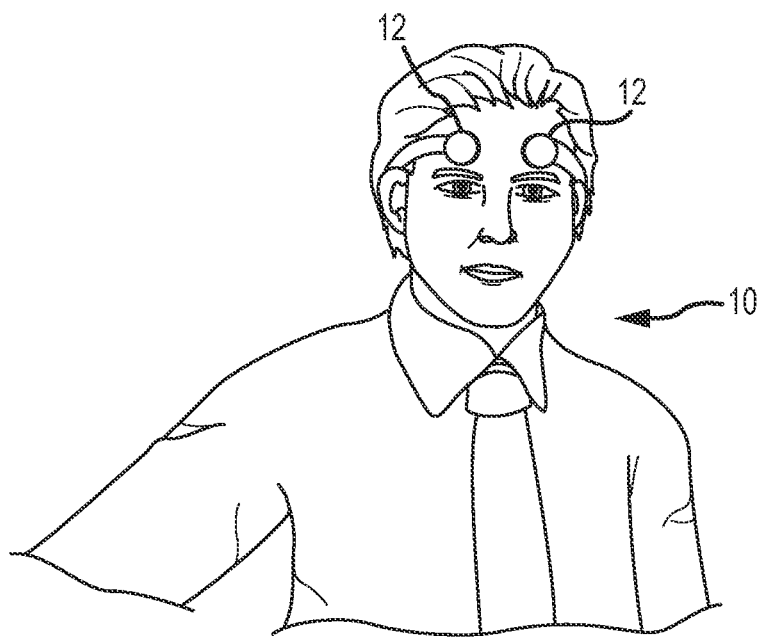
FIG. 7 shows another embodiment of an electrode assembly that may be used with the system of FIG. 4.

FIG. 7 illustrates another embodiment of the electrode assembly 100. As shown in FIG. 7, a patient 10 is wearing two separate electrodes 12 on the forehead, one over each eyebrow, corresponding to the foramina of the ophthalmic nerves.

Figure 8A:
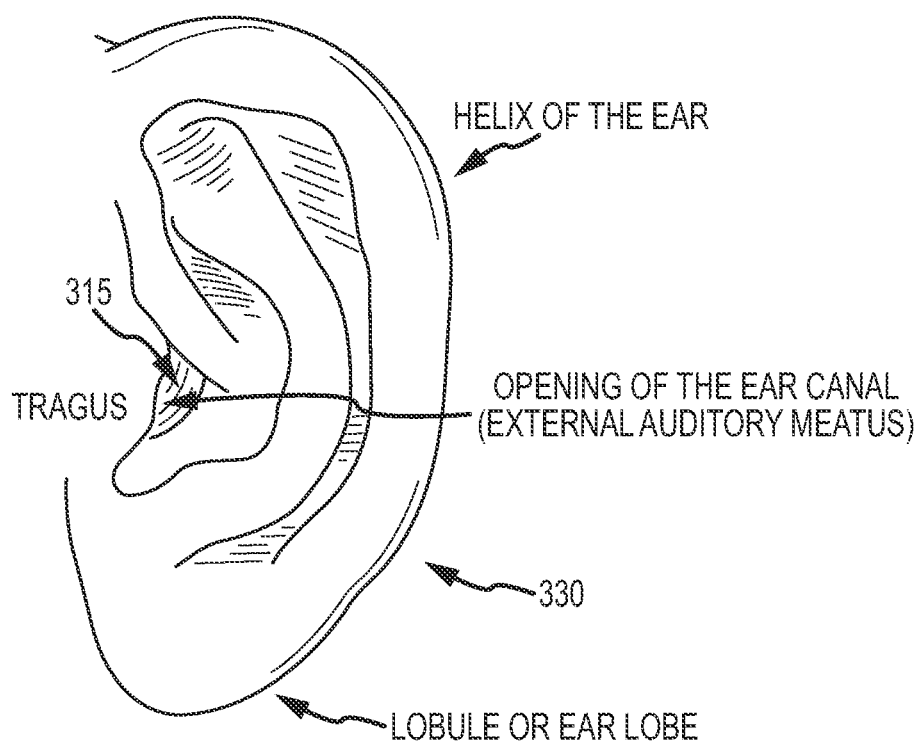

In another aspect of the present disclosure, embodiments in which stimulation is applied to fibers of multiple cranial nerves ("polycranial nerve stimulation") are disclosed. With respect to FIGS. 8A to 8C-2, in such embodiments, stimulation can be applied to aspects of the trigeminal nerve which innervate portions of the ear, particularly the auricle (external ear) and the ear canal (see e.g. FIGS. 8A and 8B). In addition, in this area of the body, more than one nerve may supply adjacent and/or overlapping areas of a single anatomical structure. Sensory signals from these skin areas may be conveyed to centers in the brain by nerves including the auriculotemporal nerve, a branch of the trigeminal nerve, and also by other nerves (e.g., posterior auricular nerve, from the facial nerve, or the auricular branch of the vagus nerve). To achieve stimulation of the trigeminal nerve and other nerves in this manner, electrodes may be placed on the skin of the auricle and/or of the ear canal. Such embodiments are less noticeable when worn by a patient and may increase patient use and/or compliance.

Figure 8B:
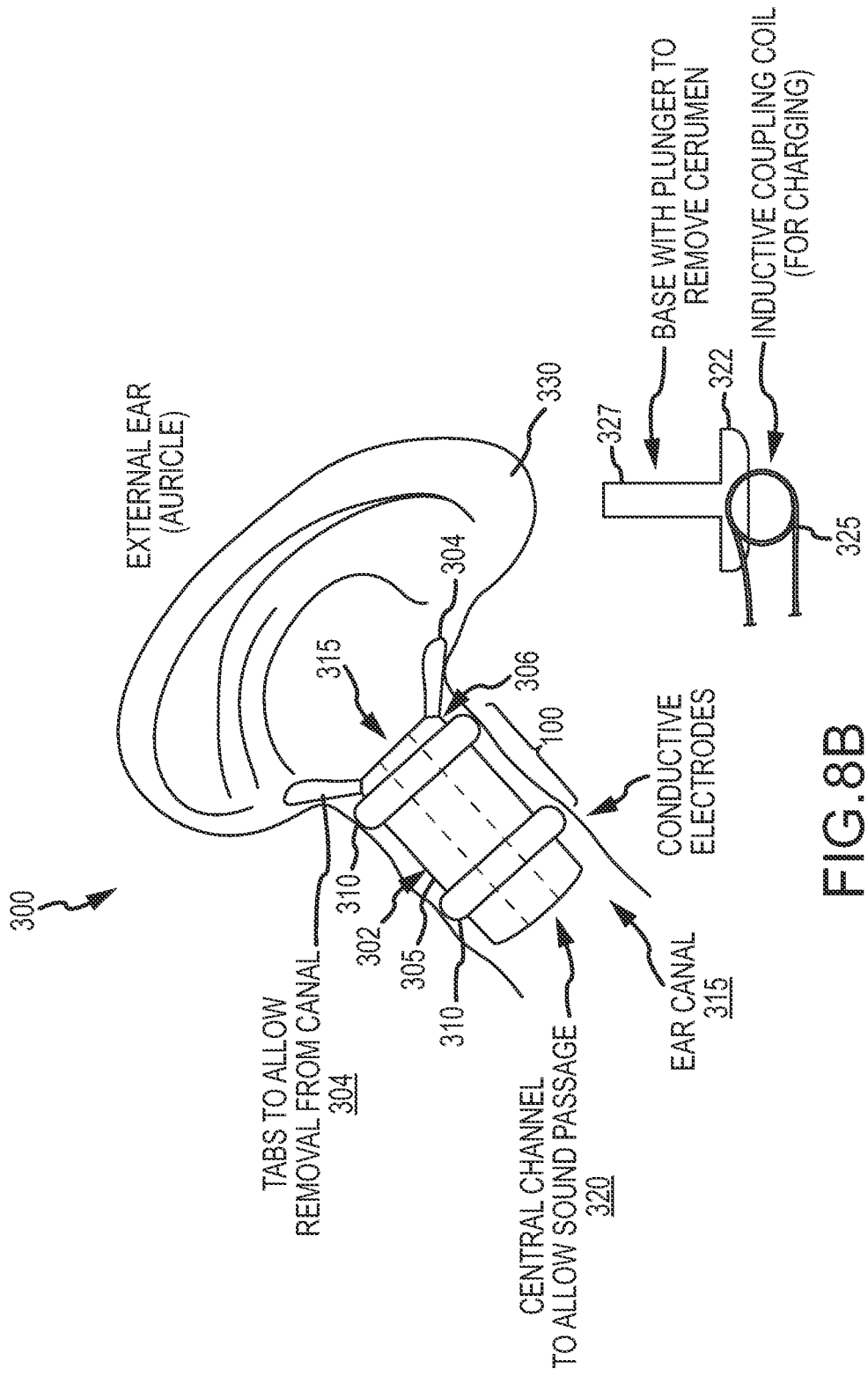

In one such embodiment, as illustrated in FIG. 8B, a "completely in the canal" or "CIC" system 300 may include a CIC device 302. The CIC device 302 includes electrodes or an electrode assembly 100 which may be configured as conductive rings or spots 310 placed on an outer circumferential surface of an elongated body or cylindrical device 305. The CIC device 302 may also include a pulse generator and a battery located within the elongated body 305 of the device 302. In some embodiments, the battery may be a non-rechargeable zinc air battery or other rechargeable battery known in the art. The electrode(s) or electrode assembly 100 and the pulse generator may be connected via a wire or similar connection, or may communicate wirelessly. Such communication may employ radio frequency, ultrasound, or other methods as may be apparent to one skilled in the art.

The CIC device 302 is configured to be received in the ear canal 315. In some embodiments, the elongated body 305 may have a hollow channel or a lumen 320 defined therethrough such that the ear canal 315 is not occluded and hearing is not reduced. The device 302 allows sound waves to propagate through the ear canal so the patient can still hear while wearing the device. In some embodiments, the CIC device 302 may include tabs 304 extending from a proximal end 306 of the elongated body 305. The tabs 304 are configured to be received in the entrance 314 of the canal 315 and aid the user in removing the device 302 from the ear canal 315.

The system 300 may further include a charging device, such as a charging stand or base 322. The base 322 may include an elongated plunger body 327 to remove cerumen (earwax). In some embodiments, the base 322 may further include an inductive coupling coil 325 for charging.

In use, the device 302 can be removed from the stand 322. The plunger body 327 of the stand 322 may be inserted into the ear to remove any ear wax. The stand and plunger body are removed. The CIC device 302 can then be inserted into the ear canal 315 and secured in place by resting the tabs 302 at the entrance 314 of the ear canal 315. Stimulation is provided to the target nerve(s) at operational parameters as disclosed herein upon communication between the pulse generator and the electrode assembly. When not in use, the CIC device 302 can be removed by grasping the tabs 304 and removing the device 305 from the ear canal 315 and placing it in a charging stand 322. The CIC device may be worn in one or both ear canals and for any prescribed length of time (or time of day) depending upon the indication to be treated.

In another embodiment, as illustrated in FIG. 8C-1, a "behind the ear" or "BTE" system 400 may include a BTE device 402 including an ear canal body 405 and an external ear body 410. The ear canal body 405 includes electrode(s) or an electrode assembly 100 configured to contact the surface of the skin within the ear canal 315, at the opening of the ear canal 316 or at/about another surface of the external ear 317. In some embodiments, the electrode(s) or electrode assembly 100 may be located on an external surface of the ear canal body 405. The ear canal body 405 is configured to be received at the opening of the ear canal and/or in the canal.

The external ear body 410 may also include a pulse generator and a battery located within the external ear body 410 of the device 402. In some embodiments, the electrode (s) or electrode assembly 100 may be located on an external surface of the external ear body 410. In some embodiments, the battery may be a non-rechargeable zinc air battery or other rechargeable battery known in the art. The electrode(s) or electrode assembly 100 and the pulse generator may be connected via a wire or similar connection, or may communicate wirelessly. Such communication may employ radio frequency, ultrasound, or other methods as may be apparent to one skilled in the art. The external ear body 410 is configured to be received and/or secured behind the ear, similar to an external hearing aid device. In some embodiments, the system 400 may also include a charging stand (not shown).

In use, and as illustrated in FIG. 8C-2, the BTE device 402 is inserted into the ear canal 315 or about the ear 330 and secured by placing the external ear body behind the ear 330. Stimulation is provided to the target nerve(s) at operational parameters as disclosed herein upon communication between the pulse generator and the electrode assembly. When not in use, the BTE device 402 can be removed from the ear 330 and placed in the charging stand. The BTE device may be worn on one or both ears and for any prescribed length of time (or time of day) depending upon the indication to be treated.

One skilled in the art can appreciate there may be various adaptations of the embodiments shown in FIGS. 8B-8C-2. For example, other devices, such as the ear piece of eyeglasses, in-ear headphones or headphones adapted to be placed outside the ear may include an electrode assembly 100, pulse generator and battery configured for use as described above with respect to FIGS. 8B-8C-2. Such devices may be configured to stimulate the trigeminal nerve by methods and for treatment of disorders as disclosed elsewhere herein. Such devices may increase patient use and/or compliance by camouflaging the TNS device.

Those skilled in the art will appreciate that various adaptations and modifications of the above-described embodiments of the electrode assembly 100 are within the scope and spirit of the present disclosure. For example, one embodiment of the present device comprises a unilateral electrode assembly configured for the unilateral stimulation of ophthalmic nerves. Also, the electrode assembly can also be configured for the stimulation of the maxillary nerves or the mandibular nerves. Alternatively, an electrode assembly configured for the simultaneous stimulation of a plurality of trigeminal nerve branches is also within the scope of the present disclosure. In one embodiment, the system or electrode assembly as disclosed herein may be configured to stimulate the infraorbital nerve branch.

In use, in one embodiment, the electrode assembly 100 is positioned over the forehead of the patient 20 such that the centerline of the insulative connection region 116 lines up with the midline of the patient's nose. In some embodiments, the electrode assembly 100 is placed over the supraorbital foramina, located over the orbital ridge approximately 2.1-2.6 cm lateral to nasal midline. The electrode assembly 100 may then be connected to the external neurostimulator 122 via lead wires 124 and the electrical cable 120. In other embodiments, the electrode assembly 100 is connected to the neurostimulator 122 via a wireless connection. Stimulation according to patient specific operational parameters as determined according to the methods described herein is then applied.

According to one aspect of the present disclosure, there is provided a method of treatment of medical disorders using the electrode assembly 100, as described above. In one embodiment, the method of treating medical disorders comprises positioning the electrode assembly 100 to the forehead of a patient, connecting the electrode assembly 100 to an external stimulator 122, and stimulating the electrode assembly 100 at defined values of the operational parameters as disclosed herein.

According to one aspect of the present disclosure, there is provided a method of treating medical disorders using an embodiment of the electrode assembly as described herein. In one embodiment, the method of treating medical disorders comprises positioning the electrode assembly at a first region of a face of a patient, connecting the electrode assembly to an external stimulator, and stimulating the electrode assembly at defined values of the operational parameters as disclosed herein. In one embodiment, the first region is a region corresponding to the auriculotemporal nerve. In one embodiment, the first region is a region corresponding to the zygomaticofacial nerve. In one embodiment, the first region is a region corresponding to the supraorbital nerve.

In one embodiment, the bilateral supraorbital electrode 100 illustrated in FIGS. 4-5A is stimulated at a stimulus frequency between about 1 Hz and about 300 Hz, at a pulse duration between 50 microseconds (μsec) and 500 μsec, at an output current density of less than 40 mA/cm$^2$ and an output charge density of less than 10 μCoulomb/cm$^2$ at the cerebral cortex for at least one-half to one hour per day. In other embodiments, the bilateral supraorbital electrode 100 illustrated in FIGS. 4-5A is stimulated at a stimulus frequency 120 Hz, at a pulse duration of 250 μsec, at an output current density of up to approximately 25 mA/cm$^2$ at a duty cycle of 30 seconds on/30 seconds off, and an output charge density of less than 10 μCoulomb/cm$^2$ at the cerebral cortex for at least eight hours per day. In some embodiments, the output current density is less than 7 mA, or less than 6 mA, depending on the size, impedance, resistance, or configuration of the electrode(s). In some embodiments, the output current density is between about 2.5 mA and about 5 mA. In still another embodiment, the output current may be limited to an exact current, e.g. 5 mA, up to a maximum of a fixed current of 7 mA, depending on the size, resistance, or impedance of the electrode. In another embodiment, the output current is limited to a range not to exceed 10 mA, or 7 mA, or 5 mA. In general, the stimulation would yield no or negligible charge densities at the cerebral cortex. In some cases, stimulation can be provided for less than one-half hour per day.

In some embodiments, the electrodes are arrayed in pairs, arranged as two pairs (4-contact), three pairs (six contact), or four pairs (eight contact), with current moving orthodromically (toward the proximal trigeminal ganglion). The electrodes are ≤than 50 mm$^2$ and <450 mm$^2$. In some embodiments, the electrodes are between approximately 50 mm$^2$ and 450 mm$^2$. The current amplitude provided by the system/electrode assembly is <2.5 mA, <5.0 mA, <7.5 mA, or not greater than 10 mA's). Such low current may reduce or minimize pain felt by the patient. In some embodiments, the specific limits to output current may be a function of physician programming, or automatically adjusted or programmed to the type, number of contacts, surface area, or impedance/resistance of the device.

Those of skill in the art will recognize that one or more of the above parameters can be used as a border of a range of parameters.

In various embodiments, the stimulation is delivered at a specific pulse width or range of pulse widths (or pulse duration). The stimulation can be set to deliver pulse widths in any range within a lower limit of about 10 microseconds and an upper limit of about 3 seconds. In various embodiments, the stimulation can be set to deliver pulse widths in the range greater than and/or less than one or more of 10 μs, 20 μs, 30 μs, 40 μs, 50 μs, 60 μs, 70 μs, 80 μs, 90 μs, 100 μs, 120 μs, 125 μs, 150 μs, 175 μs, 200 μs, 225 μs, 250 μs, up to 500 μs. Those of skill in the art will recognized that one or more of the above times can be used as a border of a range of pulse widths.

In some embodiments, the stimulation amplitude is delivered as a voltage or current controlled stimulation. In other embodiments it can be delivered as a capacitive discharge. In various embodiments, the current amplitude can be in any range within a lower limit of about 300 μA and an upper limit of about 30 mA-40 mA, depending on the surface area of the electrodes, inter-electrode distance, the branch(es) stimulated, and the modeling data as described above. In various embodiments, the amplitude can be in a range greater than and/or less than one or more of 50 μA, 75 μA, 100 μA, 125 μA, 150 μA, 175 μA, 200 μA, 225 μA, 250 μA, 275 μA, 300 μA, 325 μA, 350 μA, 375 μA, 400 μA, 425 μA, 450 μA, 475 μA, 500 μA, 525 μA, 550 μA, 575 μA, 600 μA, 625 μA, 650 μA, 675 μA, 700 μA, 725 μA, 850 μA, 875 μA, 900 μA, 925 μA, 950 μA, 975 μA, 1 mA, 2 mA, 3 mA, 4 mA, 5 mA, 6 mA, 7 mA, 8 mA, 9 mA, 10 mA, 11 mA, 12 mA, 13 mA, 14 mA, 15 mA, 16 mA, 17 mA, 18 mA, 19 mA, 20 mA, 25 mA, 30 mA, 35 mA and 40 mA. In some embodiments, the output current is less than 7 mA, or less than 6 mA, depending on the size, impedance, resistance, or configuration of the electrode(s). In some embodiments, the current amplitude is between about 2.5 mA and about 5 mA. In still another embodiment, the output current may be limited to an exact current, e.g. 5 mA, up to a maximum of a fixed current of 7 mA, depending on the size, resistance, or impedance of the electrode. In another embodiment, the output current is limited to a range not to exceed 10 mA, or 7 mA, or 5 mA. Those of skill in the art will recognize that one or more of the above amplitudes can be used as a border of a range of amplitudes, and that devices which use a voltage-based output can deliver a voltage output which at a range of electrode impedances would yield similar currents.

In various embodiments, the stimulation can be delivered at one or more frequencies, or within a range of frequencies. The stimulation can be set to be delivered at frequencies in any range within an upper limit of about 150 Hz and a lower limit of about 1 Hz. In various embodiments, the stimulation can be set to be delivered at frequencies less than, and/or greater than one or more of 50 Hz, 45 Hz, 40 Hz, 35 Hz, 30 Hz, 25 Hz, 20 Hz, 15 Hz, or 10 Hz. In various embodiments, the stimulation can be set to be delivered at frequencies greater than, and/or less than, one or more of 20 Hz, 30 Hz, 40 Hz, 50 Hz, 60 Hz, 70 Hz, 80 Hz, 90 Hz, 100 Hz, 120 Hz, 125 Hz, 150 Hz, up to 300 Hz. In some embodiments, where a higher frequency may be desired or required for treatment (such as tinnitus), the upper bound of the frequency may be 10,000 Hz (10 kHz). Those of skill in the art will recognize that one or more of the above frequencies can be used as a border of a range of frequencies.

In various embodiments, the stimulation is delivered at a specific duty cycle or range of duty cycles within a range from 100% down to about 5%. In various embodiments, the stimulation can be set to be delivered at a duty cycle in the range greater than and/or less than one or more of 5%, 10%, 15%, 20%, 25%, 30%, 35%, 40%, 45%, 50%, 55%, 60%, 65%, 70%, 75%, 80%, 85%, 90%, 95%, or 100%. In some embodiments, to ensure preservation of the nerve, a duty cycle of 10% to 50% may be preferable. In some embodiments, duty cycles up to 100% may be useful in particular circumstances. Those of skill in the art will recognize that one or more of the above percentages can be used as a border of a range of duty cycles.

In other embodiments, different values of the operational parameters may be used. In one embodiment, the values of the operational parameters are selected such that a patient will experience a stimulation sensation, such as a mild tingling over the forehead and scalp without being in discomfort or in pain. The neurostimulation parameters are important factors in the treatment method. In one embodiment, the values of the operational parameters are selected to minimize skin irritation, burns, undesired effects on the brain and/or the ophthalmic nerves. In one embodiment, the method of selecting operational parameters comprises evaluating variables such as the configuration and size of the electrode, the pulse duration, the electrode current, the duty cycle and the stimulation frequency, each of which are important factors in ensuring that the total charge, the charge density, and charge per phase are well within accepted safety limits for the skin, nerve and brain. For example, to minimize skin irritation, it is not sufficient to merely consider the total current, but the current density needs to be defined. Additionally, it is important to select the electrical stimulation parameters, electrode design, and inter-electrode distance, such that the electrical stimulation zone includes the ophthalmic nerve (approximately 3-4 mm deep), or other target nerve, while preventing or minimizing current penetration beneath the skull bone.

The stimulation is carried out at the above-described values of the operational parameters. The values of the operational parameters are advantageously selected such that a patient will experience a stimulation sensation, such as mild tingling over the forehead and scalp, without causing the patient marked discomfort or pain. These values may vary according to the treatment of interest; however, the systems and devices disclosed herein stimulate at parameters where current penetration below the surface of the skull and/or into the brain is prevented or minimized.

In addition to the direct application of an electrical signal of the desired characteristics (e.g., pulse width and shape, repetition frequency, amplitude), it will be apparent to one skilled in the art that the presence of such a signal in the target tissue (i.e., in the trigeminal nerve) can be effected through the use of interferential stimulation. In interferential stimulation, two (or more) signals are applied to the tissue of the body, and these signals are designed to differ from each other in such a way that when they combine ("heterodyne" or "interfere") within the tissue, they produce the desired signal (interference signal). This approach to creating a desired signal within nerve tissue may be advantageous in some clinical circumstances because the impedance of skin and adjacent tissue depends upon frequency, and this approach may allow for application of lower amounts of energy of the tissue to accomplish a clinically-effective level of nerve stimulation.

As discussed in more detail below with respect to FIGS. 15A-15B, when nerves are stimulated with a constant signal, at times they may accommodate to the presence of that stimulation and their response to the stimulation may decline over time. To avoid this issue of accommodation, it may be desirable in some circumstances to vary the specific details of the stimulus within ranges, though such means as sweeping the frequency of stimulation within a range of frequencies (e.g., rather than stimulate only at 120 Hz, the frequency of the signal may be varied by a specific range or frequencies over a programmable, pre-determined or random amount, for example a protocol as follows: 20 Hz for 10-60 minutes, 30 Hz for 10-60 minutes, 60 Hz for 10-60 minutes, 120 Hz for 10-60 minutes, 240 Hz for 10-60 minutes) or hopping from one discrete frequency of stimulation to another from time to time, or varying the width a stimulus pulse either continuously (swept within a range) or discretely (selected from a set of discrete pulse widths). As will be apparent to one skilled in the art, the varying may take on a variety of patterns, such as a triangular or trapezoidal ramp or a sinusoidal or similar modulation pattern. Also, varying the duty cycle or on-off times, for example ranging the duty cycle from 10% to 50% over 1-24 hours, 50% to 10% over 1-24 hours, than 50% to 100%, or other intervals and time periods so as to prevent or respond to accommodation of the nerve or its related target brainstem, brain structures, and associated brain regions.

In some embodiments, an external device may be used to identify the location of the branch or branches of the trigeminal nerve that will be targeted in an individual patient for stimulation by an implanted electrode assembly. The external device may be used for mapping and targeting the desired branch or branches of the trigeminal nerve and for identifying the individual stimulation parameters that are optimal for efficacy and safety. In one embodiment, the device may include a plurality of external (transcutaneous) TNS electrodes. The practitioner approximates the location of the target branch and affixes the electrodes to the patient's skin above the target location. Stimulation may be applied and the actual location or preferred (optimal) stimulation location of the target branch or branches may be determined. Stimulation parameters may also be established. Once the location and/or stimulation parameters have been established via the external device, that data may be used to help guide the placement of the implanted electrodes for an individual patient and to establish the customized stimulation parameters for that patient.

In addition, the use of external electrodes for stimulation of the trigeminal nerve may identify individuals who are likely to derive therapeutic benefit from a minimally invasive system in addition to the optimal specific locations and parameters of stimulation based on person-to-person variability. Various neurodiagnostic, imaging, or cutaneous nerve mapping methods may be able to delineate differences in individual anatomy to optimize stimulation for efficacy and/or safety. Furthermore, the use of a minimally invasive system may allow screening and identification of those individuals who are likely to derive benefit from other implantable systems. This can be conceptualized as linking the two approaches as stage I (external TNS of the trigeminal nerve), and stage II (implanted TNS of the superficial trigeminal nerve), such that stage I can screen for stage II. By monitoring a patient for evidence of useful therapeutic effect, such as by reduction in the severity of symptoms or reductions in heart rate, the results of treatment at one stage may be used to judge the likely effect of treatment with a more invasive treatment from a higher stage.

Personalized and Varying Stimulation Parameters

In some embodiments, externally applied electrodes are placed on the skin over the trigeminal nerve dermatomes (e.g., forehead), and gentle electrical signals are used to stimulate the nerve, typically for 8 hours (while sleeping), using stimulation parameters such as a pulse width of 250 microsec, repetition rate of 120 Hz, duty cycle of 30 s on then 30 s off, and current of up to 25 mA. The electrical signals have been shown to lead to selective activation or inhibition of a set of brain structures, such as the locus coeruleus and the anterior cingulate.

Data indicates that stimulation at other parameters may have clinical effects as well, such as a frequency in the range of 1 to 10 Hz, a cycle of 2 seconds on and 90 seconds off, and pulse widths between 100 to 500 microseconds. In one embodiment, the system may deliver stimulation at one set of parameters (e.g., 120 Hz, 250 microsec) for a period of time (e.g., several minutes) followed by a different set of parameters (such as 60 Hz, 200 microsec) for a period of time, then other additional parameter sets (e.g. 2 Hz, 250 microsec) before cycling back to the first set.

Figure 9:
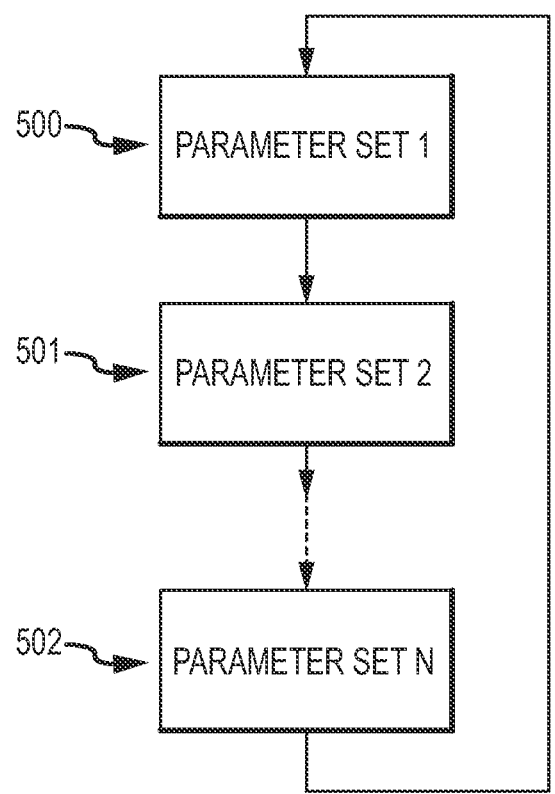
FIG. 9 depicts one embodiment of the sequential employment of N sets of stimulation parameters in accordance with aspects of the present disclosure.

FIG. 9 illustrates the sequential employment of N sets of parameters, with Parameter Set 1 500, Parameter Set 2 501, on through the final, Nth set 502 Parameter Set N. In one embodiment, the first parameter set 500 (Parameter Set 1) is employed by the stimulation generator for the duration specified in the parameter set. Once those stimuli have been produced, a second parameter set 501 (Parameter Set 2) is employed, and this sequential utilization of different parameter sets continues until the final (Nth) parameter set 502 (Parameter Set N) is employed, after which the sequence may begin again. This cycling through the N different parameter sets may occur repeatedly during the treatment administration.

In some embodiments, a plurality of stimulation parameters may be used to improve the clinical treatment effects. In such a system, several sets of parameters are utilized and the system may automatically vary the stimulation among the sets of parameters. This plurality of sets is intended to avoid any adaptation of the patient's nervous system to repeated exposure to the same unvarying stimulation pattern. In some embodiments, the stimulation pattern is selected to prevent or minimize current penetration into the brain.

In some embodiments, a system and method in which measurement of a biological feature (e.g., activity in a brain region) is used to detect an acute biological change which may be used to select a personalized set of parameters (such as repetition frequency, pulse width, or duty cycle) which are predicted to produce an intended clinical effect (or the absence of that effect for use as a sham (placebo) control condition).

Use of imaging or other biological measures to personalize the stimulation parameters to be used in Trigeminal Nerve Stimulation may improve the clinical treatment effects. In some embodiments, instead of delivering the stimulation at a set or sets of parameters selected based on prior studies of groups of individuals with the same clinical condition (e.g., epilepsy or depression), the treating physician may monitor the individual patient's biological response to stimulation, such as with a PET neuroimaging scan (see description related to FIGS. 2 and 3 above), an EEG-derived value of current density in the brain, a fMRI scan, measures of heart activity or blood pressure, or other such measure, to select personalized parameters that produce an acute change in a biological measure which is linked to and may be predictive of later clinical outcomes. Additionally, parameters may be selected for use in a clinical research study in order to have a set of parameters which is unlikely to produce the desired clinical effect (i.e., for use as a sham (placebo) control condition). Additionally, this approach may be used to determine if there is penetration of current into the brain tissue directly from the stimulating electrodes.

FIG. 10 depicts a system 610 for determining patient specific stimulation parameters. In one embodiment, the system 610 includes a biological sensing device 601, a measurement or measuring device 602 and a stimulation generator 604. The biological sensing device may be a neuroimaging device, such as a magnetic resonance imaging (MRI) scanner, a positron emission tomography (PET) scanner, or similar device; or a physiologic device, such as an electroencephalograph (EEG), an electrocardiograph (ECG or EKG), a blood pressure sensory, pulse oximeter, or other similar device. The data from the sensing device is provided to a measurement or measuring device 602 such as an imaging workstation, a computer to perform quantitative analysis of EEG signals, a graphical display of electrocardiographic data, or similar system. The information from the measurements is interpreted by the prescribing physician 603 or other clinician, and is used to make adjustments to the stimulation parameters of the generator 604 to achieve a personalized setting which may lead to a desired clinical effect. As will be apparent to one skilled in the art, aspects of the adjustments may be made through an automated device in lieu of the person 603.

In use, a patient 600 is placed in proximity to a biological sensing device 601, which is coupled, either directly or indirectly to a measurement or measuring device 602. Output from the measuring device 602 is observed by the prescribing physician or other clinician 603 and adjustments may be made to the stimulation parameters as disclosed elsewhere herein that are supplied by the stimulation generator 604 to the trigeminal nerve of patient 600.

EXAMPLES

The following examples are presented to set forth more clearly the subject matter of this disclosure without imposing any limits on the scope thereof and to illustrate the clinical benefits of trigeminal nerve stimulation for the treatment of medical disorders, including but not limited to, neuropsychiatric disorders, cardiac related disorders and fatigue or other medical disorders. In the first example, patients with major depressive disorder were treated by TNS with external cutaneous electrodes. In the second example, a patient was treated using cutaneous electrodes for bilateral supraorbital stimulation. In the third example, patients were treated using cutaneous electrodes for bilateral supraorbital and/or infraorbital stimulation and the group average data is presented. In the fourth example, patients were treated using cutaneous electrodes for bilateral supraorbital stimulation. In the fifth example, a sample protocol for mitigating potential accommodation is presented.

Example 1

Figures 11A, 11B:
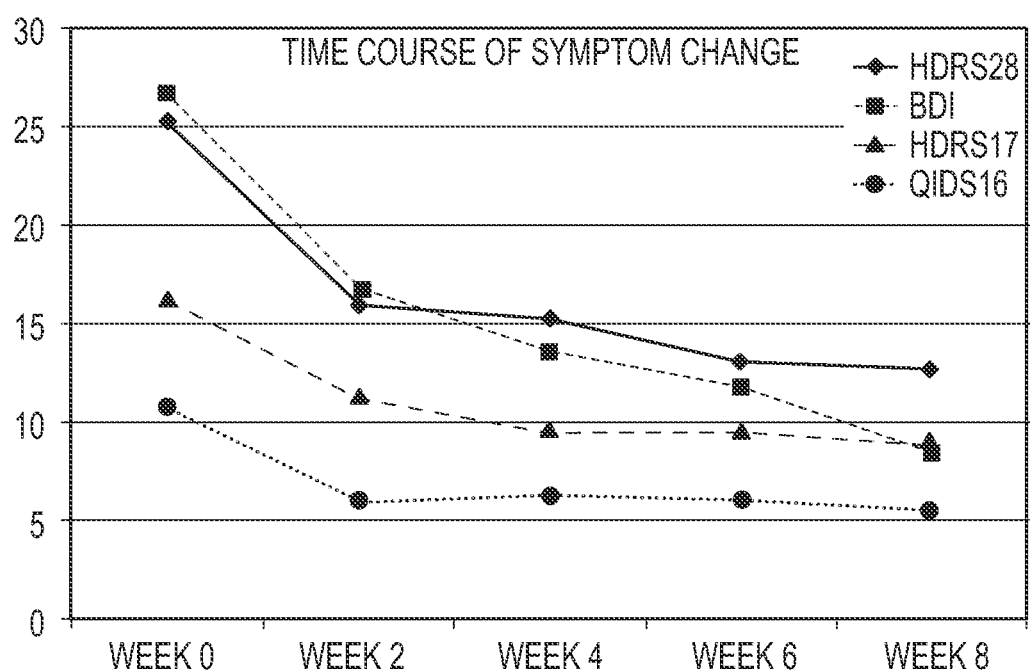
FIG. 11A is a table showing an average of the results of four assessment tests pre-treatment and post treatment of a treatment study for psychiatric disorders using aspects of the present disclosure.
FIG. 11B is a bar graph of the data shown in FIG. 11A.
Figure 11C:
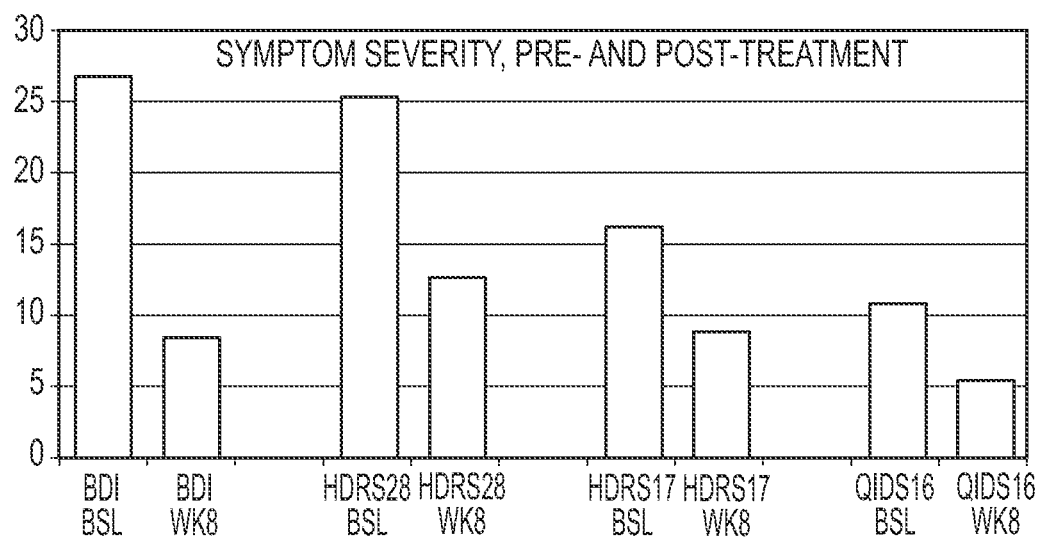
FIG. 11C is a graph illustrating the change over time of the data shown in FIG. 11A.

FIGS. 11A-11C illustrate the results from a pilot study of external trigeminal nerve stimulation for the treatment of depression. Subjects with major depression who met inclusion and exclusion criteria were followed for 8-weeks in an open label (unblinded) study conducted at UCLA.

Inclusion Criteria were: Age 18-65 years old who met DSM-IV criteria for an acute, recurrent episode of Major Depressive Disorder (MDD) and were in a major depressive episode (MDE) of moderate severity. Other inclusion criteria were: the current MDE must be ≥4 months in duration, no response to at least one antidepressant over at least six weeks during the current MDE, and concomitant use of at least one antidepressant. All had prominent residual symptoms, with mean Hamilton Depression Rating Scale (HDRS-28) scores at study entry of 25.4 (3.9 s.d.), range 19 to 29. Subjects placed stimulating electrodes over the supraorbital branches of the trigeminal nerve for at least 8 hours per day (primarily while asleep), with current adjusted to maintain comfortable levels. Five subjects completed the trial. Primary outcome was change in HDRS at 8 weeks.

Exclusion criteria were: current pregnancy; meeting DSM-IV criteria for atypical or psychotic or bipolar depression; a history of schizophrenia, schizoaffective disorder, or other non-mood disorder psychosis; a current secondary DSM-IV diagnosis (or signs) of delirium, dementia, amnestic disorder or other cognitive disorder; clinically significant current suicidal intent; significant cardiac, medical or progressive neurological or medical illness; facial pain or trigeminal neuralgia; a VNS or other implantable electrical device such as a pacemaker; current use of a TENS or VNS unit, or history of non-compliance.

All subjects received unblinded TNS augmentation (adjunctive) treatment for at least 8-hours each day. Assessments were made at study intake, and at weeks 2, 4, 6, and 8 in the acute treatment phase. Subjects who wished to continue the treatment were allowed to participate in an optional 6-month long-term extension phase with monthly monitoring visits.

Subjects underwent stimulation using an electrical stimulator, such as for example the EMS Model 7500 commercially available from TENS Products, Inc. operated at a frequency of 120 Hertz, a current less than 20 mA, a pulse duration of 250 μsec, and a duty cycle at 30 seconds on and 30 seconds off, for a minimum of 8 hours per day.

Prior to initiating treatment and at subsequent follow-up assessment visits, the symptom severity of each subject was quantified using the Hamilton Depression Rating Scale (HDRS, scored using both 17- and 28-item versions), the Beck Depression Inventory (BDI), and the Quick Inventory of Depressive Symptomatology (QIDS), with the group average values on each of these scales being tabulated in the table shown in FIG. 6A. All three are assessment instruments designed to measure the severity of depression. The HDRS is a well-established rating scale instrument which is filled out by a clinician after interviewing and observing the individual subject in order to measure the severity of depression; in this study, ratings on all 28 items (questions) were made, and the scale was scored according to standard methods using all items ($HDRS_{28}$) and the standard subset of 17 items ($HDRS_{17}$). The BDI is a 21-question multiple choice self-report survey that is used to measure the severity of depression. The $QIDS-C_{16}$ is a 16-question clinician-rated survey that is used to measure the severity of depression. Each of these scales affords different strengths and limitations in assessing a patient's symptom severity (e.g. BDI emphasizes cognitive symptoms of depression, while the HDRS weights neurovegetative symptoms prominently), and all are commonly used in clinical trials in major depression; the use of multiple scales allowed a more comprehensive assessment of the effects of trigeminal nerve stimulation than any single scale in this initial study of this treatment for major depression.

As shown in FIG. 11A, and graphically illustrated in FIGS. 11B and 11C, decreases in $HDRS_{28}$ were significant, from 25.4 (3.9 s.d.) at entry to 13.6 (6.3 s.d.) at week 8 (2-tail t-test p<0.01, Cohen's d 2.4). Responses on the BDI similarly declined, from 26.8 (8.1) to 10.6 (4.9) (p<0.01, d 2.3). Decreases on the 16-item clinician-rated QIDS were also significant, decreasing from 10.8 (3.4) to 5.5 (4.4) (p<0.05, d 1.3). Thus, significant decreases in symptom severity were achieved in the 8 weeks of acute TNS treatment. Furthermore, changes in symptoms occurred across all symptom areas, such as depressed mood, anxiety, sleep, and energy. These findings support the use of TNS treatment which may also have use as an adjunct to pharmacotherapy when medications have failed to produce remission of symptoms.

Example 2

FIG. 12 summarizes current, charge, current density and charge density recorded in a subject during exposure to cutaneous stimulation of the supraorbital nerve. FIG. 7 illustrates representative parameters for bilateral supraorbital stimulation recorded in a subject using an EMS 7500 stimulator, 120 HZ, 150-250 usec, Tyco superior silver electrodes 1.25", placed one inch from the midline above the eyebrows. Data recorded with Fluke Oscilloscope, 50 mV/div, resistor=10.1Ω. In general, these findings show that, as the pulse width increased, the maximum tolerable current decreased.

Cutaneous electrical stimulation of the supraorbital branch of the trigeminal nerve with round 1.25-inch TENS patch electrodes results in current densities and charge density/phase that are well within the limits of safety. In general, the maximum current comfortably tolerated by TNS patients studied previously is approximately 25 mA, and patients typically are stimulated at an amplitude setting well below 25 mA (6-10 mA).

The 1.25-inch TENS electrodes are circular electrodes with a radius of 1.59 cm. The surface area can be calculated as $A=11\ \Pi^2=[\Pi]\times[1.59\ cm]^2=7.92\ cm^2$. Using these electrodes, typical stimulation current ranges from 6-10 mA at pulse durations of 150-250 usec.

Current Density: In a typical subject, stimulation currents of 6-10 mA result in current densities ranging from 0.76 to 1.3 $mA/cm^2$. McCreery et al have established a maximum safe current density of 25 $mA/cm$ at the stimulating electrode for transcranial electrical stimulation. Assuming even higher currents of up to 25 mA with electrodes of surface area 7.92 $cm^2$, current densities may range to a maximum of 3.16 $mA/cm^2$. From 0.76 $mA/cm^2$ to 3.16 $mA/cm^2$, TNS delivers a current density 8-33 times less than the maximum safe allowable current density. Charge Density (Charge density/phase): Yuen et al have identified a safe limit for charge density/phase delivered at the cerebral cortex of 40 uC/cm$^2$. [Yuen et al 1981] and more recently McCreery et al. (McCreery et al 1990) have identified 10 uC/cm$^2$ as the safe limit. Assuming 10 mA at 250 usec, the charge density/phase is [0.010 A]×[250 usec]/7.92=0.32 uC/cm$^2$ at the stimulating electrode. Assuming even higher levels of stimulation, 25 mA at 250 usec, the maximum charge density per phase is 0.79 uC/cm$^2$. At these levels, the charge density is generally 12 to 120 fold less at the stimulating electrode than the maximum allowed at the cerebral cortex. Since the cortex is a minimum of 10-13 mm from the stimulating electrodes, and given the interposed layers of skin, fat, bone, dura, and CSF, the actual charge densities will be significantly lower. This is of importance in avoiding the undesired passage of current directly through brain tissue as a bulk conductor.

As shown in FIG. 12, stimulation intensity responses in a subject with electrodes of surface area 7.92 cm2, at pulse durations between 150-250 usec, results in current densities at the scalp well below currently recommended current densities for transcranial stimulation, which are 25 mA/cm$^2$, and charge densities at the scalp significantly lower than safe charge densities at the cerebral cortex (0.15-0.18 uC/cm$^2$).

Example 3

Figure 13:
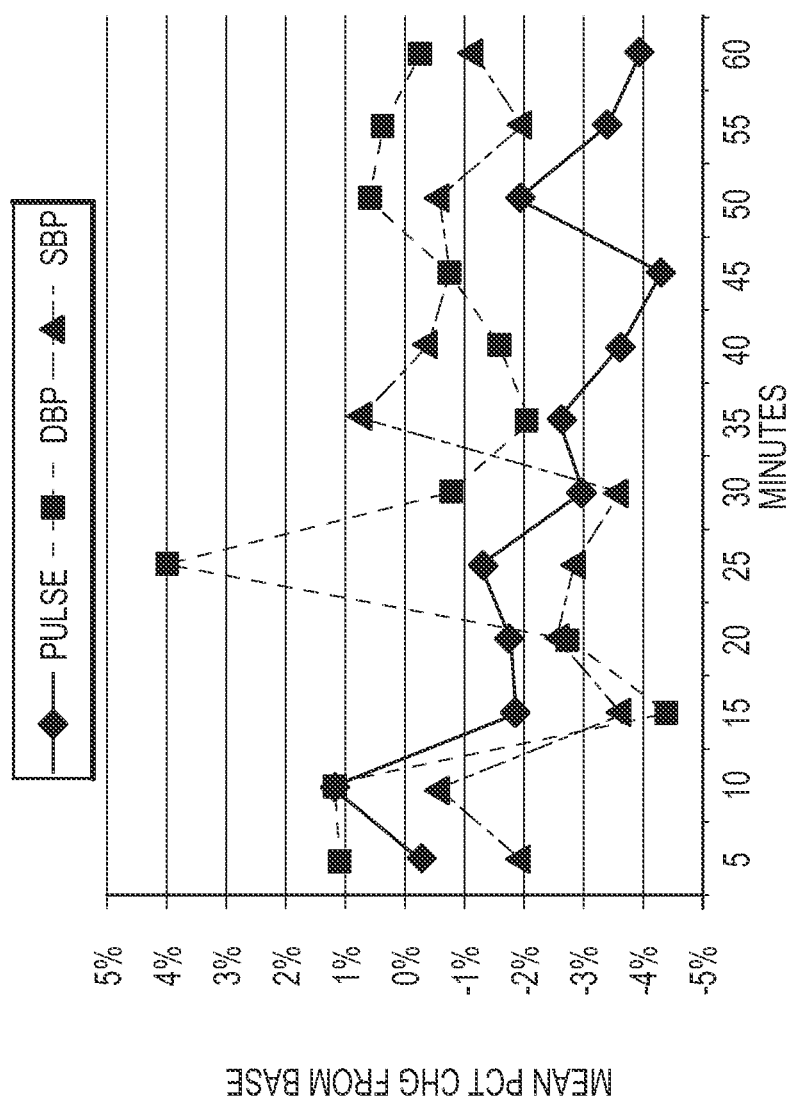
FIG. 13 illustrates patient response to cutaneous stimulation of the supraorbital and infraorbital nerve according to one aspect of the present disclosure.

FIG. 13 illustrates the response to TNS at 120 Hz, 10-30 seconds on/30 seconds off, infraorbital or supraorbital stimulation in patients with epilepsy. Note the measured and mild reductions in heart rate, consistent with activation of the Trigeminal Cardiac Reflex. This reflects the effects of vagus nerve stimulation from Trigeminal Nerve Stimulation. Mild reductions in heart rate occur without significant changes in systolic or diastolic blood pressure. The reduction in heart rate is protective in the setting of myocardial infarction, heart failure, tachyarrhythmia's, and conditions associated with the risk of sudden death.

Example 4

Figure 14:
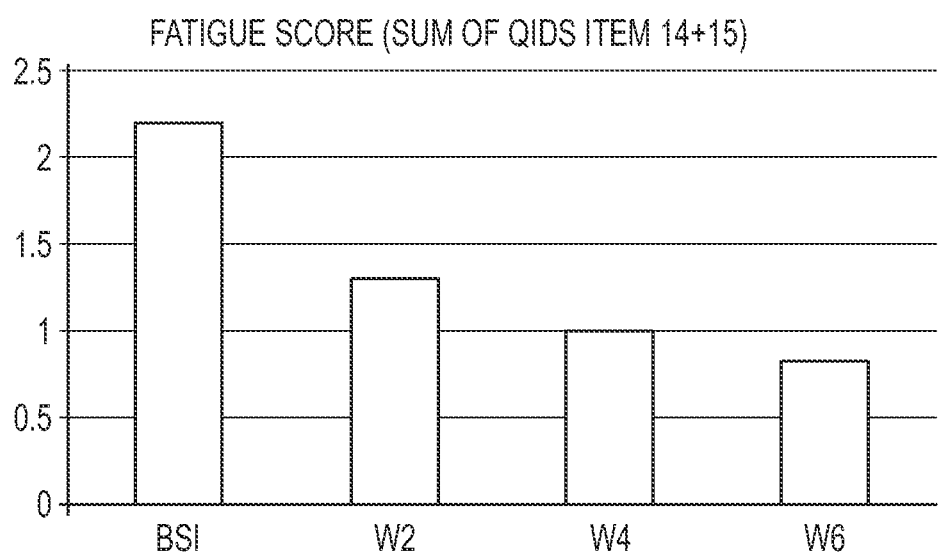
FIG. 14 illustrates patient response to cutaneous stimulation of the trigeminal nerve according to one aspect of the present disclosure.

FIG. 14 illustrates the changes in fatigue scores with trigeminal nerve stimulation. Data was collected from 10 adults who received TNS nightly. The level of fatigue was assessed using the sum of items 14 ("energy level") and 15 ("feeling slowed down") on the Quick Inventory of Depressive Symptomology. Mean scores declined from a level of 2.2 (s.d1.3) at pretreatment baseline (bsl), to 0.8 (s.d. 0.9) at six weeks of treatment (w6), a statistically significant improvement (2 tailed paired t test p=0.001).

Example 5

Figure 15B:
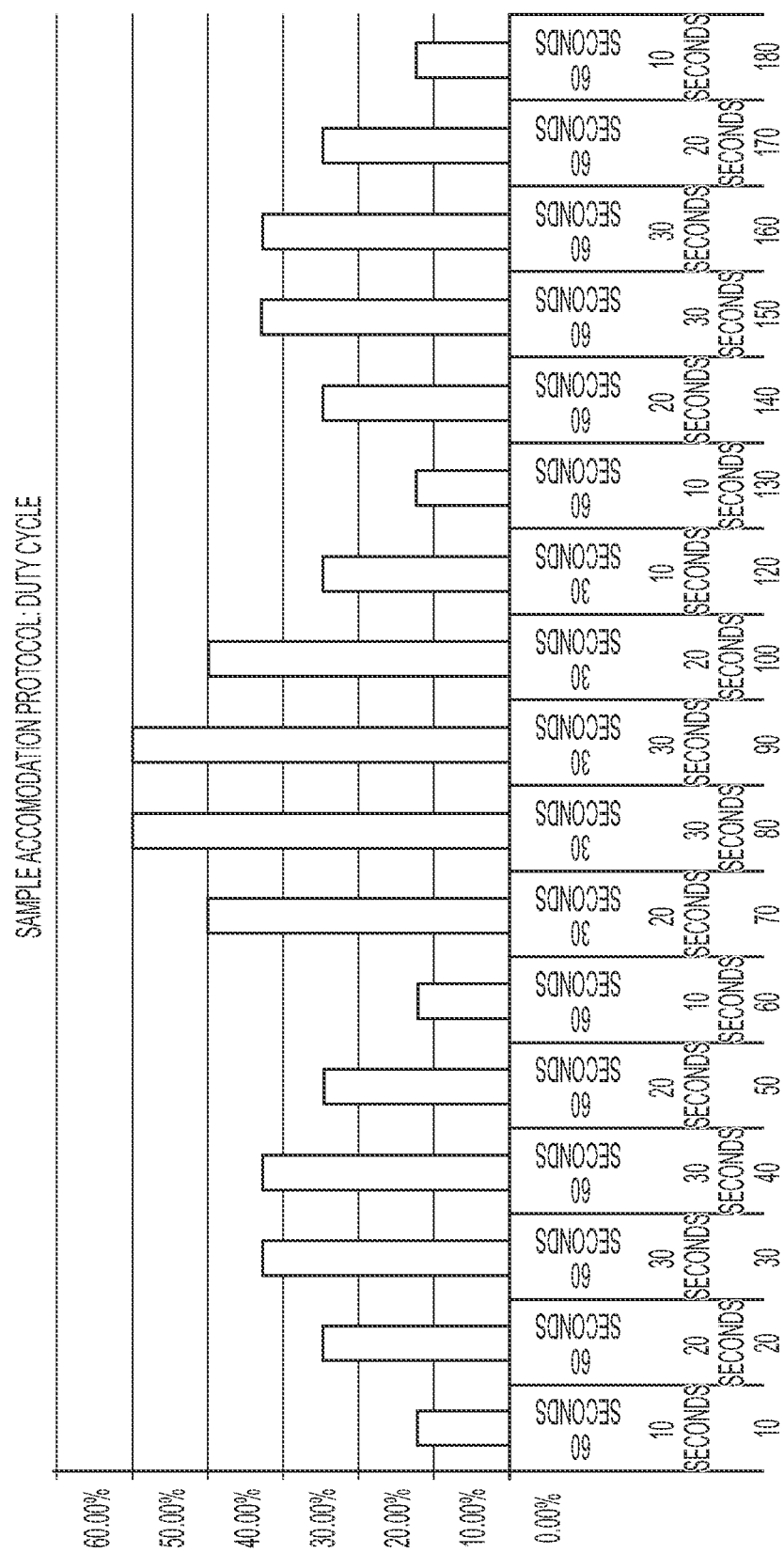

FIGS. 15A-15B illustrate a sample protocol for mitigating the potential effects of accommodation.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification and examples provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. For example, stimulation of the target nerve may be accomplished by cutaneous application of energy in many forms, such as magnetic or ultrasonic. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A method, comprising:

contacting an external cutaneous electrode assembly with a patient's forehead by applying a first contact of the external cutaneous electrode assembly over or adjacent to a supraorbital nerve on one side of the patient's forehead and applying a second contact of the external cutaneous electrode assembly over or adjacent to a remaining supraorbital nerve on an opposing side of the patient's forehead; and applying electrical signals to the external cutaneous electrode assembly to stimulate the supraorbital nerves at the patient's forehead, while minimizing current penetration into a brain of the patient, to modulate a body system of the patient by increasing activation of a medial prefrontal cortex, a superior frontal gyrus, a lateral frontal cortex, and a middle temporal gyrus and/or inhibiting a superior parietal cortex and a temporal-occipital cortex to treat a medical disorder, the medical disorder selected from the group consisting of attention deficit disorder (ADD) and attention deficit hyperactivity disorder (ADHD).

2. The method of claim 1, wherein the applying of the electrical signals comprises applying electrical signals at a frequency between 20 and 300 Hertz, at a pulse duration between 50 and 500 microseconds, at an output current density of not greater than 10 mA/cm$^2$ and a charge density of not greater than 10 microCoulomb/cm$^2$ at the patient's cerebral cortex.

3. The method of claim 1, wherein the applying of the electrical signals comprises applying electrical signals at a frequency between 20 and 300 Hertz, at a current of 0.1 to 3 milliamperes (mA), and at a pulse duration of less than or equal to 500 microseconds.

4. The method of claim 1, wherein the applying of the electrical signals comprises applying electrical signals at an output current density of not greater than 10 mA/cm$^2$.

5. The method of claim 1, wherein the applying of the electrical signals comprises applying electrical signals at an output current density of between 2.5 and 5 mA/cm$^2$.

6. The method of claim 1, wherein the applying of the electrical signals comprises applying electrical signals at an output current density of not greater than 7 mA/cm$^2$.

7. The method of claim 1, wherein the applying of the electrical signals comprises applying electrical signals at an output current density of not greater than 5 mA/cm$^2$.

8. The method of claim 1, wherein the applying of the electrical signals comprises applying the electrical signals to the first contact independent from the second contact.

9. The method of claim 1, wherein the applying of the electrical signals comprises adjusting the electrical signals to the first contact independent from the second contact.

* * * * *